US009988625B2

(12) United States Patent
Leake et al.

(10) Patent No.: US 9,988,625 B2
(45) Date of Patent: Jun. 5, 2018

(54) TEMPLATES, LIBRARIES, KITS AND METHODS FOR GENERATING MOLECULES

(71) Applicant: GE Healthcare Dharmacon, Inc., Lafayette, CO (US)

(72) Inventors: Devin Leake, Lexington, MA (US); Annaleen Vermeulen, Lafayette, CO (US); Brady Culver, Englewood, CO (US); Abel Licon, Longmont, CO (US); Joshua A. Stahl, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 334 days.

(21) Appl. No.: 14/758,391

(22) PCT Filed: Jan. 7, 2014

(86) PCT No.: PCT/US2014/010428
§ 371 (c)(1),
(2) Date: Jun. 29, 2015

(87) PCT Pub. No.: WO2014/110006
PCT Pub. Date: Jul. 17, 2014

(65) Prior Publication Data
US 2015/0353927 A1 Dec. 10, 2015

Related U.S. Application Data

(60) Provisional application No. 61/751,157, filed on Jan. 10, 2013.

(51) Int. Cl.
C12N 15/63 (2006.01)
C12N 15/10 (2006.01)
C07H 21/04 (2006.01)
C12N 15/64 (2006.01)
C12N 15/86 (2006.01)

(52) U.S. Cl.
CPC .................. *C12N 15/1093* (2013.01)

(58) Field of Classification Search
None
See application file for complete search history.

(56) References Cited

U.S. PATENT DOCUMENTS

| | | | |
|---|---|---|---|
| 4,973,679 A | 11/1990 | Caruthers et al. |
| 2002/0146723 A1 | 10/2002 | Krontiris et al. |
| 2002/0192721 A1 | 12/2002 | Rizzuto et al. |
| 2003/0124594 A1 | 7/2003 | Church et al. |
| 2003/0165859 A1 | 9/2003 | Nazarenko et al. |
| 2004/0259146 A1 | 12/2004 | Friend et al. |
| 2005/0089904 A1 | 4/2005 | Beaulieu et al. |
| 2006/0014167 A1 | 1/2006 | Church et al. |
| 2006/0040316 A1 | 2/2006 | Tsuchiya et al. |
| 2006/0127920 A1 | 6/2006 | Church et al. |
| 2006/0166913 A1 | 7/2006 | Suzuki |
| 2006/0281113 A1 | 12/2006 | Church et al. |
| 2007/0004041 A1 | 1/2007 | Church et al. |
| 2007/0269870 A1 | 11/2007 | Church et al. |
| 2009/0075840 A1 | 3/2009 | Myerson et al. |
| 2009/0137407 A1 | 5/2009 | Church et al. |
| 2009/0317910 A1 | 12/2009 | Church et al. |
| 2010/0047876 A1 | 2/2010 | Church |
| 2010/0099080 A1 | 4/2010 | Church et al. |
| 2010/0304994 A1 | 12/2010 | Wu et al. |
| 2011/0039304 A1 | 2/2011 | Church et al. |
| 2011/0172127 A1 | 7/2011 | Jacobson et al. |
| 2013/0178428 A1 | 7/2013 | Hoon et al. |

FOREIGN PATENT DOCUMENTS

| | | |
|---|---|---|
| WO | 2004/001044 A1 | 12/2003 |
| WO | 2007/087291 A2 | 8/2007 |
| WO | 2010/011346 A1 | 1/2010 |
| WO | 2010007797 A1 | 1/2010 |
| WO | 2010096696 A2 | 8/2010 |
| WO | 2012/018881 A2 | 2/2012 |
| WO | 2012018881 A2 | 3/2012 |

OTHER PUBLICATIONS

Silva et al., "Second-generation shRNA libraries cov ering the mouse and human genomes" 37(11) Nature Genetics 1281-1288 (2005).*
Response to Examiner's Response to European Extended Search Report, EP 14737758.4, dated Mar. 30, 2017.
Response to Examiner's Response to European Extended Search Report, EP 14737758.4, dated Feb. 26, 2016.
Communication Pursuant to Article 94(3) EPC, EP 14737758.4, dated Jul. 26, 2017.
Commissioner of Patents, Australian Intellectual Property Office, Examination Report, 2014205648, dated Dec. 21, 2016.
Spruson & Ferguson, Response to Examiner's Response to Australian Search Report, 2014205648, dated Mar. 23, 2017.
Jinek, Martin, et al., A Programmable Dual RNA-Guided DNA Endonuclease in Adaptive Bacterial Immunity, Science, Aug. 17, 2012, vol. 337, pp. 816-821 and Supplemental Materials published on-line Science Express DOI: 10.1126/science.1225829.
Pritchard, Leighton et al., A general model of error-prone PCT, J. Theo. Biol., 234 (2005): 497-509.
Kosuri, Sriram, et al., A Scalable Gene Synthesis Platform Using High-Fidelity DNA Microchips, Nat. Biotechnol. Dec. 2010; 28(12):1295-1299.

(Continued)

Primary Examiner — Nancy J Leith
(74) Attorney, Agent, or Firm — Dorf & Nelson LLP; Scott D. Locke, Esq.

(57) ABSTRACT

The present invention is directed to collections of templates for molecules such as RNA, as well as templates, devices, kits and methods for generating molecules from these collections. Through the use of various embodiments of the present invention one may efficiently and effectively obtain selected RNA molecules such as siRNA, shRNA, miRNA mimics and inhibitors, lncRNA, antisense RNA, aptamers, ribozymes, and sgRNA and sets of those molecules.

16 Claims, 23 Drawing Sheets

(56) References Cited

OTHER PUBLICATIONS

Li, Hanying, et al., Nanofabrication by DNA self-assembly, Materials Today, May 2009, vol. 12, No. 5, pp. 24-32.
Matzas, Mark, et al., High-fidelity gene synthesis by retrieval of sequence-verified DNA identified using high-throughput pyrosequencing, Nature Biotechnology, Advance on-line publication, (2010) pp. 1-4.
International Search Report and Written Opinion, for PCT/US2014/010428, 32 pages, Mar. 28, 2014.
European Patent Office, Extended European Search Report, dated Sep. 8, 2016.

* cited by examiner

FROM (A) ON FIG. 8A

IN VITRO DICER CLEAVAGE, RANDOM POSITIONS

| | |
|---|---|
| SEQ ID NO: 21 | 5' – AAAAAANNNNNNNNNNNNNNNNNNNNNNNUU |
| SEQ ID NO: 22 | CUUUUUUNNNNNNNNNNNNNNNNNNNNNNN –5' |
| SEQ ID NO: 23 | 5' – NNNNNNNNNNNNNNNNNNNNNNNUUUUUUU |
| SEQ ID NO: 24 | UUNNNNNNNNNNNNNNNNNNNNNNAAAAA – 5' |
| SEQ ID NO: 25 | 5' – AAAANNNNNNNNNNNNNNNNNNNNNNNNUU |
| SEQ ID NO: 26 | UUUUUNNNNNNNNNNNNNNNNNNNNNNNNA – 5' |
| SEQ ID NO: 27 | 5' – AANNNNNNNNNNNNNNNNNNNNNNNNUUU |
| SEQ ID NO: 28 | UUUUNNNNNNNNNNNNNNNNNNNNNNNNAA – 5' |

25 – 27 nt dsRNAs

FIG. 8B

PROCESS IN VITRO WITH DICER

SENSE STRAND
SEQ ID NO:47  5' – GGGNNNNNNNNNNNNNNNNNNNNNNNUU
SEQ ID NO:48           UUNNNNNNNNNNNNNNNNNNNNNNN – 5'
ANTISENSE STRAND

FROM (A) ON FIG. 10A

USE AS shRNA

```
                                                    U A G C
                                                   C     C
SENSE STRAND                                      N      G
SEQ ID NO:49  5' – GGGNNNNNNNNNNNNNNNNNNNNNNNN   G
                   UUNNNNNNNNNNNNNNNNNNNNNNN    G A
ANTISENSE STRAND
```

→ OR ←

```
                                                    U C G
                                                   C     G
SENSE STRAND                                      N      C
5' – AANNNNNNNNNNNNNNNNNNNNNNNN                  N
     CCCNNNNNNNNNNNNNNNNNNNNNN                    A A U
ANTISENSE STRAND                                          SEQ ID NO:50
```

PROCESS IN VITRO WITH DICER

SENSE STRAND
SEQ ID NO:51  5' – GGGNNNNNNNNNNNNNNNNNNNNNNNUU    SEQ ID NO:53
SEQ ID NO:52           UUNNNNNNNNNNNNNNNNNNNNNNN – 5'  SEQ ID NO:54
ANTISENSE STRAND

SENSE STRAND
5' – AANNNNNNNNNNNNNNNNNNNNNNNNUU
     CCCNNNNNNNNNNNNNNNNNNNNNNN – 5'
ANTISENSE STRAND

FIG. 10B

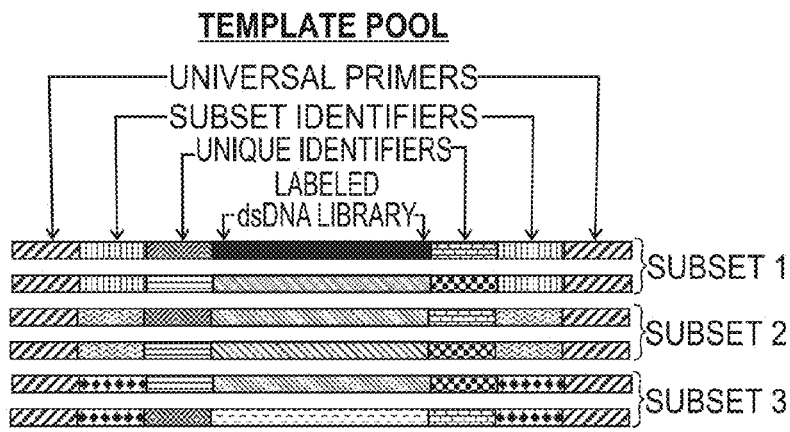
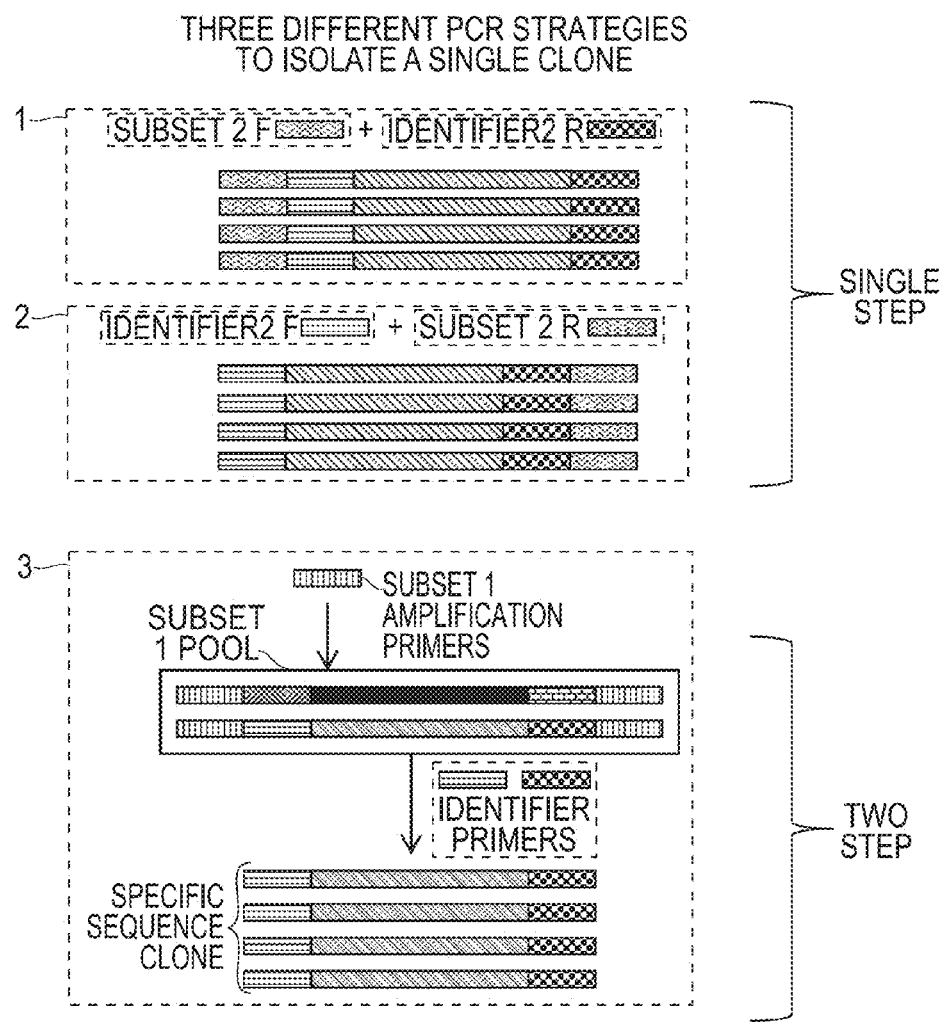
FIG. 14

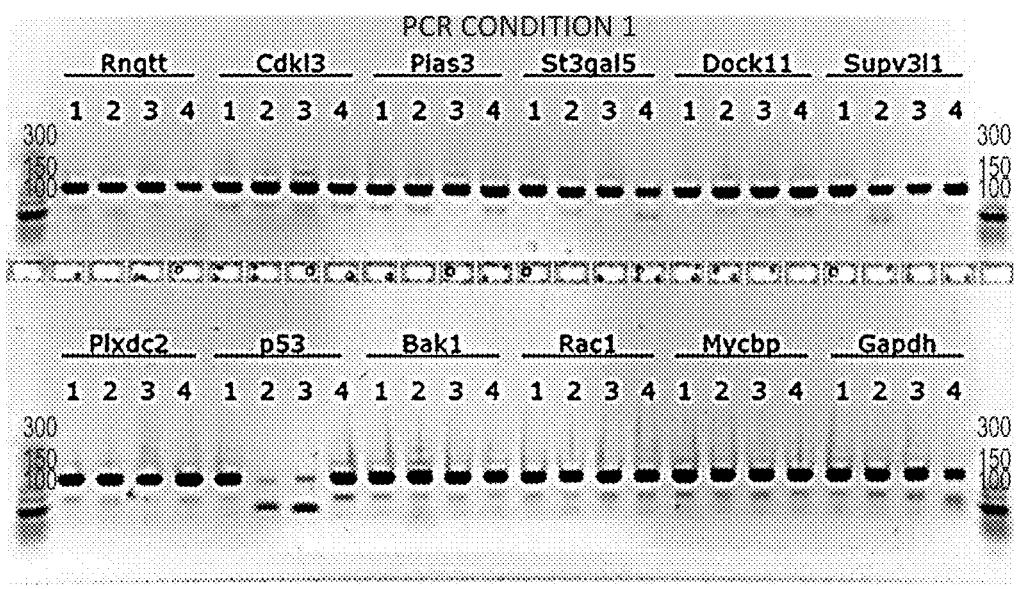
FIG. 15A1
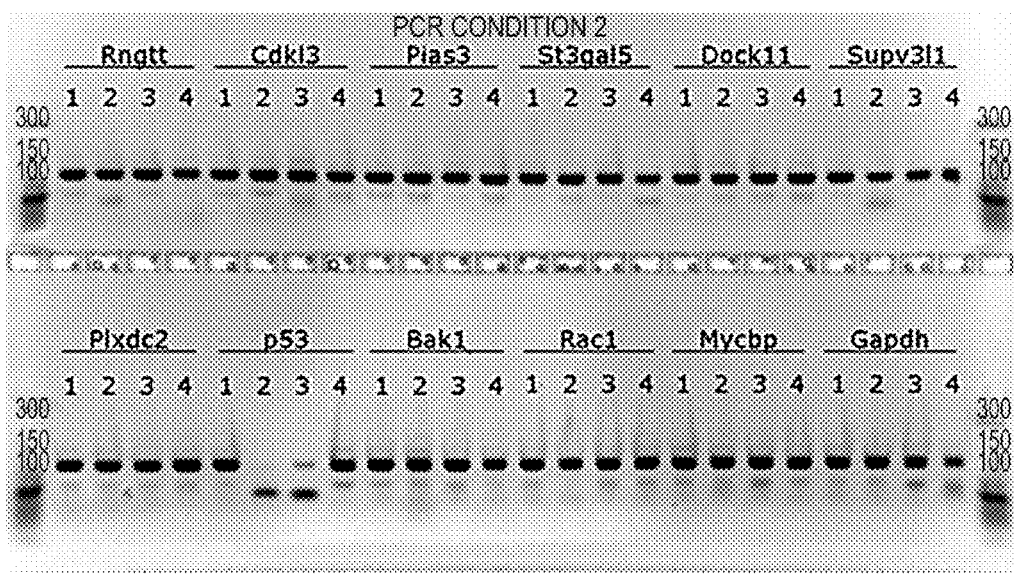
FIG. 15A2

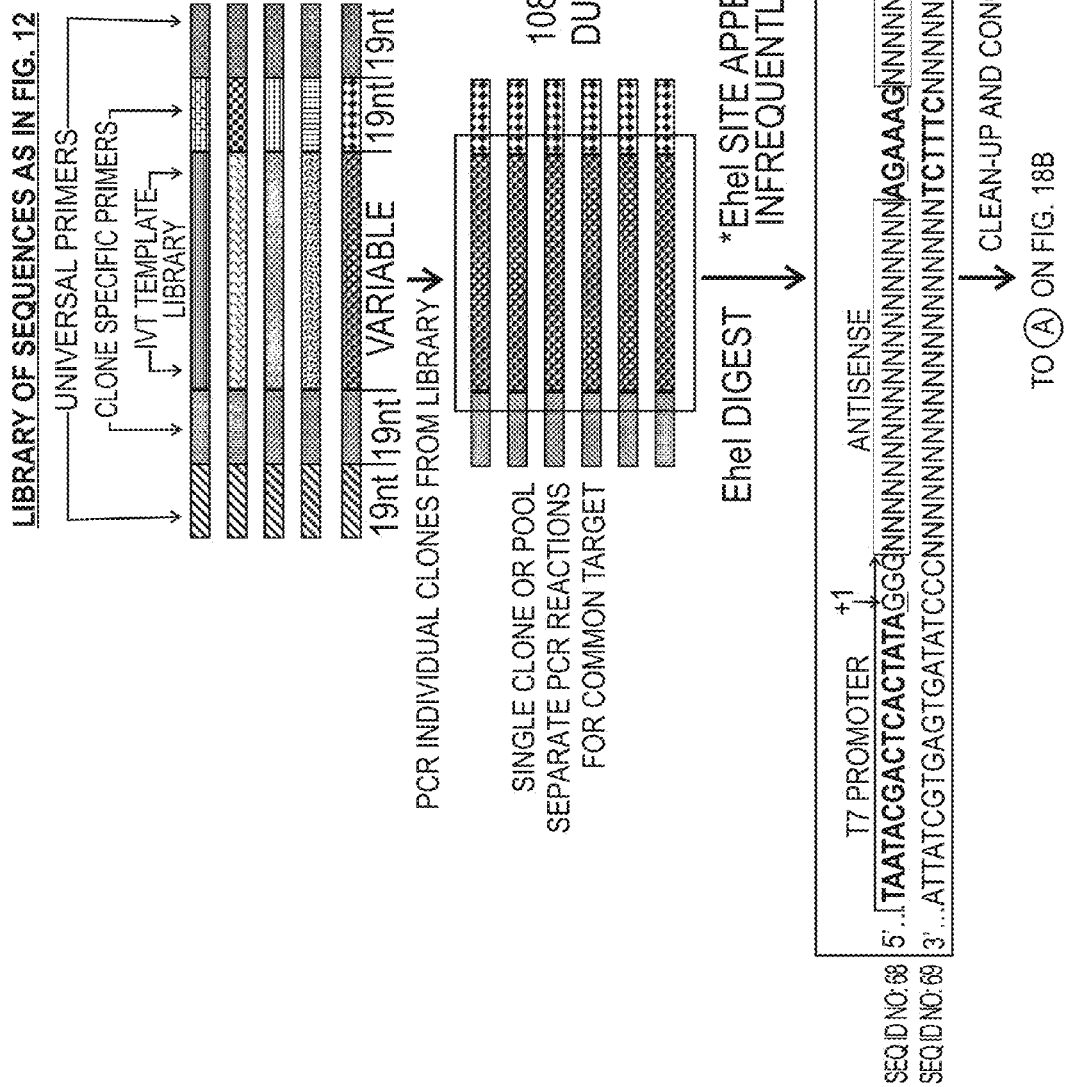

SEQUENCE LISTING

<160> NUMBER OF SEQ ID NOS: 82

<210> SEQ ID NO 1
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(17)
<223> OTHER INFORMATION: n is any of a, c, g or t
<220> FEATURE:
<221> NAME/KEY: misc_feature
<222> LOCATION: (23)..(41)
<223> OTHER INFORMATION: n is any of a, c, g or t
<220> FEATURE:
<221> NAME/KEY: misc_feature
<222> LOCATION: (44)..(45)
<223> OTHER INFORMATION: n is any of a, c, g or t

<400> SEQUENCE: 1
ctgaagnnnn nnnnngccg agnnnnnnnn nnnnnnnnnn nttnn    45

<210> SEQ ID NO 2
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is any of a, c, g or t
<220> FEATURE:
<221> NAME/KEY: misc_feature
<222> LOCATION: (5)..(23)
<223> OTHER INFORMATION: n is any of a, c, g or t
<220> FEATURE:
<221> NAME/KEY: misc_feature
<222> LOCATION: (30)..(39)
<223> OTHER INFORMATION: n is any of a, c, g or t

<400> SEQUENCE: 2
nnaannnnnn nnnnnnnnnn nnnctcggcn nnnnnnnnnc ttcag    45

<210> SEQ ID NO 3
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 3
nnnnnnnnnn nnnnnnnnnu u    21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 4
nnnnnnnnnn nnnnnnnnnc u                                           21

<210> SEQ ID NO 5
<211> LENGTH: 75
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(13)
<223> OTHER INFORMATION: n is any of a, c, g or t
<220> FEATURE:
<221> NAME/KEY: misc_feature
<222> LOCATION: (23)..(41)
<223> OTHER INFORMATION: n is any of a, c, g or t
<220> FEATURE:
<221> NAME/KEY: misc_feature
<222> LOCATION: (50)..(69)
<223> OTHER INFORMATION: n is any of a, c, g or t
<220> FEATURE:
<221> NAME/KEY: misc_feature
<222> LOCATION: (72)..(75)
<223> OTHER INFORMATION: n is any of a, c, g or t

<400> SEQUENCE: 5
ctgaagnnnn nnnggaaaaa aannnnnnnn nnnnnnnnnn nttagccgag nnnnnnnnnn    60
nnnnnnnnnt tnnnn                                                    75

<210> SEQ ID NO 6
<211> LENGTH: 75
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is any of a, c, g or t
<220> FEATURE:
<221> NAME/KEY: misc_feature
<222> LOCATION: (7)..(25)
<223> OTHER INFORMATION: n is any of a, c, g or t
<220> FEATURE:
<221> NAME/KEY: misc_feature
<222> LOCATION: (35)..(53)
<223> OTHER INFORMATION: n is any of a, c, g or t
<220> FEATURE:
<221> NAME/KEY: misc_feature
<222> LOCATION: (63)..(69)
<223> OTHER INFORMATION: n is any of a, c, g or t

<400> SEQUENCE: 6
nnnnaannnn nnnnnnnnnn nnnnnctcgg ctaannnnnn nnnnnnnnnn nnntttttt    60 ccnnnnnnnc ttcag                                                    75

<210> SEQ ID NO 7
<211> LENGTH: 49
<212> TYPE: DNA
<213> ORGANISM: Artificial Sequence
<220> FEATURE:
<223> OTHER INFORMATION: Synethic
<220> FEATURE:
<221> NAME/KEY: misc_feature
<222> LOCATION: (1)..(19)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

```
<400> SEQUENCE: 7
nnnnnnnnnn nnnnnnnnnt tagccgagnn nnnnnnnnnn nnnnnnntt                   49

<210> SEQ ID NO 8
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 8
nnnnnnnnnn nnnnnnnnnc tcggctaann nnnnnnnnnn nnnnnnntt                   49

<210> SEQ ID NO 9
<211> LENGTH: 49
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u
<220> FEATURE:
<221> NAME/KEY: misc_feature
<222> LOCATION: (29)..(47)
<223> OTHER INFORMATION: n is any of a, c, g or u

<400> SEQUENCE: 9
nnnnnnnnnn nnnnnnnnnu uagccgagnn nnnnnnnnnn nnnnnnnuu                   49

<210> SEQ ID NO 10
<211> LENGTH: 49
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u
<220> FEATURE:
<221> NAME/KEY: misc_feature
<222> LOCATION: (29)..(47)
<223> OTHER INFORMATION: n is any of a, c, g or u
<220> FEATURE:
<221> NAME/KEY: misc_feature
<222> LOCATION: (39)..(47)
<223> OTHER INFORMATION: n is any of a, c, g or u

<400> SEQUENCE: 10
nnnnnnnnnn nnnnnnnnnc ucggcuaann nnnnnnnnnn nnnnnnnuu                   49

<210> SEQ ID NO 11
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u
```

<400> SEQUENCE: 11
nnnnnnnnnn nnnnnnnnnu u                                         21

<210> SEQ ID NO 12
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 12
nnnnnnnnnn nnnnnnnnnu u                                         21

<210> SEQ ID NO 13
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 13
nnnnnnnnnn nnnnnnnnnc u                                         21

<210> SEQ ID NO 14
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 14
nnnnnnnnnn nnnnnnnnnu u                                         21

<210> SEQ ID NO 15
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(16)
<223> OTHER INFORMATION: n is any of a, c, g or t
<220> FEATURE:
<221> NAME/KEY: misc_feature
<222> LOCATION: (26)..(44)
<223> OTHER INFORMATION: n is any of a, c, g or t
<220> FEATURE:
<221> NAME/KEY: misc_feature
<222> LOCATION: (54)..(59)
<223> OTHER INFORMATION: n is any of a, c, g or t

<400> SEQUENCE: 15
ctgaagnnnn nnnnnggaa aaaaannnnn nnnnnnnnnn nnnnttttt tccnnnnnn     59

<210> SEQ ID NO 16

```
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
<223> OTHER INFORMATION: n is any of a, c, g or t
<220> FEATURE:
<221> NAME/KEY: misc_feature
<222> LOCATION: (16)..(34)
<223> OTHER INFORMATION: n is any of a, c, g or t
<220> FEATURE:
<221> NAME/KEY: misc_feature
<222> LOCATION: (44)..(53)
<223> OTHER INFORMATION: n is any of a, c, g or t

<400> SEQUENCE: 16
nnnnnnggaa aaaaannnnn nnnnnnnnnn nnnntttttt tccnnnnnnn nnncttcag         59

<210> SEQ ID NO 17
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: n is any of a, c, g or t

<400> SEQUENCE: 17
ggaaaaaaan nnnnnnnnnn nnnnnnnntt ttttcc                                 37

<210> SEQ ID NO 18
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: n is any of a, c, g or t

<400> SEQUENCE: 18
ggaaaaaaan nnnnnnnnnn nnnnnnnntt ttttcc                                 37

<210> SEQ ID NO 19
<211> LENGTH: 37
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: n is any of a, c, g or u

<400> SEQUENCE: 19
ggaaaaaaan nnnnnnnnnn nnnnnnnnuu uuuucc                                 37

<210> SEQ ID NO 20
<211> LENGTH: 37
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (10)..(28)
<223> OTHER INFORMATION: n is any of a, c, g or u

<400> SEQUENCE: 20
ggaaaaaaan nnnnnnnnnn nnnnnnnuu uuuuucc                        37

<210> SEQ ID NO 21
<211> LENGTH: 27
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(25)
<223> OTHER INFORMATION: n is any of a, c, g or u

<400> SEQUENCE: 21
aaaaaannnn nnnnnnnnn nnnnnuu                                   27

<210> SEQ ID NO 22
<211> LENGTH: 27
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 22
nnnnnnnnnn nnnnnnnnnu uuuuuc                                   27

<210> SEQ ID NO 23
<211> LENGTH: 26
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 23
nnnnnnnnnn nnnnnnnnnu uuuuu                                    26

<210> SEQ ID NO 24
<211> LENGTH: 26
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(24)
<223> OTHER INFORMATION: n is any of a, c, g or u

<400> SEQUENCE: 24 aaaaannnn nnnnnnnnnn nnnuu                                     26

<210> SEQ ID NO 25
<211> LENGTH: 26
<212> TYPE: RNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (5)..(23)
<223> OTHER INFORMATION: n is any of a, c, g or u

<400> SEQUENCE: 25 aaaannnnn nnnnnnnnnn nnnuuu                                    26

<210> SEQ ID NO 26
<211> LENGTH: 26
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is any of a, c, g or u

<400> SEQUENCE: 26
annnnnnnnn nnnnnnnnnn uuuuuu                                   26

<210> SEQ ID NO 27
<211> LENGTH: 25
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(21)
<223> OTHER INFORMATION: n is any of a, c, g or u

<400> SEQUENCE: 27
aannnnnnnn nnnnnnnnnn nuuuu                                    25

<210> SEQ ID NO 28
<211> LENGTH: 25
<212> TYPE: RNA
<213> ORGANISM: Homo sapiens
<220> FEATURE:
<221> NAME/KEY: misc_feature
<222> LOCATION: (3)..(21)
<223> OTHER INFORMATION: n is any of a, c, g or u

<400> SEQUENCE: 28
aannnnnnnn nnnnnnnnnn nuuuu                                    25

<210> SEQ ID NO 29
<211> LENGTH: 84
<212> TYPE: DNA
<213> ORGANISM: Homo sapiens
<220> FEATURE:
<221> NAME/KEY: misc_feature
<222> LOCATION: (7)..(16)
<223> OTHER INFORMATION: n is any of a, c, g or t
<220> FEATURE:
<221> NAME/KEY: misc_feature
<222> LOCATION: (32)..(50)
<223> OTHER INFORMATION: n is any of a, c, g or t
<220> FEATURE:
<221> NAME/KEY: misc_feature
<222> LOCATION: (60)..(78)
<223> OTHER INFORMATION: n is any of a, c, g or t
<220> FEATURE:
<221> NAME/KEY: misc_feature
<222> LOCATION: (81)..(84)
<223> OTHER INFORMATION: n is any of a, c, g or t

<400> SEQUENCE: 29
ctgaagnnnn nnnnntttta aaggaaaaaa annnnnnnnn nnnnnnnnnn ttagccgagn   60
```
nnnnnnnnnn nnnnnnnntt nnnn          84

<210> SEQ ID NO 30
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is any of a, c, g or t
<220> FEATURE:
<221> NAME/KEY: misc_feature
<222> LOCATION: (7)..(25)
<223> OTHER INFORMATION: n is any of a, c, g or t
<220> FEATURE:
<221> NAME/KEY: misc_feature
<222> LOCATION: (35)..(53)
<223> OTHER INFORMATION: n is any of a, c, g or t
<220> FEATURE:
<221> NAME/KEY: misc_feature
<222> LOCATION: (69)..(78)
<223> OTHER INFORMATION: n is any of a, c, g or t

<400> SEQUENCE: 30
nnnnaannnn nnnnnnnnnn nnnnnctcgg ctaannnnnn nnnnnnnnnn nnntttttt          60 cctttaaann nnnnnnnnct tcag          84

<210> SEQ ID NO 31
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: n is any of a, c, g or t
<220> FEATURE:
<221> NAME/KEY: misc_feature
<222> LOCATION: (38)..(56)
<223> OTHER INFORMATION: n is any of a, c, g or t

<400> SEQUENCE: 31
ggaaaaaaan nnnnnnnnnn nnnnnnnntt agccgagnnn nnnnnnnnnn nnnnnntt          58

<210> SEQ ID NO 32
<211> LENGTH: 58
<212> TYPE: DNA
<213> ORGANISM: Homo sapiens
<220> FEATURE:
<221> NAME/KEY: misc_feature
<222> LOCATION: (1)..(19)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 32
nnnnnnnnnn nnnnnnnnnc tcggctaann nnnnnnnnnn nnnnnnnttt ttttcctt          58

<210> SEQ ID NO 33
<211> LENGTH: 58
<212> TYPE: RNA
<213> ORGANISM: Artificial Sequence
<220> FEATURE:
<223> OTHER INFORMATION: Synthetic
<220> FEATURE:

<221> NAME/KEY: misc_feature
<222> LOCATION: (10)..(28)
<223> OTHER INFORMATION: n is any of a, c, g or u
<220> FEATURE:
<221> NAME/KEY: misc_feature
<222> LOCATION: (38)..(56)
<223> OTHER INFORMATION: n is any of a, c, g or u

<400> SEQUENCE: 33
ggaaaaaaan nnnnnnnnnn nnnnnnnuu agccgagnnn nnnnnnnnnn nnnnnnuu    58

<210> SEQ ID NO 34
<211> LENGTH: 58
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u
<220> FEATURE:
<221> NAME/KEY: misc_feature
<222> LOCATION: (29)..(47)
<223> OTHER INFORMATION: n is any of a, c, g or u

<400> SEQUENCE: 34
nnnnnnnnnn nnnnnnnnc ucggcuaann nnnnnnnnn nnnnnnnuuu uuuccuu    58

<210> SEQ ID NO 35
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(28)
<223> OTHER INFORMATION: n is any of a, c, g or u

<400> SEQUENCE: 35
ggaaaaaaan nnnnnnnnnn nnnnnnnuu    30

<210> SEQ ID NO 36
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 36
nnnnnnnnnn nnnnnnnnnu u    21

<210> SEQ ID NO 37
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 37
nnnnnnnnnn nnnnnnnnnc u    21

<210> SEQ ID NO 38
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 38
nnnnnnnnnn nnnnnnnnnu uuuuuuccuu                                30

<210> SEQ ID NO 39
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(45)
<223> OTHER INFORMATION: n is any of a, c, g or t
<220> FEATURE:
<221> NAME/KEY: misc_feature
<222> LOCATION: (55)..(73)
<223> OTHER INFORMATION: n is any of a, c, g or t
<220> FEATURE:
<221> NAME/KEY: misc_feature
<222> LOCATION: (76)..(79)
<223> OTHER INFORMATION: n is any of a, c, g or t

<400> SEQUENCE: 39
gggccctaat acgactcact atagggnnnn nnnnnnnnn nnnnttagc cgagnnnnnn        60 nnnnnnnnnn nnnttnnnn                                                   79

<210> SEQ ID NO 40
<211> LENGTH: 79
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is any of a, c, g or t
<220> FEATURE:
<221> NAME/KEY: misc_feature
<222> LOCATION: (7)..(25)
<223> OTHER INFORMATION: n is any of a, c, g or t
<220> FEATURE:
<221> NAME/KEY: misc_feature
<222> LOCATION: (35)..(53)
<223> OTHER INFORMATION: n is any of a, c, g or t

<400> SEQUENCE: 40
nnnnaannnn nnnnnnnnnn nnnnnctcgg ctaannnnnn nnnnnnnnnn nnncccctata     60 gtgagtgcta ttagggccc                                                   79

<210> SEQ ID NO 41
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(40)

```
<223> OTHER INFORMATION: n is any of a, c, g or t
<220> FEATURE:
<221> NAME/KEY: misc_feature
<222> LOCATION: (50)..(68)
<223> OTHER INFORMATION: n is any of a, c, g or t

<400> SEQUENCE: 41
ctaatacgac tcactatagg gnnnnnnnnn nnnnnnnnnn ttagccgagn nnnnnnnnn      60 nnnnnnnntt                                                           70

<210> SEQ ID NO 42
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 42
nnnnnnnnnn nnnnnnnnnc tcggctaann nnnnnnnnnn nnnnnnnccc tatagtgagt    60
gctattaggg cc                                                        72

<210> SEQ ID NO 43
<211> LENGTH: 52
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (32)..(50)
<223> OTHER INFORMATION: n is any of a, c, g or u

<400> SEQUENCE: 43
gggnnnnnnn nnnnnnnnnn nnuuagccga gnnnnnnnnn nnnnnnnnnn uu            52

<210> SEQ ID NO 44
<211> LENGTH: 52
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (32)..(50)
<223> OTHER INFORMATION: n is any of a, c, g or u

<400> SEQUENCE: 44
gggnnnnnnn nnnnnnnnnn nnuuagccga gnnnnnnnnn nnnnnnnnnn uu            52

<210> SEQ ID NO 45
<211> LENGTH: 52
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (32)..(50)
<223> OTHER INFORMATION: n is any of a, c, g or u

<400> SEQUENCE: 45
gggnnnnnnn nnnnnnnnnn nnuuagccga gnnnnnnnnn nnnnnnnnnn uu            52

<210> SEQ ID NO 46
<211> LENGTH: 52
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(21)
<223> OTHER INFORMATION: n is any of a, c, g or u
<220> FEATURE:
<221> NAME/KEY: misc_feature
<222> LOCATION: (31)..(49)
<223> OTHER INFORMATION: n is any of a, c, g or u

<400> SEQUENCE: 46
aannnnnnnn nnnnnnnnnn ncucggcuaa nnnnnnnnnn nnnnnnnnnc cc            52

<210> SEQ ID NO 47
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u

<400> SEQUENCE: 47
gggnnnnnnn nnnnnnnnnn nnuu                                          24

<210> SEQ ID NO 48
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 48
nnnnnnnnnn nnnnnnnnnu u                                             21

<210> SEQ ID NO 49
<211> LENGTH: 52
<212> TYPE: RNA
<213> ORGANISM: Homo sapiens
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (32)..(50)
```

```
<223> OTHER INFORMATION: n is any of a, c, g or u

<400> SEQUENCE: 49
gggnnnnnnn nnnnnnnnnn nnuuagccga gnnnnnnnnn nnnnnnnnnn uu          52

<210> SEQ ID NO 50
<211> LENGTH: 52
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(21)
<223> OTHER INFORMATION: n is any of a, c, g or u
<220> FEATURE:
<221> NAME/KEY: misc_feature
<222> LOCATION: (31)..(49)
<223> OTHER INFORMATION: n is any of a, c, g or u

<400> SEQUENCE: 50
aannnnnnnn nnnnnnnnnn ncucggcuaa nnnnnnnnnn nnnnnnnnnc cc          52

<210> SEQ ID NO 51
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u

<400> SEQUENCE: 51
gggnnnnnnn nnnnnnnnnn nnuu                                          24

<210> SEQ ID NO 52
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 52
nnnnnnnnnn nnnnnnnnnu u                                             21

<210> SEQ ID NO 53
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(21)
<223> OTHER INFORMATION: n is any of a, c, g or u

<400> SEQUENCE: 53
aannnnnnnn nnnnnnnnnn nuu                                           23

<210> SEQ ID NO 54
<211> LENGTH: 22
<212> TYPE: RNA
<213> ORGANISM: Artificial Sequence
```

<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 54
nnnnnnnnnn nnnnnnnnnc cc                                              22

<210> SEQ ID NO 55
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(45)
<223> OTHER INFORMATION: n is any of a, c, g or t
<220> FEATURE:
<221> NAME/KEY: misc_feature
<222> LOCATION: (52)..(54)
<223> OTHER INFORMATION: n is any of a, c, g or t

<400> SEQUENCE: 55
gggccctaat acgactcact atagggnnnn nnnnnnnnn nnnnntttaa annn            54

<210> SEQ ID NO 56
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is any of a, c, g or t
<220> FEATURE:
<221> NAME/KEY: misc_feature
<222> LOCATION: (10)..(28)
<223> OTHER INFORMATION: n is any of a, c, g or t

<400> SEQUENCE: 56
nnntttaaan nnnnnnnnn nnnnnnnncc ctatagtgag tgctattagg gccc            54

<210> SEQ ID NO 57
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(40)
<223> OTHER INFORMATION: n is any of a, c, g or t

<400> SEQUENCE: 57
ctaatacgac tcactatagg gnnnnnnnnn nnnnnnnnn ttt                        43

<210> SEQ ID NO 58
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or t

```
<400> SEQUENCE: 58
aaannnnnnn nnnnnnnnnn nnccctatag tgagtgctat tagggcc                    47

<210> SEQ ID NO 59
<211> LENGTH: 25
<212> TYPE: RNA
<213> ORGANISM: Homo sapiens
<220> FEATURE:
<221> NAME/KEY: misc_feature
<222> LOCATION: (4)..(22)
<223> OTHER INFORMATION: n is any of a, c, g or u

<400> SEQUENCE: 59
gggnnnnnnn nnnnnnnnnn nnuuu                                            25

<210> SEQ ID NO 60
<211> LENGTH: 25
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(22)
<223> OTHER INFORMATION: n is any of a, c, g or u

<400> SEQUENCE: 60
aaannnnnnn nnnnnnnnnn nnccc                                            25

<210> SEQ ID NO 61
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(39)
<223> OTHER INFORMATION: n is any of a, c, g or t
<220> FEATURE:
<221> NAME/KEY: misc_feature
<222> LOCATION: (46)..(64)
<223> OTHER INFORMATION: n is any of a, c, g or t

<400> SEQUENCE: 61
taatacgact cactataggg nnnnnnnnnn nnnnnnnnna gaaagnnnnn nnnnnnnnnn       60 nnnnggcgcc                                                             70

<210> SEQ ID NO 62
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(25)
<223> OTHER INFORMATION: n is any of a, c, g or t
<220> FEATURE:
<221> NAME/KEY: misc_feature
<222> LOCATION: (32)..(40)
<223> OTHER INFORMATION: n is any of a, c, g or t
<220> FEATURE:
<221> NAME/KEY: misc_feature
<222> LOCATION: (41)..(50)
<223> OTHER INFORMATION: n is a, c, g, or t

<400> SEQUENCE: 62
ggcgccnnnn nnnnnnnnnn nnnnnctttc tnnnnnnnnn nnnnnnnnnn ccctatagtg       60
```
agtgctatta 70

<210> SEQ ID NO 63
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(39)
<223> OTHER INFORMATION: n is any of a, c, g or t
<220> FEATURE:
<221> NAME/KEY: misc_feature
<222> LOCATION: (46)..(64)
<223> OTHER INFORMATION: n is any of a, c, g or t

<400> SEQUENCE: 63
taatacgact cactataggg nnnnnnnnnn nnnnnnnnna gaaagnnnnn nnnnnnnnn 60 nnnnggc 67

<210> SEQ ID NO 64
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 64
gccnnnnnnn nnnnnnnnnn nnctttctnn nnnnnnnnnn nnnnnnnccc tatagtgagt 60
gctatta 67

<210> SEQ ID NO 65
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (29)..(47)
<223> OTHER INFORMATION: n is any of a, c, g or u

<400> SEQUENCE: 65
gggnnnnnnn nnnnnnnnnn nnagaaagnn nnnnnnnnnn nnnnnnggc 50

<210> SEQ ID NO 66
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 66
nnnnnnnnnn nnnnnnnnna g                                              21

<210> SEQ ID NO 67
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 67
nnnnnnnnnn nnnnnnnnng                                                20

<210> SEQ ID NO 68
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(39)
<223> OTHER INFORMATION: n is any of a, c, g or t
<220> FEATURE:
<221> NAME/KEY: misc_feature
<222> LOCATION: (46)..(64)
<223> OTHER INFORMATION: n is any of a, c, g or t

<400> SEQUENCE: 68
taatacgact cactataggg nnnnnnnnnn nnnnnnnna gaaagnnnnn nnnnnnnnnn       60 nnnnggc                                                              67

<210> SEQ ID NO 69
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 69
gccnnnnnnn nnnnnnnnnn nnctttctnn nnnnnnnnnn nnnnnnnccc tatagtgagt     60
gctatta                                                              67

<210> SEQ ID NO 70
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(39)
<223> OTHER INFORMATION: n is any of a, c, g or t
<220> FEATURE:
<221> NAME/KEY: misc_feature
<222> LOCATION: (46)..(64)
<223> OTHER INFORMATION: n is any of a, c, g or t

<400> SEQUENCE: 70
taatacgact cactataggg nnnnnnnnnn nnnnnnnna gaaagnnnnn nnnnnnnnnn    60 nnnnggc    67

<210> SEQ ID NO 71
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or t
<220> FEATURE:
<221> NAME/KEY: misc_feature
<222> LOCATION: (29)..(47)
<223> OTHER INFORMATION: n is any of a, c, g or t

<400> SEQUENCE: 71
gccnnnnnnn nnnnnnnnnn nnctttctnn nnnnnnnnnn nnnnnnnccc tatagtgagt    60
gcta    64

<210> SEQ ID NO 72
<211> LENGTH: 50
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(22)
<223> OTHER INFORMATION: n is any of a, c, g or u
<220> FEATURE:
<221> NAME/KEY: misc_feature
<222> LOCATION: (29)..(47)
<223> OTHER INFORMATION: n is any of a, c, g or u

<400> SEQUENCE: 72
gggnnnnnnn nnnnnnnnnn nnagaaagnn nnnnnnnnnn nnnnnnnggc    50

<210> SEQ ID NO 73
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 73
nnnnnnnnnn nnnnnnnnna g    21

<210> SEQ ID NO 74
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is any of a, c, g or u

<400> SEQUENCE: 74
nnnnnnnnnn nnnnnnnng								20

<210> SEQ ID NO 75
<211> LENGTH: 26
<212> TYPE: PRT
<213> ORGANISM: Artificial Sequence
<220> FEATURE:
<223> OTHER INFORMATION: Synthetic

<400> SEQUENCE: 75

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Glu Glu Glu Glu Glu Glu
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Asp Tyr Lys Asp Asp Asp Asp Lys
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Tyr Pro Tyr Asp Val Pro Asp Tyr Ala
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic

<400> SEQUENCE: 79

His His His His His His
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

```
Glu Gln Lys Leu Ile Ser Glu Glu Asp Leu
1               5                   10

<210> SEQ ID NO 81
<211> LENGTH: 16
<212> TYPE: PRT
<213> ORGANISM: Artificial Sequence
<220> FEATURE:
<223> OTHER INFORMATION: Synthetic

<400> SEQUENCE: 81

Thr Asp Lys Asp Met Thr Ile Thr Phe Thr Asn Lys Lys Asp Ala Glu
1               5                   10                  15

<210> SEQ ID NO 82
<211> LENGTH: 13
<212> TYPE: PRT
<213> ORGANISM: Artificial Sequence
<220> FEATURE:
<223> OTHER INFORMATION: Synthetic

<400> SEQUENCE: 82

Ala His Ile Val Met Val Asp Ala Tyr Lys Pro Thr Lys
1               5                   10
```

TEMPLATES, LIBRARIES, KITS AND METHODS FOR GENERATING MOLECULES

FIELD OF INVENTION

This application is a national stage application of PCT/US2015/010428, filed Jan. 7, 2014, which claims the benefit of the filing date of Provisional Application No. 61/751,157, filed Jan. 10, 2013. The entire disclosures of the aforementioned patent applications are hereby incorporated by reference into the present disclosure.

BACKGROUND OF THE INVENTION

The biotechnology industry makes advances by gaining an increased understanding of known molecules, identifying new molecules and exposing both known and new molecules to different environments. When striving to make these advances, one rate limiting step is the ability by which to obtain molecules of interest.

By way of example, the rate of advances in RNA interference ("RNAi") has in part been affected by the ability to obtain molecules of interest both efficiently and cost-effectively. The molecules of interest in this field are most often double stranded ribonucleic acids ("dsRNAs"). In mammalian systems, because long dsRNAs will induce a cellular stress response, thereby preventing targeted gene-silencing, typically researchers prefer to work with short interfering ribonucleic acids ("siRNAs," also known as "small interfering ribonucleic acids"), which are double stranded, but are of a limited size.

siRNAs may be formed either from two separate oligonucleotide strands that anneal or from a single stranded oligonucleotide that forms a hairpin. In either case, preferably there is a duplex region over which each strand is 18-30 nucleotides long. This duplex region, when exposed to endogenous mammalian cellular machinery, causes silencing of one or more genes that contain a sequence that is complementary to the antisense region of the siRNA.

As the use of siRNA has become more common, so too has the desire to generate both genome wide and unique collections of siRNA molecules. Unfortunately, siRNA synthesis is expensive. In order for manufacturers to generate siRNA molecules economically, they need to make them on a large scale. However, most researchers do not require large quantities of siRNA molecules. Therefore, often only a small fraction of what is produced for a particular siRNA duplex or sequence is sold to an individual customer. The remaining siRNA molecules, those beyond what a customer orders, must be stored cold, which presents a considerable burden for the manufacturer with respect to all unsold product. A similar challenge is presented when seeking to obtain other types of molecules for other applications.

Accordingly, there is a need to be able to store libraries of templates for oligonucleotides and to generate selected molecules of interest cost-effectively from these libraries. Various embodiments of the present invention are directed to this need.

SUMMARY OF THE INVENTION

The present invention is directed to templates, libraries and kits as well as methods for utilizing molecules derived from these templates, libraries and kits that directly or indirectly affect or measure: the activity or the presence of target genes or other oligonucleotides; the activity of proteins; the synthesis of oligonucleotides; or the activity within one or more pathways. The molecules may each comprise, consist essentially of or consist of a sequence of interest.

A collection of sequences of interest may be used to form a library that may, for example, correspond to a genomic collection of a type of molecule, e.g., a genomic collection of RNAi molecules. A genomic collection of RNAi molecules may be defined as a set of RNA molecules that target a plurality of different genes of an organism, e.g., all genes. Alternatively, one may form a library that contains RNAi molecules, such as siRNA molecules, that target a minimum number of genes, for example, in excess of 500 genes, in excess of 1000 genes, in excess of 5000 genes, in excess of 10,000 genes or in excess of 20,000 genes. Within a library that corresponds to RNAi molecules, for each gene targeted, there may be one, or at least two, or at least four or at least ten sequences per target. From these libraries, one can select sequences for applications, amplify specific sequences efficiently and isolate specific molecules and/or create desired sets of molecules. Libraries can be constructed for collections of many types of molecules, including but not limited to siRNA, shRNA, miRNA, miRNA inhibitors, lncRNA, antisense RNA, sgRNA, aptamers and ribozymes.

According to a first embodiment, the present invention provides a library of DNA molecules, wherein the library consists of, consists essentially of or comprises a plurality of DNA molecules, wherein each DNA molecule comprises, consists essentially of or consists of a sequence of interest located between a forward primer binding region and a reverse primer binding region, wherein for each DNA molecule the combination of the forward primer binding region and the reverse primer binding region is uniquely associated with the sequence of interest and within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region, wherein the forward primer binding region of the first subset is distinct from the forward primer binding region of the second subset.

According to a second embodiment, the present invention provides a library of DNA molecules, wherein the library comprises at least 100 DNA molecules, wherein each DNA molecule comprises a sequence of interest that corresponds to a peptide sequence and that is located between a forward primer binding region and a reverse primer binding region, wherein for each DNA molecule the combination of the forward primer binding region and the reverse primer binding region is uniquely associated with the sequence of interest and within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region. In this embodiment, the forward primer binding region that is shared by a plurality of DNA molecules that form the first subset is different from the forward primer binding region that is shared by a plurality of DNA molecules that form the second subset.

According to a third embodiment, the present invention provides a method for modular gene assembly, wherein the method comprises, consists essentially of or consists of: (a) accessing a library of DNA molecules, wherein the library comprises a plurality of DNA molecules, wherein each DNA molecule comprises a sequence of interest that corresponds to a fragment of a coding region of a gene and the sequence of interest is located between a forward primer binding region and a reverse primer binding region, wherein for each DNA molecule the combination of the forward primer binding region and the reverse primer binding region is uniquely associated with the sequence of interest and within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region and each DNA molecule has a first restriction site that is on one side of the sequence of interest and a second restriction site that is on the other side of the sequence of interest; (b) in separate environments, exposing each of a plurality of sets of primer pairs that are uniquely associated with DNA molecules of interest to a copy of the library under conditions that permit amplification to generate amplified DNA molecules of interest; (c) removing flanking primer binding sites; and (d) ligating two or more DNA molecules of interest from which flanking primer binding sites have been removed to form a modular gene.

According to a fourth embodiment, the present invention provides a method for generating an expression unit, wherein the method comprises, consists essentially of or consists of: (a) accessing a library of DNA molecules, wherein the library comprises a set of DNA molecules, wherein the set of DNA molecules comprises (i) a plurality of type I DNA molecules, wherein each type I DNA molecule comprises a sequence of interest that corresponds to a promoter region; (ii) a plurality of type II DNA molecules, wherein each type II DNA molecule comprises a sequence of interest that corresponds to a 5' regulatory region; (iii) a plurality of type III DNA molecules, wherein each type III DNA molecule comprises a sequence of interest that corresponds to a protein coding region or a fragment thereof; and (iv) a plurality of type IV DNA molecules, wherein each type IV DNA molecule comprises a sequence of interest that corresponds to a 3' regulatory region; wherein each sequence of interest is located between a forward primer binding region and a reverse primer binding region, wherein for each DNA molecule the combination of the forward primer binding region and the reverse primer binding region is uniquely associated with the sequence of interest and within a first subset of the set of DNA molecules, each of a plurality of DNA molecules has the same forward primer binding region and a different reverse primer binding region and within a second subset of the set of DNA molecules, each of a plurality of DNA molecules has the same forward primer binding region and a different reverse primer binding region and wherein each DNA molecule has a first restriction site that is on one side of the sequence of interest and a second restriction site that is on the other side of the sequence of interest; (b) in separate environments under conditions that permit PCR, (i) exposing the library, or a copy thereof, to a first primer pair that is uniquely associated with a type I DNA molecule of interest; (ii) exposing the library, or a copy thereof, to a second primer pair that is uniquely associated with a type II DNA molecule of interest; (iii) exposing the library, or a copy thereof, to a third primer pair that is uniquely associated with a type III DNA molecule of interest; and (iv) exposing the library, or a copy thereof, to a fourth primer pair that is uniquely associated with a type IV DNA molecule of interest, thereby amplifying the type I DNA molecule of interest, the type II DNA molecule of interest, the type III DNA molecule of interest, and the type IV DNA molecule of interest; (c) removing flanking primer binding sites from each DNA molecule of interest; and (d) ligating together the type I DNA molecule of interest, the type II DNA molecule of interest, the type III DNA molecule of interest, and the type IV DNA molecule of interest to generate an expression unit. As persons of ordinary skill in the art will recognize, each of the types of DNA molecules may be stored in separate containers or a plurality or all of the different types may be stored in the same container. Furthermore, in some embodiments, one uses primer pairs for a plurality of type III DNA molecules to generate a modular gene of interest and ligates the modular gene comprising the type III DNA molecules of interest with a type I DNA molecule of interest, a type II DNA molecule of interest and a type DNA IV molecule of interest.

According to a fifth embodiment, the present invention provides a method for generating an aptamer, said method comprising, consisting essentially of or consisting of: (a) accessing a library of DNA molecules, wherein each DNA molecule comprises a sequence of interest that corresponds to an aptamer and the sequence of interest is located between a forward primer binding region and a reverse primer binding region, wherein for each DNA molecule the combination of the forward primer binding region and the reverse primer binding region is uniquely associated with the sequence of interest and within a first subset of the library of DNA molecules, each of a plurality of DNA molecules has the same forward primer binding region and a different reverse primer binding region and within a second subset of the library of DNA molecules, each of a plurality of DNA molecules has the same forward primer binding region and a different reverse primer binding region and each DNA molecule has a first restriction site that is on one side of the sequence of interest and a second restriction site that is on the other side of the sequence of interest; (b) exposing the library, or a copy thereof, to a primer pair that is uniquely associated with a DNA molecule of interest; (c) amplifying the DNA molecule of interest under conditions conducive for PCR; (d) removing flanking primer binding sites to generate an amplified DNA molecule; and (e) using the amplified DNA molecule to generate an aptamer.

According to a sixth embodiment, the present invention provides a method for DNA fabrication, the method comprising: (a) accessing a library of DNA molecules, wherein the library of DNA molecules, comprises a first group of DNA molecules and a second group of DNA molecules, wherein each of the DNA molecules within the first group comprises a sequence of interest that corresponds to an aptamer and each of the DNA molecules within the second group comprises a sequence of interest that corresponds to a scaffolding element, wherein in each DNA molecule, the sequence of interest is located between a forward primer binding region and a reverse primer binding region, wherein for each DNA molecule the combination of the forward primer binding region and the reverse primer binding region is uniquely associated with the sequence of interest and within a first subset of the library of DNA molecules, each of a plurality of DNA molecules has the same forward primer binding region and a different reverse primer binding region and within a second subset of the library of DNA molecules, each of a plurality of DNA molecules has the same forward primer binding region and a different reverse primer binding region and each DNA molecule has a first restriction site that is on one side of the sequence of interest and a second restriction site that is on the other side of the sequence of interest; (b) in a first environment, exposing the library, or a copy thereof, to a first primer pair that is uniquely associated with a DNA molecule from the first group under conditions conducive for PCR to generate a first product; (c) in a second environment, exposing the library, or a copy thereof, to a second primer pair that is uniquely associated with a DNA molecule from the second group under conditions conducive for PCR to generate a second product; and (d) linking the first product to the second product. In this embodiment, unless otherwise specified, the use of the term "subset" is intended to describe the distribution of primer binding regions, and molecules from different subsets may be within the same physical container. Additionally, molecules from the two groups may be contained in the same container as part of the same mixture or solution, or they may be located in different containers.

According to a seventh embodiment, the present invention provides a method for generating sgRNA, the method comprising, consisting of or consisting essentially of: (a) accessing a library of DNA molecules, wherein the library comprises a first group of DNA molecules and a second group of DNA molecules, wherein each DNA molecule within the first group comprises a sequence of interest that corresponds to a crRNA (Clustered Regularly Interspaced Short Palindromic Repeats ("CRISPR") RNA) sequence and each DNA molecule within the second group comprises a sequence of interest that corresponds to a tracrRNA (trans-activating crRNA) sequence, wherein in each DNA molecule, the sequence of interest is located between a forward primer binding region and a reverse primer binding region, wherein for each DNA molecule the combination of the forward primer binding region and the reverse primer binding region is uniquely associated with the sequence of interest and within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region and each DNA molecule in the library has a first restriction site that is on one side of the sequence of interest and a second restriction site that is on the other side of the sequence of interest; (b) in a first environment, exposing the library, or a copy thereof, to a first primer pair that is uniquely associated with a DNA molecule from the first group under conditions conducive for PCR to generate a first product; (c) in a second environment, exposing the library, or a copy thereof, to a second primer pair that is uniquely associated with a DNA molecule from the second group under conditions conducive for PCR to generate a second product; and (d) linking the first product to the second product. As with the previous embodiment, in this embodiment, unless otherwise specified, the use of the term "subset" is intended to describe the distribution of primer binding regions, and molecules from different subsets may be within the same physical container. Additionally, molecules from the two groups may be contained in the same container as part of the same mixture or solution, or they may be located in different containers.

According to an eighth embodiment, the present invention provides a method for generating one or more RNAi molecules, said method comprising, consisting essentially of or consisting of: (a) isolating and amplifying one or more molecular clones from an oligonucleotide library, wherein the oligonucleotide library comprises a plurality of dsDNA oligonucleotides, wherein each dsDNA oligonucleotide comprises, consists essentially of or consists of the following elements: a first region, a sequence of interest and a second region, wherein each sequence of interest comprises a DNA sequence that corresponds to a region of a target and is located between the first region and the second region, the first region is defined by a first sequence and the second region is defined by a second sequence, wherein within each dsDNA oligonucleotide, the first sequence and the second sequence are distinct from each other and the first sequence and the second sequence are at least 50% dissimilar from a region adjacent to said region of said target, to form a set of one or more isolated and amplified molecular clones, wherein the set of one or more isolated and amplified molecular clones contains clones of fewer than all of the plurality of dsDNA oligonucleotides; and (b) either: (1) (i) cloning the set of one or more isolated and amplified molecular clones into one or more plasmids, (ii) expressing the set of one or more isolated and amplified molecular clones from within the one or more plasmids to form one or more expression products, and (iii) cloning the one or more expression products through either restriction digestion cloning or assembly cloning to obtain one or more RNAi molecules, or (2) enzymatically generating one or more RNAi molecules from the one or more isolated and amplified clones, wherein the first region of each dsDNA oligonucleotide comprises a first universal primer binding region and the second region of each dsDNA oligonucleotide comprises a second universal primer binding region, wherein the first universal primer binding region is the same for all of the plurality of dsDNA oligonucleotides and the second universal primer binding region is the same for all of the plurality of dsDNA oligonucleotides and at least one of the following conditions exists: (i) the first sequence comprises a first identifier region that is unique for each dsDNA oligonucleotide that contains a unique sequence of interest; (ii) the second sequence comprises a second identifier region that is unique for each dsDNA oligonucleotide that contains a unique sequence of interest; or (iii) the combination of the first identifier region and the second identifier region is unique for each dsDNA oligonucleotide that contains a unique sequence of interest.

According to a ninth embodiment, the present invention provides a kit comprising, consisting essentially of or consisting of: (a) a pool of dsDNA oligonucleotides within a first compartment, wherein the pool comprises a plurality of dsDNA oligonucleotides, wherein each dsDNA oligonucleotide comprises a first region, a sequence of interest and a second region, wherein the sequence of interest is located between the first region and the second region, and the sequence of interest comprises a DNA sequence that corresponds to a region of a target RNA, wherein the first region is defined by a first sequence and the second region is defined by a second sequence, wherein the first sequence and the second sequence are distinct from each other and each of the first sequence and the second sequence are at least 50% dissimilar from a region adjacent to said region of said target RNA and at least one of the following conditions exists: (i) the first sequence is unique for each dsDNA oligonucleotide that contains a unique sequence of interest; (ii) the second sequence is unique for each dsDNA oligonucleotide that contains a unique sequence of interest; or (iii) the combination of the first sequence and the second sequence is unique for each dsDNA oligonucleotide that contains a unique sequence of interest; (b) a first set of primers within a second compartment, wherein the first set of primers comprises a first primer that corresponds to a subsequence within the first region of a first subset of dsDNA oligonucleotides and a second primer that corresponds to a subsequence within the second primer binding region of the first subset of dsDNA oligonucleotides; and (c) a second set of primers within a third compartment, wherein the second set of primers comprises a first primer that corresponds to a subsequence within the first region of a second subset of dsDNA oligonucleotides and a second primer that corresponds to a subsequence within the second region of the second subset of dsDNA oligonucleotides, wherein the first primer within the second compartment and the first primer within the third compartment are distinct from each other. Optionally, the second primer within the second compartment and the second primer within the third compartment are also distinct from each other. Two primers are distinct if they contain no more than 10, no more than 9, no more than 8, or no more than 7 of the same bases at the same location under conditions of maximal alignment.

Various embodiments of the present invention take advantage of the greater stability of DNA relative to RNA while still being beneficial for use in connection with generating selected molecules. Thus, one may store thousands or tens of thousands of specific sequences within one tube or container, thereby reducing the burden of storage. For example, in some embodiments, entire genomes worth of knockdown sequences can be stored in a few tubes, and when a particular molecule such as an siRNA is desired, it can be synthesized enzymatically from the library on demand. This allows reduction of inventory of unsold siRNAs and allows for the provision of siRNAs that correspond to any gene in any organism on demand. Accordingly, a person of ordinary skill in the art may store an indexed library of sequences for RNAi molecules as DNA and then rapidly convert selected sequences into RNAi molecules. Similar benefits may be realized with respect to other types of molecules, and the molecules that are generated may be used in various applications or combined with other molecules that are used in various applications.

BRIEF DESCRIPTION OF THE FIGURES

FIGS. 8A and 8B combine to form a representation of a strategy for generating dsRNAs that are 25-27 nucleotides long from dsDNA.

FIGS. 10A and 10B combine to form a representation of another strategy for generating shRNA and/or siRNA.

FIG. 14 is a representation of the use of specific combinations of subset and identification primers to yield PCR amplicons.

FIGS. 15A1, 15A2 and 15B are representations of the results of a combinatorial PCR strategy to amplify specific targets preferentially. FIGS. 15A1 and 15A2 provide four gels. FIG. 15B is a bar chart that shows the percent of reads that align and the number of millions of reads.

FIGS. 18A and 18B combine to provide a general workflow for producing siRNAs from DNA templates for an embodiment of the present invention.

DETAILED DESCRIPTION

Figure 1:
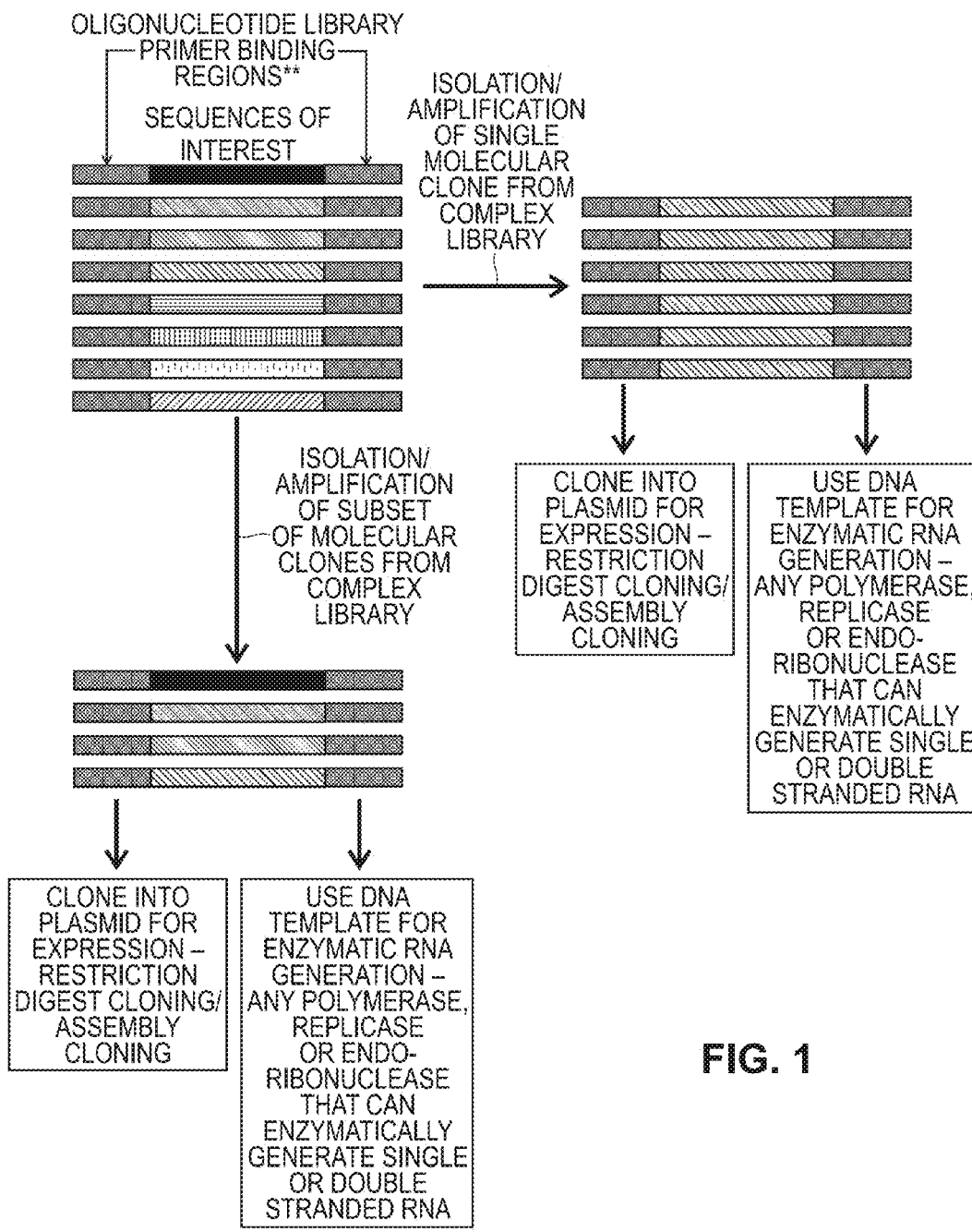
FIG. 1 is a representation of a general strategy for isolating a specific sequence or subsets of sequences from a complex oligonucleotide library using unique primer combinations.

The present invention provides templates, libraries, and kits for generating molecules such as siRNAs, shRNAs, miRNA mimics, miRNA inhibitors, antisense molecules, peptides, aptamers, sgRNAs and lncRNA molecules, and methods for selectively obtaining these molecules. By storing an indexed library of molecules as DNA, selectively amplifying DNA, and then generating other molecules from the amplified DNA, one can efficiently reduce costs associated with the storage of templates for these libraries, while allowing for efficient retrieval of desired molecules.

Throughout this disclosure and in the figures, the molecules that are generated are at times described as siRNA and/or shRNA molecules. However, as persons of ordinary skill in the art will recognize, in both the disclosure and the figures, siRNA and shRNA molecules are examples, and unless otherwise specific or implicit from context, the same techniques can be applied to any other type of small RNA molecule, including but not limited to miRNA mimics, miRNA inhibitors or any other known or not yet defined RNA molecules, e.g., any RNA between 10 and 500 nucleotides (or base pairs) in length or between 15 and 150 nucleotides (or base pairs) in length or between 18 and 50 nucleotides (or base pairs) in length or between 20 and 30 nucleotides (or base pairs) in length, as well as to other polynucleotides of those sizes and polynucleotides of those sizes that correspond to polypeptides. In some embodiments, each sequence of interest corresponds to a region of transcribed RNA such as an mRNA.

According to a first embodiment, the present invention is directed to a library of DNA molecules. The totality of molecules within a library may be referred to as a set of DNA molecules. Thus, the library comprises a plurality of DNA molecules. Each DNA molecule comprises, consists essentially of or consists of a sequence of interest located between a forward primer binding region and a reverse primer binding region. In some embodiments, for each DNA molecule, the combination of the forward primer binding region and the reverse primer binding region is uniquely associated with the sequence of interest. Thus, a unique combination of a forward primer that corresponds to the forward primer binding region and a reverse primer that corresponds to the reverse primer binding region may be used to obtain a DNA molecule of interest from the library.

Within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region. Optionally, within a third subset of DNA molecules, each of a plurality of DNA molecules has the same reverse primer binding region and a different forward primer binding region, and within a fourth subset of DNA molecules, each of a plurality of DNA molecules has the same reverse primer binding region and a different forward primer binding region. A first DNA molecule may be part of both the first and third subsets and a second DNA molecule may be part of the second and fourth subsets.

As persons of ordinary skill in the art will recognize, within a particular unique primer pair there is a forward primer and a reverse primer. The forward primer may correspond to a forward primer binding region within a first plurality of DNA molecules and the reverse primer may correspond to a reverse primer binding region within a second plurality of DNA molecules, but in these embodiments, only one DNA molecule contains the two primer binding regions that correspond to the forward primer and the reverse primer. Thus, within a library, there may be a plurality of subsets of DNA molecules, wherein each subset is defined by either a common forward primer binding region or a common reverse primer binding region, but not both. Consequently, one or more, e.g., each of at least 2, at least 3, at least 5, at least 10, at least 20, at least 50, at least 100, at least 200 or at least 500 DNA molecules within the library is part of a subset that contains a plurality of DNA molecules that have the same forward primer binding region, but not the same reverse primer binding region. Additionally, each of at least 2, at least 3, at least 5, at least 10, at least 20, at least 50, at least 100, at least 200 or at least 500 DNA molecules within the library may be part of another subset that contains plurality of DNA molecules that have the same reverse primer binding region, but not the same forward primer binding region. Thus, each of n forward primers may form unique combinations with each of m reverse primers, wherein e.g., n=1 to 1000 or 5 to 500 or 10 to 100 and m=1 to 1000 or 5 to 500 or 10 to 100 and each unique combination of primers may be associated with a different sequence of interest in the DNA molecules, thereby allowing for n×m subsets. Accordingly, a particular DNA molecule may be part of two subsets, one defined by the commonality of the forward primer binding region and the other defined by the commonality of the reverse primer binding region.

Although libraries may be designed such that an individual forward primer or individual reverse primer alone is unique to a sequence of interest, preferably less than 50%, or less than 40% or less than 30% or less than 20% or less than 10% or less than 5% or less than 2% of less than 1% or less than 0.5% or none of the unique sequences of interest are associated with a forward primer binding region that is not associated with at least one other sequence of interest or a reverse primer binding region that is not associated with at least one other sequence of interest. Throughout this disclosure, unless otherwise specified or apparent from context, the use of the term "subset" is intended to describe common elements, e.g., common primer binding regions, and molecules from different subsets may be contained in the same container as part of the same mixture or solution or they may be located in different containers.

The DNA molecules within the library may, for example, comprise, consist essentially of or consist of dsDNA oligonucleotides that each contain sequences that correspond to one or more regions of a molecule of interest. These sequences within the dsDNA may be referred to as "sequences of interest." As persons of ordinary skill in the art will recognize, in a ssDNA molecule or dsDNA molecule all T nitrogenous bases correspond to U nitrogenous bases within corresponding RNA.

By way of non-limiting examples, the library may comprise at least 50 dsDNA oligonucleotides, at least 100 dsDNA oligonucleotides, at least 500 dsDNA oligonucleotides, at least 1000 dsDNA oligonucleotides, at least 5000 dsDNA oligonucleotides, at least 10,000 dsDNA oligonucleotides, at least 50,000 dsDNA oligonucleotides, at least 100,000 dsDNA oligonucleotides, at least 500,000 dsDNA oligonucleotides, at least 1,000,000 dsDNA oligonucleotides, or at least 5,000,000 dsDNA oligonucleotides, etc. The library may be organized such that within a single container there may be over 100, over 200, over 500, over 1000, over 1200, over 1500, over 2000 or between 100 and 3000, between 500 and 2000 or between 1000 and 1500 DNA molecules. Thus, particularly large libraries may be stored in a plurality of containers.

Each of the DNA oligonucleotides may differ by both their pair of primer binding regions and their sequences of interest. Each sequence of interest may, for example, be 15-500, 15-150, 150-500, 18-36, 18-30, 20-25 or 20-23 nucleotides long. Two sequences of interest are considered to be different from each other if they differ in whole or in part, including but not limited to by corresponding to regions of different targets or to different regions of the same target that partially overlap or that do not overlap or by corresponding to the same region of the same target but are different lengths such that one sequence of interest is a subsequence of another sequence of interest, or are identical in length and sequence except for the identity of one or more bases at one or more locations. As persons of ordinary skill in the art will recognize, by having sequences of interest that differ by one or more bases, a library can contain both wild-type and variant molecules, e.g., SNPs (single-nucleotide polymorphisms) relative to each other.

By way of a further non-limiting example, when a library contains dsDNA oligonucleotides that contain sequences that correspond to fewer than all siRNA for a species, the library may, for example, include one or more sequences that correspond to at least 25%, at least 50%, at least 75%, at least 80%, at least 90% or all of the known mRNA of a species.

In some embodiments, the library comprises at least 10, at least 50, at least 100, at least 500, at least 1000, at least 5000, at least 10,000, or at least 20,000 dsDNA oligonucleotides that have sequences of interest that correspond to different genes. The target sequences may, for example, be RNA sequences such as transcribed RNA sequences or subsequences of those transcribed RNA sequences. In some embodiments, the target sequences are coding regions of mRNA sequences for a particular species. In some embodiments, for each of at least 10, at least 50, at least 100, at least 500, at least 1000, at least 5000, or at least 10,000 target genes, there may be at least 2, at least 5, at least 10, at least 20, at least 50 or at least 100 dsDNA oligonucleotides within the library.

As used herein, the phrase "corresponds to" refers to the ability to identify one sequence by another sequence because of complete or substantial complementarity (e.g., at least 80%, at least 90% or least 95% complementarity), or complete or substantial identity (e.g., at least 80%, at least 90% or at least 95% identity), or by degenerative coding of oligonucleotides for polypeptides. As persons of ordinary skill in the art will recognize, in a double stranded DNA molecule, one strand can correspond to a region of a target or molecule of interest by identity or substantial identity, whereas the other strand can correspond to a region of a target or molecule of interest by complementarity or substantial complementarity. Preferably, within any dsDNA molecule, the two strands are complementary to each other exclusive of any overhangs or free ends if present. Within the library, the DNA molecules may be stored with blunt ends or one or more overhangs, and optionally, with a label on one or both ends that allow for capturing of the DNA molecule through e.g., antigen-antibody associations. Techniques for storing DNA are well-known to persons of ordinary skill in the art and include but are not limited to storage at various temperatures, lyophilized or in solution and optionally in combination with buffers at desired pHs and with EDTA.

Unless otherwise specified, the reference DNA molecules may be stored in the library as single stranded DNA (ssDNA) molecules or double stranded DNA (dsDNA) molecules. When single stranded, if a sequence of interest is designed to target a molecule as an siRNA, either a targeting sequence (a sequence that corresponds to an antisense region) or a targeted sequence (a sequence that corresponds to sense region) may be present. When the dsDNA codes for a peptide to be coded, and is single stranded, the single strand may contain the code that will be translated or a complement thereof. Because dsDNA is more stable than ssDNA, for many embodiments, preferably the molecules within the library are in the form of dsDNA.

As noted above, in some embodiments a subset of DNA molecules within a library is defined as a plurality of DNA molecules that share a first primer binding region or a second primer binding region, but not both. The subsets of DNA molecules may be designed randomly or intentionally, such that within a subset, the sequences of interest of the DNA molecules share a structural feature, share a partial sequence, are directed to the same target molecule, and/or are part of the same pathway.

If the intent of the library is to be able to pull out any single sequence for amplification, then preferably for any two subsets, no more than one DNA molecule is within both subsets. Thus, no two DNA molecules that have different sequences of interest have both a common forward primer binding region and a common reverse primer binding region. In other embodiments, one may desire for each of a plurality of DNA molecules to have both a common forward primer binding region and a common reverse primer binding region. This may, for example, be preferable when a user seeks to conduct high throughput analyses on subgroups of sequences as opposed to isolating and using particular individual sequences. Thus, in this latter embodiment, one may design the library such that sequences of interest of the DNA molecules that share a structural feature, share a partial sequence, are directed to the same target, or are part of the same pathway, share a forward primer binding region and a reverse primer binding region. This type of library may be used when seeking to develop a plurality of different molecules rapidly and to screen to those molecules for potential activity when exposed to a test environment.

Preferably, each DNA molecule also comprises a first universal primer binding region and a second universal primer binding region. For each DNA molecule, the forward primer binding region, the sequence of interest and the reverse primer binding region may be located between the first universal primer binding region and the second universal primer binding region. Each primer binding region may, for example, be 15-35 or 20-30 nucleotides long and preferably, no two forward primer binding regions or reverse primer binding regions that are intended to associate with different primers contain more than 10, more than 9, more than 8 or more than 7 bases in common. By contrast, all first universal primer binding regions are the same and all second universal primer binding regions are the same. Optionally, the first universal primer binding region is the complement of the second universal primer binding region on the same strand or contains no more than 10, no more than 9, no more than 8 or no more than 7 bases in common with its complement. In some embodiments, the universal primer binding regions are immediately adjacent to the forward and reverse primer binding regions, which are immediately adjacent to the sequences of interest. In other embodiments, there are intervening sequences of, for example, 1-10 bases or 2-5 bases between any two regions. Additionally, in some cases, there are no additional bases upstream of the first universal primer binding region or downstream of the complement of the second universal primer binding region on one strand and there are no additional bases upstream of the second universal primer binding region or downstream of the complement of first universal primer binding region on the other strand. In other embodiments there are 1-10 bases or 2-5 bases in one or more of those locations.

When the sequence of interest corresponds to a region of a molecule to be targeted, preferably within the DNA molecule, the nucleotides within the forward and reverse primer binding regions, and optionally within the first and second universal primer binding regions do not correspond to regions of the target adjacent to the sequence of interest. Thus, preferably when the sequence of interest is aligned with the target, fewer than 50%, fewer than 40%, fewer than 30%, fewer than 20%, fewer than 10% or fewer than 5% of the nucleotides upstream and downstream of the sequence of interest are identical to or are complementary to the nucleotides in the regions immediately upstream or downstream of the target.

In some embodiments, each of the first universal primer binding region, the second universal primer binding region, the forward primer binding region and the reverse primer binding region may be 15-30 or 18-25 or 18-23 or 18-22 or 19-22 nucleotides in length. Preferably, the primers that are used to amplify the DNA molecules are the same size as the regions to which they correspond and are at least 80%, at least 90%, at least 95% or 100% the same as or complementary to those regions. As persons of ordinary skill in the art will recognize, it is within scope of the present invention to use primers that are shorter than the regions within the DNA molecules to which they correspond if the primers retain the ability to serve as primers and to distinguish between DNA molecules of interest and other DNA molecules within the library as needed.

Each DNA molecule may also comprise a first restriction site and a second restriction site, wherein the first restriction site is located upstream of the sequence of interest and the second restriction site is located downstream of the sequence of interest on one strand and the first restriction site is located downstream of the sequence of interest and the second restriction site is located upstream of the sequence of interest on the other strand when there are two strands. Thus, the two restriction sites may be referred to as being on one side and the other of the sequence interest, regardless of whether they are immediately adjacent to the sequence of interest.

A restriction site is a site in an oligonucleotide that may be cut by a restriction enzyme. Examples of restriction enzymes include but are not limited to EheI, NmeAIII, AcuI, EcoRI, EcoRII, BamHI, HindIII, TaqI, NotI, HinfI, Sau3A, PvuLL, SmaI, HaeIII, HgaI, AluI, EcoRV, EcoP15I, KpnI, PstI, SacI, SalI, SpeI, SphI, StuI, XbaI, I-SceI, I-CreI and I-DmoI. After a sequence has been cut, the products, which may be referred to as digestion products or digested products may be separated from one another based on any one or more techniques that are known to persons of ordinary skill in the art for separating sequences e.g., size or the presence or absence of certain moieties. Each restriction site may be within a universal primer binding region, within a forward or reverse primer binding region, between the first universal primer binding region and forward primer binding region, between the forward primer binding region and the sequence of interest, between the sequence of interest and the reverse primer binding region or between the reverse primer binding region and the universal primer binding region. The recognition site may be within any one of these regions, be between any two of these regions or span any two of these regions.

A sequence of interest may comprise, consist essentially of or consist of a region that corresponds to an siRNA, an shRNA, an miRNA mimic, an miRNA inhibitor, an lncRNA, an antisense RNA, an aptamer, an mRNA, a ribozyme or a fragment or a combination thereof. The sequence of interest will correspond to one or these types of molecules if it has the same sequence as that molecule, as a sequence that is the complement of that molecule, as a sequence that is at least 80% or at least 90% the same as or complementary to that molecule or is a mutant variant of the molecule or its complement, including but not limited to having a difference of 1-10 or 1-5 contiguous or non-contiguous bases, through base substitution, deletion or insertion or a combination thereof.

The term "siRNA" refers to small inhibitory RNA duplexes that induce the RNAi pathway. These molecules can vary in length, with each strand being 18-30 or 18-25 or 18-23 or 19-23 nucleotides long and can contain varying degrees of complementarity, e.g., at least 80%, at least 90% or 100% between the antisense and sense strands (independent of any overhangs that may or may not exist) and between the antisense strand (independent of any overhangs that may or may not exist) and its target mRNA.

Some, but not all siRNAs have unpaired overhanging bases on the 5' and/or 3' ends of the sense strand and/or the antisense strand. Preferably, in an siRNA, any overhangs that are present contain from one to six nucleotides. When the DNA molecules within the library are single stranded, they may comprise, consist essentially of or consist of a sequence that corresponds to an antisense strand, a sense strand or both. In cases in which both are present on the same strand, through subsequent processing as described below the link between the two may be cleaved or the single strand may be used as an shRNA. When the DNA molecule is double stranded, one strand may contain a sequence that corresponds to the sense strand and the other strand may contain a sequence that corresponds to the antisense strand. Alternatively, when the DNA molecule is double stranded, each strand may contain a sequence that corresponds to both the sense strand and the antisense strand, thereby allowing an shRNA molecule to be generated.

Selection of an siRNA antisense sequence that will or is likely to be functional may be accomplished by empirical research or through the use of a one or more algorithms, such as those disclosed in PCT/US01/14885, filed May 12, 2004, published as WO 2006/006948 on Jan. 19, 2006, the entire disclosure of which, including the electronic tables submitted in conjunction with that application are incorporated by reference. Examples of siRNA sequences are disclosed in the aforementioned tables of PCT/US01/14885, as well as in the paper copy of the specification of the document.

An "shRNA" is a small hairpin RNA. It is a single strand of RNA that contains a hairpin turn and that can be used to silence RNA via RNAi. Each shRNA typically contains an antisense region and a sense region that are to varying degrees complementary to each other, as well as a sequence between them that enables formation of a loop structure. Thus, the stem (including the antisense and sense regions and any additional bases prior to the formation of the loop) may be 18 to 35 base pairs long and the loop may be 4 to 15 bases long. The antisense region and the sense region of an shRNA are typically defined in the same way that the antisense and sense strands are defined for an siRNA, including but not limited to by length and degree of complementarity.

An "miRNA mimic" is a double stranded RNA molecule that is intended to mimic a native microRNA ("miRNA"). A micro RNA is a small non-coding RNA molecule that functions in transcriptional and post-transcriptional regulation of gene expression. Examples of miRNA include, but are not limited to: let-7a, let-7b, let-7c, let-7d, let-7e, let-7f, let-7g, let-71, miR-1b, miR-7, miR-9, miR-10b, miR-10a, miR-15a, miR-15b, miR-16, miR-18, miR-19a, miR-19b, miR-20, miR-21, miR-22, miR-23a, miR-23b, miR-24, miR-25, miR-26a, miR-26b, miR-27a, miR-27b, miR-29a, miR-29b, miR-29c, miR-30a, miR-30b, miR-30c, miR-30d, miR-30e, miR-31, miR-32, miR-33, miR-33b, miR-34, miR-92, miR-93, miR-94, miR-96, miR-98, miR-99a, miR-99b, miR-100, miR-101, miR-103, miR-104, miR-106, miR-107, miR-108, miR-122a, miR-123, miR-124a, miR-125a, miR-125b, miR-126, miR-128, miR-128b, miR-129b, miR-130, miR-130b, miR-131, miR-132, miR-133, miR-133b, miR-135b, miR-137, miR-138, miR-140, miR-141, miR-142s, miR-142as, miR-143, miR-144, miR-145, miR-146, miR-148, miR-148b, miR-152, miR-153, miR-155, miR-181a, miR-181b, miR-181c, miR-182, miR-183, miR-184, miR-187, miR-190, miR-192, miR-194, miR-195, miR-196, miR-199a, miR-199b, miR-200b, miR-202, miR-203, miR-204, miR-205, miR-206, miR-208, miR-210, miR-211, miR-212, miR-213, miR-214, miR-215, miR-216, miR-218, miR-219, miR-221, miR-222, or miR-223. Examples of miRNA mimics include but are not limited to MISSION® human miRNA mimics from Sigma-Aldrich, miRIDIAN® microRNA mimics from Thermo Scientific, miScript® miRNA mimics from Qiagen, and mirVana™ mimics from Life Technologies. A mimic may be the same as the miRNA or be at least 80% similar, at least 90% similar or 100% similar to the miRNA.

An "miRNA inhibitor" is a nucleic acid molecule that comprises and/or encodes an oligonucleotide with the reverse complement sequence of the miRNA that it inhibits.

An "lncRNA" is a long non-coding RNA. Thus, the lncRNA does not code for a protein. Typically, it is longer than 200 nucleotides in length. An lncRNA may regulate cellular functions such as protein synthesis, RNA maturation/transport, chromatin remodeling, and transcriptional activation and/or repression programs. Additionally, an lncRNA may influence one or more biological processes such as stem cell pluripotency, cell cycles, and DNA damage responses. Examples of lncRNAs include but are not limited to HOTAIR, HOTAIRM, HOTTIP, MALAT-1, lnc-HEIH, HULC, and AY12907. When the sequence of interest is an lncRNA, it may be up to 500 bases, up to 1000 bases, up to 2000 bases, up to 3000 bases long or up to about 20,000 bases.

An "antisense RNA" is a single stranded RNA molecule that is at least 80%, at least 90% or 100% complementary to a region of a messenger RNA. In some embodiments, it is 50 to 500 nucleotides in length.

An "aptamer" is an oligonucleotide or peptide molecule that binds to a specific target molecule. When an aptamer is a peptide, it may contain a short variable peptide domain that is attached at both ends to a protein scaffold. Aptamers can be combined with ribozymes to self-cleave in the presence of a target molecule. As persons of ordinary skill in the art recognize, there are natural aptamers or riboswitches and artificial aptamers. By way of example, specific aptamers have been designed that can target molecules such as vascular endothelial growth factor (VEGF), thrombin, human immunodeficiency virus trans-acting responsive element (HIV TAR), hemin, interferon γ, prostate specific antigen (PSA), lysozyme, theophylline and dopamine.

An "mRNA" is a messenger RNA.

A "ribozyme" is a ribonucleic acid enzyme. Thus, it is an RNA molecule that is capable of catalyzing specific biochemical reactions. Ribozymes may be naturally occurring or artificial, and they may be capable of self-cleaving or catalyzing the formation of covalent bonds.

The present invention also provides methods for isolating a nucleic acid. These methods begin by accessing a library of the present invention. As persons of ordinary skill in the art will recognize, in some embodiments, it is desirable to maintain a master library and to obtain and to use a copy of a library from which to amplify in order to obtain a nucleic acid molecule. Thus, when in possession of a library a user will preferably have or make a plurality of copies of the complete library. Because as described above, the DNA molecules within the library preferably have universal primers, i.e., primers that are common to all sequences, a person of ordinary skill in the art can use well-known techniques to generate copies of a complete library.

In one embodiment, a method begins with exposing a library (or copy thereof) to a primer pair in which no two DNA molecules that have different sequences of interest have the same combination of forward and reverse primer binding regions. The primer pair contains a first primer and a second primer. The first primer is capable of priming nucleotide synthesis in a forward direction for a DNA molecule that comprises a sequence of interest that is identical to or complementary to a sequence within a nucleotide molecule of interest, i.e., the nucleotide that one wants to obtain from the library. The second primer is capable of priming nucleotide synthesis is a reverse direction for a DNA molecule that comprises a sequence of interest that is identical to or complementary to a sequence within the nucleotide molecule of interest. The first primer is capable of associating with the forward primer binding region and the second primer is capable of associating with the reverse primer binding region. Preferably they are 100% complementary to their respective regions, and under normal conditions, will associate only with their intended regions. If the library contains ssDNA molecules, then those ssDNA molecules may be made double stranded prior to the amplification step.

The primers are exposed to the library under conditions that permit PCR to occur. For example, nucleotides, a polymerase and optionally a buffer solution may be added in order to facilitate PCR. After PCR has been allowed to occur, one may isolate the amplified products of interest according to techniques that are well known to persons of ordinary skill in the art.

In another embodiment, within the library a plurality of DNA molecules that have different sequences of interest have the same combination of forward and reverse primer binding regions. From these libraries, one isolates a group of DNA molecules. Thus, in these methods, one exposes the library to the primer pair for the DNA molecules of the group, conducts PCR and isolates the group of nucleotide molecules of interest.

In certain embodiments, the libraries and methods described above describe the use of DNA molecules that contain four primer regions, two on each side of the sequence of interest. However, libraries can also be created that have six or more primer binding regions of interest. These regions may be nested such that the order of regions of a first strand of the molecule (5'→3') is the first universal primer binding region, a first subset primer binding region, the forward primer binding region, the sequence of interest, the reverse primer binding region, a second subset primer binding region, and the second universal primer binding region. When the library contains dsDNA, the second strand would contain complements of these regions.

When these nested primer binding regions exist, in some embodiments, the universal primer binding region on one strand may be the same as the universal primer binding region on the other strand and thus the reverse complement of the universal primer binding region on the other end of the same strand. Similarly, the subset primer binding region on one strand may be the same as the subset primer binding region on the other strand and thus the reverse complement of the subset primer binding region on the other end of the same strand. However, the forward primer binding region and the reverse primer binding region are preferably sufficiently distinct that one shares no more than seven, no more than eight, no more than nine or no more than ten bases with the other (or its complement) when under maximal alignment. Similarly, no two subset primers that are not identical share more than ten, more than nine, more than eight or more than seven bases when aligned under maximal alignment, and no subset primer binding region has more than this similarity (or complementarity) with a universal primer binding region, any forward primer binding region or any reverse primer binding region.

In these embodiments, all DNA molecules within the library may have the same universal primer binding regions. Additionally, there will be a plurality of subsets of DNA molecules, wherein within each subset the same subset primer binding regions are associated with different sequences of interest. The sequences of interest may be related by target, pathway or structure or they may be unrelated. Furthermore, these subsets may be defined such that they are approximately the same size (i.e., have approximately the same number of DNA molecules) or they may be of vastly different sizes.

When isolating a specific DNA molecule of interest from a library that contains three pairs of nested primer binding regions, one can follow any of three different protocols, the first two of which are single step protocols. According to a first protocol, in order to isolate a DNA molecule of interest, one can expose the library (or copy thereof) to a first subset primer, which corresponds to the first subset primer binding region and a reverse primer, which corresponds to the reverse primer binding region. According to a second protocol, in order to isolate a DNA molecule of interest, one can expose the library to a forward primer, which corresponds to the forward primer binding region and a second subset primer, which corresponds to the second subset primer binding region. According to a third protocol, which uses two steps, one first isolates all molecules within a subset by using a first subset primer and a second subset primer. This creates and amplified set of DNA molecules that contains only molecules from the subset. Then one uses a forward primer and a reverse primer for the DNA molecule of interest. Optionally, under this third protocol, between the two steps one can make copies of the amplified subset, thereby generating a plurality of subset libraries from which to isolate different sequences of interest.

In any of the aforementioned methods, after obtaining the amplified oligonucleotides, one can remove remaining primer binding regions. As persons or ordinary skill in the art are aware, this can be done through restriction enzyme digestion followed by exposure to nucleases or other enzymes that remove single strand overhangs to generate oligonucleotides of interest.

The present invention also provides methods for cloning DNA sequences of interest. According to these methods, after obtaining an oligonucleotide of interest, one may insert the oligonucleotide of interest into an expression vector to generate an expression vector comprising the oligonucleotide of interest, deliver the expression vector comprising the oligonucleotide of interest to a cell, and expose the cell to conditions that permit cloning to occur. By way of a non-limiting example, the delivering may be via a viral particle and may be done in vivo or in vitro.

If the sequence of interest corresponds to an siRNA or an shRNA, it may be used for gene silencing. In some embodiments, the DNA molecules within the library are designed to be processed to generate siRNA molecules, each with a two nucleotide 3' antisense overhang and a single 3' sense overhang. Thus, following generation of a molecule of interest and cloning, one exposes the cell to conditions under which the cell will produce the sequence of interest or a complement thereof or both the sequence of interest and a complement thereof.

In some embodiments, the present invention provides a method for gene silencing in which from the library, one generates a single stranded DNA fragment that is converted to RNA. One may accomplish this step by using an RNA polymerase. This method further comprises exposing the cell to conditions that are conducive for RNAse mediated RNA cleavage. By way of a non-limiting example, one may use T7 RNA polymerase and phi6 RNA replicase.

In another embodiment, the present invention provides a library of DNA molecules. This library comprises, consists essentially of, or consists of a set of DNA molecules. Preferably, there are at least 100 DNA molecules, or at least 1000 DNA molecules or at least 10,000 DNA molecules, and each DNA molecule comprises a sequence of interest that corresponds to a peptide sequence. The sequence of interest is located between a forward primer binding region and a reverse primer binding region. For each DNA molecule, the combination of the forward primer binding region and the reverse primer binding region is uniquely associated with the sequence of interest and within a first subset of the set of DNA molecules, each of a plurality of DNA molecules has the same forward primer binding region and a different reverse primer binding region and within a second subset of the set of DNA molecules, each of a plurality of DNA molecules has the same forward primer binding region and a different reverse primer binding region. Optionally, within a third subset, each of a plurality of DNA molecules has the same reverse primer binding region and a different forward primer binding region, and within a fourth subset, each of a plurality of DNA molecules has the same reverse primer binding region and a different forward primer binding region. As persons or ordinary skill in the art will recognize, library may contain many more than four subsets. For example, the library may contain DNA molecules with forward primer binding regions that corresponds to n different forward primers and reverse primer binding regions that corresponds to m different reverse primers, wherein e.g., n=1 to 1000 or 5 to 500 or 10 to 100 and m==1 to 1000 or 5 to 500 or 10 to 100 and each unique combination of primers may be associated with a different sequence of interest in the DNA molecules, thereby allowing for n×m subsets.

In some embodiments, the sequence of interest of each DNA molecule comprises all 5' elements necessary for translation in vitro. These may be 5' elements that, for example, allow for translation via a mammalian system or a bacterial system. Additionally or alternatively, each DNA molecule may comprise a promoter region and/or an enhancer region. By way of example, the promoter region may be T7. Similarly, each DNA molecule may code for an affinity tag that relies on covalent and/or non-covalent interactions. By way of example, the affinity tag may be 6×His, Calmodulin-tag (KRRWKKNFIAVSAANRFK-KISSSGAL, SEQ ID NO: 75), polyglutamate tag (EEEEEE, SEQ ID NO: 76), FLAG-tag, (DYKDDDDK, SEQ ID NO: 77), HA-tag (YPYDVPDYA, SEQ ID NO: 78), His-tag (HHHHHH, SEQ ID NO: 79), Myc-tag (EQKLISEEDL, SEQ ID NO: 80), Glutathione-S-transferase-tag, Maltose binding protein-tag, Strep-tag, Isopeptag (TDKDMTIT-FTNKKDAE, SEQ ID NO: 81) and SpyTag (AHIVMV-DAYKPTK, SEQ ID NO: 82).

When the sequences of interest correspond to peptides, one can use the DNA library to create a library of enzymatically produced peptides. Thus, in separate environments, one can expose a library of the present invention to a plurality of sets of primer pairs each of which is uniquely associated with a DNA molecule of interest to generate amplified DNA molecules of interest. Next, through transcription and translation processes, one can enzymatically generate the peptide sequences from the amplified DNA molecules of interest. Finally, one can collect the peptide sequences to form a peptide library. Optionally, one may purify the peptide sequences.

If the sequences of interest within the DNA molecules do not contain 5' elements for translation, and one seeks to generate peptides, then optionally, one may add these 5' elements to the amplified DNA molecules of interest through ligation techniques. For example, one may use a DNA ligase enzyme such as T4 DNA ligase.

In another embodiment, the present invention provides a method for modular gene assembly. The method starts with accessing a library of DNA molecules. The library may, for example, comprise a set of DNA molecules of at least 100 DNA molecules, at least 1000 DNA molecules or at least 10,000 DNA molecules, wherein each DNA molecule comprises a sequence of interest that corresponds to a fragment of a coding region of a gene.

Within the library, a plurality of fragments may correspond to different mutants at a locus. Optionally, the library also contains fragments that correspond to transcriptional regulatory sequences, post-transcriptional processing sequences and/or translational regulatory sequences. In some embodiments, the locus of a mutation relative to a wild-type is within a protein coding sequence, a transcriptional regulatory sequence, a post-transcriptional processing sequence or a translational regulatory sequence. When within a coding region, the mutation may be a point mutation, a deletion, an insertion, or other mutation that results in the generation of a different polypeptide relative to the wild-type.

As with other embodiments described herein, the sequence of interest is located between a forward primer binding region and a reverse primer binding region. For each DNA molecule, the combination of the forward primer binding region and the reverse primer binding region may be uniquely associated with the sequence of interest and within a first subset of the library of DNA molecules, each of a plurality of DNA molecules has the same forward primer binding region and a different reverse primer binding region and within a second subset of the library of DNA molecules, each of a plurality of DNA molecules has the same forward primer binding region and a different reverse primer binding region and each sequence of interest has a first restriction site that is on one side of the sequence of interest and a second restriction site that is on the other side of the sequence of interest.

Next, in separate environments for each of the plurality of sets of primer pairs, one exposes the library, or a copy thereof, to a primer pair that is uniquely associated with DNA molecule of interest. The exposure is under conditions that permit amplification to generate amplified DNA molecules of interest.

Next, one removes flanking primer binding sites. The removal may, for example, be through the use of a type IIS restriction enzyme. In some embodiments, the primers or the primer pairs are methylation primers, and the removing comprises methylation dependent restriction digestion and exonuclease activity to generate blunt dsRNA molecules that lack primer binding regions.

Finally, one ligates two or more DNA molecules (e.g., 2-20 or 3-10 or 5-8) of interest to form a modular gene. The two or more DNA molecules that one ligates together comprise a first DNA molecule and a second DNA molecule, and optionally a third DNA molecule, further DNA molecule, fifth DNA molecule, etc.

In this library, and uses thereof, and in other libraries of the present invention, one may choose to introduce a mutagenic event at various stages. For example, in creating the sequences of interest, one may intentionally create a mutant variant by introducing a substitution, deletion or insertion of one or more nucleotides. Alternatively, one may synthesize the precursors for the library under conditions that are not stringent and thereby allow mutations that are not site directed. Additionally or alternatively, one may introduce mutagenic events during PCR. For example, one may conduct a sloppy version of PCR through the use of a relatively high amount of $MgCl_2$. See e.g., Pritchard et al., A General Model of Error-prone PCR, J. Theol. Biol. 234 (2005) 497-509.

When conducting the ligating step referenced above, one ligates a first fragment and a second fragment to form a fused nucleotide sequence. In some embodiments, the first fragment may correspond to a gene of interest, and the second fragment may correspond to a moiety selected from the group consisting of a fluorescent protein, a transcriptional activator, an affinity tag, a promoter region, a 3'UTR region and an IRES site. By way of further example, the ligating may comprise ligation of a fragment corresponding to a DNA binding domain from one protein and a VP16 transcriptional activator. Each fragment may be stored in the same library or in a different library, or obtained from a source other than a library. Additionally, in forming the oligonucleotide that corresponds to the modular protein, one may use 1-10 or 2-6 or 3-5 fragments that correspond to different coding regions. By controlling the order in which the amplified fragments are combined, one can control the order in which they will be ligated together.

In one example, the ligating comprises ligation of a fragment corresponding to a kinase domain of a first protein and a dimerization domain of a second protein and a localization domain from a third protein. In another example, the ligating comprises ligation of a fragment corresponding to a promoter of a first protein, a coding region of a second protein and a 3' UTR.

The modular genes may be translated to form proteins. One may screen these proteins for functionality by exposing the protein to a cell or an in vivo or in vitro condition that tests for the performance of a peptide region that corresponds to a fragment or a protein formed from a plurality of fragments that have been ligated together.

In another embodiment, the present invention provides a method for generating an expression unit. The method comprises accessing a library of DNA molecules. The library comprises a set of DNA molecules of a plurality of types. This set of DNA molecules comprises: (a) a plurality of type I DNA molecules, wherein each type I DNA molecule comprises a sequence that corresponds to a promoter region; (b) a plurality of type II DNA molecules, wherein each type II DNA molecule comprises a sequence that corresponds to a 5' regulatory region; (c) a plurality of type III DNA molecules, wherein each type III DNA molecule comprises a sequence that corresponds to a protein coding region or a fragment thereof; and (d) a plurality of type IV DNA molecules, wherein each type IV DNA molecule comprises a sequence that corresponds to a 3' regulatory region. The DNA molecules of the four types may be contained in one container or each of the four types of molecules may be stored in one of four separate containers, thereby creating sub-libraries.

Each DNA molecule comprises a sequence of interest that is located between a forward primer binding region and a reverse primer binding region. For each DNA molecule, the combination of the forward primer binding region and the reverse primer binding region is uniquely associated with the sequence of interest and within a first subset of DNA molecules, each of a plurality of DNA molecules has the same forward primer binding region and a different reverse primer binding region and within a second subset of DNA molecules, each of a plurality of DNA molecules has the same forward primer binding region and a different reverse primer binding region. Additionally, each sequence of interest has a first restriction site that is on one side of the sequence of interest and a second restriction site that is on the other side of the sequence of interest.

There may be additional subsets. For example, there may be at least 3 subsets, at least 4 subsets, at least 5 subsets, at least 10 subsets, at least 20 subsets, at least 50 subsets, at least 100 subsets or at least 500 subsets that contain DNA molecules that are defined by a commonality of a forward primer binding region or a reverse primer binding region and in some embodiments not a commonality of both a forward primer binding region and a reverse primer binding region. Additionally, the distribution of type I, type II, type III and type IV DNA molecules among the subsets may be random or non-random. Furthermore, when each type of the four aforementioned types of DNA molecules is stored within different sub-libraries, the uniqueness of primer pairs may be either only within sub-libraries or across all sub-libraries.

In separate environments under conditions that permit PCR, one may: (a) expose the library (or sub-library if the library is so divided), or a copy thereof, to a first primer pair that is uniquely associated with a type I DNA molecule of interest; (b) expose the library (or sub-library if the library is so divided), or a copy thereof, to a second primer pair that is uniquely associated with a type II DNA molecule of interest; (c) expose the library (or sub-library if the library is so divided), or a copy thereof, to a third primer pair that is uniquely associated with a type III DNA molecule of interest; and (d) expose the library (or sub-library if the library is so divided), or a copy thereof, to a fourth primer pair that is uniquely associated with a type IV DNA molecule of interest.

The PCR conditions allow for amplification of the type I DNA molecule of interest, the type II DNA molecule of interest, the type III DNA molecule of interest and the type IV DNA molecule of interest. Following amplification, one removes flanking primer binding sites; and ligates together, preferably in the following order, the type I DNA molecule of interest, the type II DNA molecule of interest, the type III DNA molecule of interest, and the type IV DNA molecule of interest to generate an expression unit.

Both the methods for creating modular proteins and the methods for assembling genes described above call for ligating nucleotide sequences together. In any method of the present invention that calls for ligation among three or more DNA fragments, the fragments may be serially added in the order in which one desires the ligation to occur. Examples of fragments that may be ligated directly or indirectly to oligonucleotides corresponding to sequences to be translated are nucleotide sequences that correspond to moieties selected from the group consisting of a fluorescent protein, a transcriptional activator, an affinity tag, a promoter region, a 3'UTR region and an IRES site. Thus, by way of a non-limiting example, fragments that optionally may be joined with an oligonucleotide corresponding to a sequence to be translated (coding sequence) may be ligated in the following order of addition (from 5' to 3'): a transcriptional activator, a promoter region, the coding sequence and a fragment that corresponds to an affinity tag or a fluorescent protein. In some embodiments, when a modular DNA sequence is created, that sequence comprises a mutant variation of a promoter or a mutant variation of an enhancer. Thus, in some embodiments, the transcriptional activator can be 5' of the promoter or 3' of the coding region so that it is able to be in close proximity of the promoter, and the tag of fluorescent protein may be 5' or 3' of the coding sequence.

The genes described above that code for the production of a protein may be screened by exposing the protein to a cell under in vitro or in vivo conditions that test for the performance of a peptide region that corresponds to a fragment. Optionally, the peptide region contains a mutation. Additionally, some of the methods described above for creating modular proteins and expression units are described assuming that each sequence of interest is associated with a unique primer pair. Alternatively, groups of types of DNA molecules may be associated with the same primer pair in order to allow for rapid generation of variants of proteins that can be exposed to high throughput screening and then characterization.

According to another embodiment, the present invention provides a method for producing a long non-coding RNA. By way of example, the lncRNA can regulate coding and non-coding genes. Thus, in some embodiments, the lncRNA are regulatory molecules such as enhancers or inhibitors of any genes. These methods comprise any of the methods described above for producing a nucleotide sequence, wherein the DNA sequence of interest corresponds to a long non-coding RNA. The sequence may either be cloned into an expression vector and one may then deliver the expression vector into cells or be produced enzymatically using RNA polymerase. Optionally, the DNA sequence of interest contains at least one mutation. Furthermore, because lncRNA may be larger than a number of other RNA described herein, persons of ordinary skill in the art may choose to create and to use libraries in which sequences of interest within dsDNA molecules are fragments of the desired lncRNA. These fragments may be assembled in the same manner in which the modular genes above are assembled.

According to another embodiment, the present invention provides a method for generating an aptamer. The method comprises accessing a library of DNA molecules. The library of DNA molecules comprises a plurality of subsets DNA molecules. Each of the DNA molecules comprises a sequence of interest that corresponds to an aptamer and the sequence of interest is located between a forward primer binding region and a reverse primer binding region. For each DNA molecule the combination of the forward primer binding region and the reverse primer binding region is uniquely associated with the sequence of interest and within a first subset of the set of DNA molecules, each of a plurality of DNA molecules has the same forward primer binding region and a different reverse primer binding region and within a second subset of the set of DNA molecules, each of a plurality of DNA molecules has the same forward primer binding region and a different reverse primer binding region. Optionally, within a third subset each of a plurality of DNA molecules has the same reverse primer binding region and a different forward primer binding region, and within a fourth subset each of a plurality of DNA molecules has the same reverse primer binding region and a different forward primer binding region. Additionally, each DNA molecule has a first restriction site that is on one side of the sequence of interest and a second restriction site that is on the other side of the sequence of interest. As with other embodiments, the library may contain many more than four subsets each of which is defined by the presence of a plurality of DNA molecules that have either the same forward primer binding region or the same reverse primer binding region.

Next, one exposes the library to a primer pair that is uniquely associated with a DNA molecule of interest. Then one amplifies the DNA molecule of interest under conditions conducive for PCR and removes flanking primer binding sites to amplify the DNA molecule thereby generating an amplified DNA molecule. Finally, one uses the amplified DNA molecule to generate an aptamer. In order to use the amplified DNA, one may expose it to RNA polymerase under conditions conducive for generation of an RNA molecule. Optionally, the PCR conditions are asymmetric.

According to another embodiment, the present invention provides a method for DNA fabrication. The fabrication may be nanofabrication, and it may be used to generate molecules between 1 kb and 20 kb or 5 kb and 15 kb. The method comprises accessing a library of DNA molecules, wherein the library comprises a set of DNA molecules. Within the set of DNA molecules, there may be a first subset of DNA molecules and a second subset of DNA molecules. The set of DNA molecules may also be described as forming groups. In this embodiment, the use of the terms group and subset denote common features and not physical separations. Thus, all of the groups may be within the same or different containers, and all of the subsets may be within the same or different containers, and the classification of a DNA molecule as within a subset may be independent of its classification with a group.

Each of the DNA molecules within a first group comprises a sequence of interest that corresponds to an aptamer and each of the DNA molecules within a second group comprises a sequence of interest that corresponds to a scaffolding element. In each DNA molecule, the sequence of interest is located between a forward primer binding region and a reverse primer binding region, wherein for each DNA molecule the combination of the forward primer binding region and the reverse primer binding region is uniquely associated with the sequence of interest. Within a first subset of the set of DNA molecules, each of a plurality of DNA molecules has the same forward primer binding region and a different reverse primer binding region and within a second subset of the set of DNA molecules each of a plurality of DNA molecules has the same forward primer binding region and a different reverse primer binding region. Additionally, each DNA molecule has a first restriction site that is on one side of the sequence of interest and a second restriction site that is on the other side of the sequence of interest. Although only two subsets are described in connection with this embodiment, persons of ordinary skill in the art will recognize that as with other embodiments, more than two may be used, and each subset may be defined by a plurality of DNA molecules that have the same forward primer binding region or the same reverse primer binding region, but in some embodiments not both.

In a first environment, one exposes the library or copy thereof to a first primer pair that is uniquely associated with a DNA molecule from the first group under conditions conducive for PCR to generate a first product. In a second environment, one exposes the library or copy thereof to a second primer pair that is uniquely associated with a DNA molecule from the second group under conditions conducive for PCR to generate a second product. Then one links the first product to the second product through, for example, ligation.

According to another embodiment, the present invention provides a method for generating an sgRNA. The method comprises accessing a library of the present invention, wherein the sequence of interest is an sgRNA and further comprises obtaining a DNA molecule of interest from the library and either: (a) inserting it into an expression vector and placing the expression vector under conditions conducive to expression; or (b) exposing the DNA molecule of interest to an RNA polymerase under conditions conducive for in vitro enzymatic synthesis.

According to an embodiment for a method for generating sgRNA, one accesses a library of DNA molecules, wherein the library comprises a set of DNA molecules. Within the set of DNA molecules, there may be a first subset of DNA molecules and a second subset of DNA molecules. The set of DNA molecules may also be described as forming groups. In this embodiment, the use of the terms group and subset denote common features and not physical separations. Thus, all of the groups may be within the same or different containers, and all of the subsets may be within the same or different containers, and the classification of a DNA molecule as within a subset may be independent of its classification with a group.

Thus, the set of DNA molecules comprises a first group of DNA molecules and a second group of DNA molecules. Each of the DNA molecules within the first group comprises a sequence of interest that corresponds to a crRNA sequence and each of the DNA molecules within the second group comprises a sequence of interest that corresponds to a tracrRNA sequence. In each DNA molecule, the sequence of interest is located between a forward primer binding region and a reverse primer binding region, wherein for each DNA molecule the combination of the forward primer binding region and the reverse primer binding region is uniquely associated with the sequence of interest.

Within a first subset of the set of DNA molecules, each of a plurality of DNA molecules has the same forward primer binding region and a different reverse primer binding region and within a second subset of the set of DNA molecules, each of a plurality of DNA molecules has the same forward primer binding region and a different reverse primer binding region and each sequence of interest has a first restriction site that is on one side of the sequence of interest and a second restriction site that is on the other side of the sequence of interest. Although only two subsets are described in connection with this embodiment, persons of ordinary skill in the art will recognize that as with other embodiments, more than two may be used, and each subset may be defined by a plurality of DNA molecules that have the same forward primer binding region or the same reverse primer binding region, but in some embodiments not both.

In a first environment, one exposes the library or a copy thereof, to a first primer pair that is uniquely associated with a DNA molecule from the first group under conditions conducive for PCR to generate a first product. In a second environment, one exposes the library or a copy thereof, to a second primer pair that is uniquely associated with a DNA molecule from the second group under conditions conducive for PCR to generate a second product. Then one links, e.g., through the use of a ligase, the first product to the second product, thereby forming an oligonucleotide of interest.

Optionally, one inserts the oligonucleotide of interest into an expression vector, placing the expression vector under conditions conducive to expression or exposes the DNA molecule to RNA polymerase under conditions conducive to in vitro enzymatic synthesis. By way of a non-limiting example, the sgRNA is capable of associating with Cas9.

According to another embodiment, the present invention provides a method for generating a nucleic acid hybridization probe. In this embodiment, one associates a nucleotide sequence generated by any of the methods of the present invention with a label. The label may be selected from the group consisting of biotinylated, digoxigenin or radioactively labeled deoxynucleotides or ribonucleotides or a combination thereof and may be associated with the oligonucleotide sequence through chemical or enzymatic means. The probe may be used in applications that are now known or that come to be known for hybridization probes.

According to another embodiment, the present invention provides a method for generating a set of RNAi molecules. An RNAi molecule may be any molecule that is either single-stranded or double-stranded, or is partially single-stranded and partially double-stranded that contains primarily or exclusively ribonucleotides (A, C, G and U) and that may cause complete or partial reduction in activity or expression of one or more target molecules. Thus, by way of example, an RNAi molecule may be: (1) an siRNA molecule that is formed from two separate strands that are capable of forming a duplex region that is 17-35 or 18-30 or 18-25 or 19-23 base pairs in length, and optionally has no or one or more overhang regions that are each up to six nucleotides in length, e.g., two nucleotides; (2) an shRNA molecule that comprises a duplex region, a stem and loop region and optionally, no tails or a 5' and/or 3' tail; (3) a molecule that mimics miRNA (microRNA), such as an miRNA mimic; and (4) a molecule that targets any non-coding RNA, e.g., lncRNA (long non-coding RNA).

The method begins with obtaining one or more dsDNA oligonucleotides from a library of dsDNA oligonucleotides. The library may contain at least 100 dsDNA oligonucleotides, at least 1000 dsDNA oligonucleotides, at least 5000 dsDNA oligonucleotides or at least 10,000 dsDNA oligonucleotides, e.g., from 100 to 10,000 dsDNA oligonucleotides.

Within the library, each sequence of interest may be located between a first region and a second region. Thus, the dsDNA oligonucleotide may comprise, consist essentially of or consist of a first region, a sequence of interest and a second region in the aforementioned order. When sequences other than those of the first region, the sequence of interest and the second region are present, they may be located between the sequence of interest and the first region, between the sequence of interest and the second region and/or distal from the sequence of interest, i.e., on the other side of the first region or the second region.

The first region may be defined by a first sequence, and the second region may be defined by a second sequence. A sequence defines a region by corresponding to the complete set of nitrogenous bases within the region. Each of the first region and the second region may independently be 15 to 500 nucleotides (or base pairs) in length, or 30 to 250 nucleotides (or base pairs) in length or 50-150 nucleotides (or base pairs) in length. Thus, in some embodiments, each strand of the dsDNA may be up to 1 kb in length. Each of the first region and the second region may have blunt ends or free ends up to 6, up to 10, up to 20 or up to 40 nucleotides long on either or both strands. In some embodiments, the first region may comprise the forward primer binding region described elsewhere in this disclosure, and the second region may comprise the reverse primer binding region disclosed elsewhere in this disclosure.

The first sequence and the second sequence are distinct from each other. Two sequences are distinct from each other if they are neither identical nor complementary to each other. The first and second sequences may have subsequences that are the same or complementary but preferably, they are designed such that different primers may be used in each of the regions and the regions within each strand would not self-hybridize. Thus, in some embodiments when aligned to determine the maximum similarity or complementarity, there is a similarity and complementarity between the first sequence and the second sequence of the same strand or different strands within a dsDNA of less than 95%, less than 90%, less than 80%, less than 70%, less than 60%, less than 50%, less than 40%, less than 30%, or less than 20% under conditions of maximal alignment. Thus, there is dissimilarity of at least 5%, at least 10%, at least 20%, at least 30%, at least 40%, at least 50%, at least 60%, at least 70% or at least 80%. For many first regions and second regions within the same molecule, there are 10 or fewer, 9 or fewer, 8 or fewer or 7 or fewer bases that align under maximum-alignment conditions.

Because dsDNA oligonucleotides are double stranded but have directionality, when referring to similarity in the aforementioned paragraph, a person of ordinary skill in the art will readily appreciate that one is referring to the similarity of regions (or regions being the same) of the two different strands, each in the 5' to 3' orientation. Similarly, when referring to dissimilarity in the aforementioned paragraph, a person of ordinary skill in the art will readily appreciate that one is referring to the dissimilarity of regions of the two different strands, each in the 5' to 3' orientation.

One of three structures of the dsDNA oligonucleotides may exist within this library to facilitate obtaining the desired molecular clones. In some embodiments, all dsDNAs have the same structural elements, whereas in other embodiments, different dsDNAs may have different structural elements. First, the first sequence may be unique for each dsDNA oligonucleotide that contains a unique sequence of interest. By being unique, it is distinct from any first sequence of any other dsDNA oligonucleotide, and thus, has a similarity of less than 95%, less than 90%, less than 80%, less than 70%, less than 60% or less than 40% to the first sequence of any other dsDNA oligonucleotide within the library under maximal alignment conditions. The region that imparts uniqueness relative to other dsDNA may be referred to as a first identifier region, and it may form, for example, a stretch over ten to fifty or twenty to thirty oligonucleotides. The first sequence may also comprise a region of fifteen to fifty or fifteen to forty or twenty to thirty contiguous nucleotides that are the same in a plurality or all dsDNA oligonucleotides. This region may be referred to as a first universal primer binding region. In some embodiments, the second sequence may have an absence of any unique regions relative to the other dsDNA oligonucleotides, and may, for example, be shorter than the first sequence but have a region that corresponds to a second universal primer binding region and be the same in a plurality or all dsDNA oligonucleotides. Therefore, each of the first sequence and the second sequence would contain a region that corresponds to a universal primer. The first universal primer binding region may be distinct from or the same or complementary to the second universal primer binding region.

Thus, the structure described above may comprise, consist essentially of or consist of a sequence of interest located between a first region and a second region. The first region may comprise, consist essentially of or consist of a first universal primer binding region and a first identifier region, and the second region may comprise, consist essentially of or consist of a second universal primer binding region.

As noted above, within each dsDNA oligonucleotide, the first universal primer binding region may be distinct from the second universal primer binding region. The sequences may be distinct by having a greatest common alignment (when comparing the 5' end of each strand of each region) of less than 90%, less than 80%, less than 70%, less than 60%, less than 50%, less than 40%, less than 30% or less than 20% or 10 or fewer or 9 or fewer, or 8 or fewer, or 7 or fewer bases under conditions or maximal alignment. Furthermore, in many embodiments, not only are the first universal primer binding region and the second universal primer binding region distinct, they also are not complementary, and thus, they have a greatest complementarity of less than 90%, less than 80%, less than 70%, less than 60%, less than 50%, less than 40%, less than 30% or less than 20%.

In a second structure, the reverse of the first structure is used. Thus, in these embodiments, the second sequence comprises, consists essentially of or consists of a second identifier region and a second universal primer binding region, while the first sequence comprises, consists essentially of or consists of a first universal primer binding region. Thus, the first sequence need not contain an identifier region.

In a third structure, the combination of the first sequence and the second sequence is unique for each dsDNA that contains a unique sequence of interest. Thus, each of the first sequence and the second sequence may be unique or the first region and the second region combined form a skeleton or scaffold and while two or more dsDNA oligonucleotides that have different sequences of interest also have the same first sequence, those different dsDNA oligonucleotides that have the same first sequences do not have the same second sequences.

Additionally, each of the first region and the second region is preferably at least 50%, at least 60%, at least 70%, at least 80% or at least 90% dissimilar from a region adjacent to the region of the target to which the sequence of interest corresponds. The dissimilarity may be defined where within the dsDNA oligonucleotide, the sequence of interest ends and each of the first region and the second region begins.

From the library, one may isolate and amplify a subset of dsDNA oligonucleotides in order to obtain isolated and amplified molecular clones. Thus, the subset may contain isolated and molecular clones of fewer than all of the different dsDNA oligonucleotides within the library, e.g., one or a plurality of different dsDNA oligonucleotides (e.g., 2-1000, 5-500, 10-250 or 25-100 of different dsDNA oligonucleotides). In some embodiments, isolation and amplification may, for example, be carried out through a PCR process. Optionally, during that process, one may cause the molecular clones to be labeled, thereby generating a labeled dsDNA library. The step of labeling may occur prior to obtaining the isolated and amplified molecular clones such that there is a labeled library of all dsDNA oligonucleotides or the step of labeling may occur during the step of obtaining isolated and amplified molecular clones such that only all dsDNA oligonucleotides within the plurality that are isolated and amplified are labeled.

Labeling may, for example, be accomplished by using a tagging primer and an amplification primer during PCR, wherein the tagging primer comprises a sequencing adapter, a randomized primer/identifier sequence and a primer sequence and wherein the amplification primer comprises an amplification/sequencing adapter.

PCR is well known to persons of ordinary skill in the art. In order to use PCR in connection with the present invention, one may expose a library to one or more primers or primer pairs. Either or both of the primers within each pair correspond to sequences within the first and second regions of fewer than all dsDNA oligonucleotides of the library. The library may be exposed to these primers under conditions that permit amplification.

For example, one may select a primer pair such that: (i) one primer corresponds to a subsequence within the first region of fewer than all dsDNA oligonucleotides (i.e., the first identifier region) and a second primer is a universal primer that corresponds to a subsequence within the second region (or the entire second region) of all dsDNA oligonucleotides (i.e., the second universal primer binding region); (ii) one primer corresponds to a subsequence within the second region of fewer than all dsDNA oligonucleotides (i.e., the second identifier region) and a second primer is a universal primer that corresponds to a subsequence within the first region (or the entire first region) of all dsDNA oligonucleotides (i.e., the first universal primer binding region); or (iii) one primer corresponds to a subsequence within the first region of fewer than all dsDNA oligonucleotides (i.e., the first identifier region) and a second primer corresponds to a subsequence within the second region of fewer than all dsDNA oligonucleotides (i.e., second identifier region). By conducting amplification under these conditions, fewer than all of the dsDNA oligonucleotides will be amplified. As persons of ordinary skill in the art will recognize, PCR amplification is preferably carried out in the presence of nucleotides and enzymes for amplification under suitable pH and other conditions that are conducive for amplification.

The description above relies on the assumption that one knows which sequence of interest is associated with which primer or primers. However, this will not always be the case. When this is not the case, prior to the implementing the steps of the previous paragraph, optionally one may first access a set of dsDNA oligonucleotides that have the same first region and second region and unknown sequences of interest and using universal primers, amplify the entire library. The primers may correspond to the first and second regions and also contain a sequencing adapter and a randomized primer/identifier sequence. In these embodiments, following labeling and amplification, each dsDNA sequence comprises, consists essentially of or consists of: (a) a first strand, wherein the first strand comprises the following elements oriented in a 5' to 3' direction (1) a sequencing adapter; (2) a first identifier region; (3) a first universal primer binding region; (4) optionally a first restriction site; (5) a sequence of interest; (6) optionally a second restriction site; (7) a second universal primer binding region; (8) a second identifier region; and (9) a second sequencing adapter; and (b) a second strand. The second strand may be complementary to the first strand. In some embodiments, within each dsDNA oligonucleotide, the first universal primer binding region is distinct from the second universal primer binding region, but within the library, all first universal primer binding regions are the same and all second universal primer binding regions are the same. Additionally, preferably within each dsDNA oligonucleotide, the first identifier region is distinct from the second identifier region, and preferably, the first identifier sequence is unique within the library and/or the second identifier is unique within the library and/or their combination is unique.

As noted above, the sequencing adapter is located at the 5' end of the amplification primer, and it is configured to enable deep sequencing. "Deep sequencing" is a technique well known to persons of ordinary skill in the art, and it refers to the ability to capture individual sequence information from a plurality of molecules within a complex pool.

The randomized primer/identifier sequence of the tagging primer may serve two purposes. First, it may allow identification of a particular sequence through its unique identifiers and subsequent isolation/amplification using these unique identifiers. Second, after the sequence of interest with which it is associated becomes known, the identifier can be used to pull that sequence from a pool, i.e., to obtain a desired sequence. Thus, in contrast to a universal primer sequence it may serve as a unique primer sequence.

Each dsDNA oligonucleotide may comprise a first restriction site on a first side of the sequence of interest and a second restriction site on a second side of the sequence of interest. In some embodiments, the first restriction site is the same as the second restriction site within a dsDNA oligonucleotide. In other embodiments, they are different. Additionally, in some embodiments, all dsDNA oligonucleotides have the same restrictions sites, while in other embodiments, fewer than all dsDNA oligonucleotides have the same pair of restriction sites.

As noted above, the methods, described in the preceding four paragraphs are particularly advantageous when initially, one does not know the identity of the sequences of interest. After the identifier regions are associated with sequences of interest, each dsDNA may be amplified and under conditions that permit the retention of a sufficient number of dsDNA oligonucleotides for future use, the dsDNA oligonucleotides may be sequenced and an index may be created and recorded in hard copy and/or in computer readable form in a non-transitory medium. Notably, in that embodiment, the first universal primer binding region is located between the first identifier region and the sequence of interest, and the second universal primer binding region is located between the second identifier region and the sequence of interest.

In other embodiments, the sequences of interest are generated either by chemical synthesis and/or enzymatic synthesis and knowingly associated with specific first sequences and second sequences. The known first sequences and second sequences may contain universal primer binding regions and identifier regions. That information may be recorded in an index.

After one has a library, he or she may obtain the isolated and amplified molecular clones. By accessing an index that correlates the sequences of interest within their first sequences and/or second sequences, one may select primer pairs that permit one to obtain only the desired clones. Then one obtains the RNAi molecules. Whereas the isolated and amplified molecular clones are preferably dsDNA molecules, the RNAi molecules may be either ssRNA molecules, e.g., shRNA molecules or they may be dsRNA molecules formed from two separate strands, e.g., siRNA molecules.

In order to obtain the RNAi molecules, one may use restriction digestion techniques as follows: (i) clone the set of one or more isolated and amplified molecular clones into one or more plasmids, (ii) express the set of one or more isolated and amplified molecular clones from within the one or more plasmids to form one or more expression products, and (iii) clone the one or more expression products through either restriction digestion cloning or assembly cloning to obtain one or more RNAi molecules.

When engaging in restriction digestion techniques, one may expose the expression products to a first restriction enzyme that is capable of cleaving the dsDNA oligonucleotide at the first restriction site and to a second restriction enzyme that is capable of cleaving the dsDNA at the second restriction site. The expression products may be exposed to the two restriction enzymes at the same time or sequentially. Additionally, the first restriction enzyme and the second restriction enzyme may be the same or different enzymes depending on the restriction sites within the dsDNA oligonucleotides of interest. If the restriction sites are the same, then there would be only one restriction enzyme to which to expose the dsDNA oligonucleotides and the cutting of both sites would occur within the same container in the same timeframe.

Next one separates the digestion products. The goal of this step is to isolate the dsDNA oligonucleotides that contain sequences of interest from oligonucleotide fragments that do not contain sequences of interest, i.e., those portions of each dsDNA oligonucleotide that after digestion are no longer associated with the sequence of interest. One method by which to do this is size. In other methods, preferably each end of the duplex has a moiety for isolation associated with it prior to digestion. After digestion, a technique for capturing the moiety may be used to cause separation. For example, the technique may rely on affinity chromatography for elements that are present within flanking elements of a dsDNA sequence but are absent from the sequence of interests. In one non-limiting embodiment, the technique comprises exposure to a support containing avidin or streptavidin when the flanking region contains biotin.

After one is in possession of the digestion product that contains the siDNA/shDNA, which may be referred to as an isolated and/or purified siDNA, one may expose that siDNA to an enzyme that is capable of generating RNA from DNA. In some embodiments, the enzyme is capable of generating dsRNA from a dsDNA template, for example, the enzyme may be Phi6. If restriction enzymes are selected so that the digested products have sticky ends, the siRNA will have overhangs. Optionally, one may expose the shRNA to an RNA endonuclease, e.g., dicer in vitro to form siRNA.

Instead of using techniques that are based on restriction enzyme digestion, one may enzymatically generate one or more RNAi molecules from the one or more isolated and amplified clones. Here, one may use a polymerase that is capable of generating RNA from DNA. The generation of the RNAi molecule will be done in the presence of ribonucleotides. Those nucleotides may be modified or unmodified. For example there may be 2'-O-alkyl modified nucleotides such as 2'-O-methyl modified nucleotides and/or 2'fluoro modified nucleotides.

In some embodiments, each strand of the dsDNA comprises a sequence of interest and further comprises a complement to the sequence of interest and a loop forming region that is between the sequence of interest and its complement on the same strand. In these embodiments, ultimately each strand will be able to form a shRNA. Additionally, in these embodiments, the loop forming region and the complement of the sequence of interest are located between any identifier or primer binding regions and the sequence of interest.

In some embodiments, the first sequence further comprises a promoter sequence. A promoter sequence is a sequence that can be used as a binding site for a polymerase or one or more other molecules or co-factors that increase the likelihood of initiation of transcription. In some embodiments, the restriction site is located between the promoter region and the sequence of interest.

In other embodiments, the promoter region is located between the first restriction site and the sequence of interest. In these latter embodiments, one may expose the siRNA to a replicase such as Phi6 in the presence of ribonucleotides to generate an amplified set of dsRNA and expose the dsRNA to an endonuclease such as dicer to form siRNA. Thus, in these cases, the promoter region remains with the sequence of interest after digestion by the restriction enzymes. In the resulting siRNA, each strand may, for example, be 25 to 27 nucleotides in length. Optionally, there may be a second promoter region located on the opposite side of the sequence of interest between the sequence of interest and the restriction site such that it too is retained after digestion. In other embodiments, the second strand may have no promoter regions (other than the complement of the aforementioned promoter region so that there is a promoter region on only one side of the sequence of interest) or have one that is situated such that it is not retained after digestion.

As persons of ordinary skill in the art will recognize, the methods described above do not depend on the size or content of the library. Moreover, because of the stability of DNA, one may store the library for extended amounts of time at low cost. In some embodiments, the library contains a set of sequences that correspond to siRNAs that target only mRNA of the same species, e.g., *Homo sapiens.*

In some embodiments, the dsDNA oligonucleotides are part of a pool or library that comprises a first subset of dsDNA oligonucleotides and a second subset of dsDNA oligonucleotides, and the first region of each dsDNA oligonucleotide further comprises a subset identifier region. The subset identifier region may be located between the first universal primer binding region and the first identifier region, and within the first subset of dsDNA oligonucleotides, the subset identifier region of each dsDNA oligonucleotide has a sequence that is the same. Within a second subset of dsDNA oligonucleotides, there may also be a subset identifier region that is the same, and the subset identifier region for the first subset of dsDNA oligonucleotides is distinct from the subset identifier region of the second subset of dsDNA oligonucleotides (e.g., at least 50%, at least 60%, at least 70%, at least 80% or at least 90% different). As persons of ordinary skill the art will readily recognize, the library may contain third, fourth, fifth, sixth, seventh, eighth, ninth, tenth, etc., subsets of pluralities of dsDNAs with different subset identifier sequences. From these pools, one may, for example, generate a plurality of RNAi molecules that target different genes that are part of the same pathway, if the subsets are designed such that the sequences of interest are so related. Because these dsDNAs will have both subset identifiers and unique identifiers, the same library can be used to generate pools of different RNAi molecules and individual RNAi molecules.

For illustration purposes, the subset identifiers of the preceding paragraph are described within the first region. Alternatively, they may be within the second region, and in some embodiments, there may be a first subset identifier region within the first region and a second subset identifier region within the second region. Within a dsDNA, the first subset identifier region may be distinct from or the same as the second subset identifier region. Additionally, when both first and second subset identifier regions are present, in some embodiments, all molecules with the same first subset identifier region have the same second subset identifier region. In other embodiments, two or more different subsets of dsDNA oligonucleotides have the same first subset identifier region but different second subset identifier regions or vice versa; however, the combination of these two regions may be used to identify desired subsets.

When the dsDNA oligonucleotides have subset identifier regions, certain methods of the present invention may, for example, be conducted in the presence of a first subset primer and a second subset primer. In one embodiment, the first subset primer corresponds to the first subset identifier region of one or more dsDNA oligonucleotides and the second subset primer corresponds to the second subset identifier region of one or more dsDNA oligonucleotides. One will be able to use this primer pair to amplify dsDNA oligonucleotides that contain subset identifier regions that correspond to both primers.

If there is only one of either the first subset identifier region or second subset identifier region present or both are present, the subset primer that corresponds to a subset identifier region that is present may be used with a universal primer that corresponds to the universal primer binding region at the other end of the dsDNA oligonucleotide. Thus, if one were to use both subset primers with the aforementioned universal primers in different containers (being exposed to copies of the same library), one would be able to amplify oligonucleotides that contain subset identifier regions that correspond to either subset primer alone and not the other subset primer as well as dsDNA oligonucleotide that contain both subset primers, so long as the universal primer binding regions are present. As persons of ordinary skill in the art will recognize, there may, for example, be at least 2, at least 3, at least 4, at least 5, at least 6, at least 10, at least 20, at least 50, at least 100, at least 500, at least 1000, etc. subsets that are defined by the subset identifier regions Optionally, the first subset of dsDNA oligonucleotides comprises a first group of dsDNA oligonucleotides and a second group of dsDNA oligonucleotides, wherein the first region of each dsDNA oligonucleotide within the first subset of dsDNA oligonucleotides further comprises a group identifier region. The group identifier region may be located between the first subset identifier region and the first identifier region, and within the first group of dsDNA oligonucleotides, the group identifier region of each dsDNA oligonucleotide is the same, and within the second group of dsDNA oligonucleotides, the group identifier region is the same, and the group identifier region of the first group of dsDNA oligonucleotides is distinct from the group identifier region of the second group of dsDNA oligonucleotides.

As with the subsets, the group may be defined by the presence of a group identifier region only within the first region, only within the second region or in both regions, in which case there would be a first group identifier region within the first region and a second group identifier region within the second region. Additionally, for one or more, or each subset there may be at least 2, at least 3, at least 4, at least 5, at least 6, at least 10, at least 20, at least 50, at least 100, etc. groups that are defined by the group identifier regions. Primer pairs that define a desired group or groups may be used to obtain the oligonucleotides within those groups.

In still further embodiments, in one, a plurality or a majority of dsDNA oligonucleotides, there may be an additional subsequence within the first region that may be used to separate dsDNA oligonucleotides within a group. This subsequence of the first region may be referred to as a subgroup. As with the groups, a subgroup may be defined by the presence of a subgroup identifier region only within the first region, only within the second region or in both regions, in which case there would be a first subgroup identifier region within the first region and a second subgroup identifier region within the second region. Additionally, for one or more or each group, there may be at least 2, at least 3, at least 4, at least 5, at least 6, at least 10, at least 20, at least 50, at least 100, etc. subgroups that are defined by the subgroup identifier regions. Furthermore, one, a plurality, or all of the groups may be defined by one or two subgroup identifier regions. Primer pairs that define a desired subgroup or subgroups may be used to obtain the siRNA within those subgroups.

Thus, for one, a plurality, at least 30%, at least 40%, at least 50%, at least 60%, at least 70%, at least 80%, at least 90%, or all dsDNA oligonucleotides within a library, the first region may comprise, consist essentially of or consist of universal primer binding region, a subset identifier region, a group identifier region, a subgroup identifier region and an identifier region. Optionally, these regions are 15-50 nucleotides long and nested such that within the first region, the subgroup identifier region is proximal to the sequence of interest and located between the sequence of interest and the group identifier region. The group identifier region within the first region may be located between the subgroup identifier region and the subset identifier region, and within the first region, the subset identifier region may be located between the group identifier region and the universal primer binding region. An analogous organization may be present in the second region so that within the dsDNA oligonucleotide, there are nested primers. Alternatively, the second region may have an absence of one or more of these regions, while containing only a universal primer binding region or a universal primer binding region and fewer than all of the aforementioned regions. Optionally, there is a restriction site on one or both sides of the sequence of interest within any of the universal primer binding region, a subset identifier region, a group identifier region, a subgroup identifier region and an identifier region, or between any two of those regions or between the identifier region and the sequence of interest.

Within the plurality of sequences there may, for example, be from 200 to 200,000 unique sequences of interest, from 1,000 to 100,000 unique sequences of interest, from 10,000 to 50,000 unique sequences of interest or from 20,000 to 40,000 unique sequences of interest. In some embodiments, from 2 to 200 sequences of interest, 4 to 100 sequences of interest or 8 to 50 sequences of interest have at least one common primer associated with them that is not a universal primer, but no two different sequences of interest have identical first regions and second regions. Thus, a kit may be designed such that the subsets of sequences that have a common primer are designed to facilitate generation of subpools of shRNA or siRNA through for example, use in combination with a universal primer. These subpools may, for example, be defined by being part of a common pathway or by targeting the same gene of interest.

Figure 4:
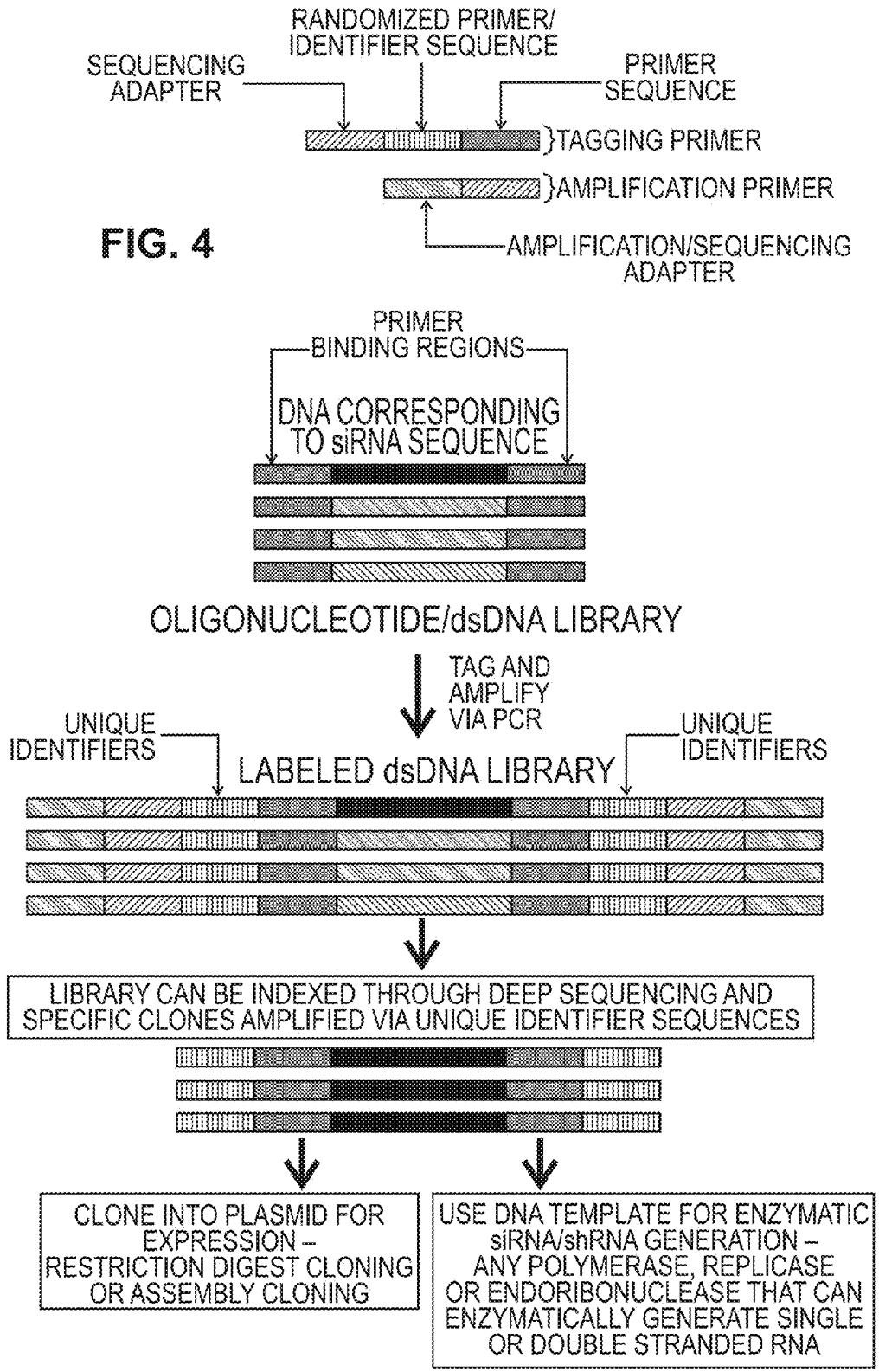
FIG. 4 is a representation of the generation of a labeled dsDNA library.

Various embodiments of the present invention may be further appreciated by reference to the accompanying figures. As shown in FIG. 4, each oligonucleotide of the library may be designed as a DNA that corresponds to a siRNA sequence, with a primer binding region on each end of each molecule. FIG. 4 further illustrates a technique of an embodiment of the present invention when the sequences of interest are not originally known.

Creation of the DNA may, for example, be through the use of phosphoramidite chemistry. As will be familiar to a person of ordinary skill in the art, when using this technology one may lay down a first nucleotide that is a phosphoramidite, an oxidized phosphoramidite or phosphoramidite derivative. Through a coupling step a second phosphoramidite may be added to the first phosphoramidite in a manner that permits growth in the 3' to 5' direction. Preferably cycles of coupling, oxidation and deblocking are repeated i−1 times, wherein i=the number of nucleotides. The use of phosphoramidites to synthesize oligonucleotides is well known to persons of ordinary skill in the art and is described in U.S. Pat. No. 4,973,679, issued Nov. 27, 1990, the entire disclosure of which is incorporated by reference.

In some embodiments, chemical synthesis may be performed on microarrays, including through the use of programmable array technology, which offers the possibility to synthesize pools of thousands to millions of sequences per array. Persons of ordinary skill in the art will be familiar with relevant technologies for accomplishing this task, including but not limited to ink-jet printing with standard reagents, photolabile 5' protecting groups, photo-generated acid deprotection and electrolytic acid/base arrays. Additionally, as persons of ordinary skill in the art will recognize, DNA may be synthesized exclusively by increasing the chain length one nucleotide at a time or by growing a chain through ligation of two or more nucleotides at a time. These methods can be used to generate random sequences. Alternatively, programmable array technology permits persons of ordinary skill in the art to design and to create systematically oligonucleotides that possess desired sequences, i.e., sequences of interest, which correspond to a region of a target.

Returning to FIG. 4, the set of dsDNA oligonucleotides that contains the sequences of interest and primer binding regions may be associated with randomized primer/identifier sequences and optionally a sequencing adapter and an amplification/sequencing adapter as shown in the upper portion of FIG. 4. Following this step, the identity of sequences from randomly generated DNA can be identified, even if not originally known. Thus, after initially creating the library, the DNA oligonucleotides may then be released from a support. At this time, the DNA may be single stranded or optionally, it may be converted to a double stranded molecule prior to release from the support. As shown in the figure, identifiers may be added at or near the ends of each fragment during PCR in the presence of a tagging primer and an amplification primer. These identifiers may be embedded as variable subsequences within the primers. In some embodiments, conditions are such that each molecule has a high probability of receiving a unique identifier pair or that there is an extremely low probability of generating two sequences with the same identifier on either end. Preferably, the probability of generating two sequences with the same identifier on either end is less than 1%, less than 0.1%, less than 0.01%, or less than 0.001%. These unique identifiers may also be referred to as tags and may be used to create a tagged or labeled library.

Thus, by way of further illustration, one amplifies and labels (or tags) the dsDNA via PCR in order to generate a labeled dsDNA library. Through the use of tagging primers that comprise, consist essentially of or consist of: (1) a sequencing adapter; (2) a randomized primer/identifier sequence; and (3) a primer sequence, and an amplification primer comprising, consisting essentially of or consisting of a primer region and an amplification region, the labeled dsDNA will contain each of these regions. The library can then be indexed through deep sequencing e.g., a next generation sequencing (NGS) platform, and specific clones can be amplified via the randomized primer/identifier sequences, which also may referred to as unique identifier sequences. This technique can therefore be employed to amplify, label, and identify specific DNA sequences from the library. With this information, one may obtain molecules that correspond to sequences selected for knockdown of particular genes when introduced as siRNAs. For example, one may clone sequences into plasmids for expression-restriction digest cloning or assembly cloning or one may use a DNA template for enzymatic siRNA/shRNA generation. For the latter process, one may use any polymerase, replicase or endoribonuclease that can enzymatically generate single or double-stranded RNA.

Figure 3:
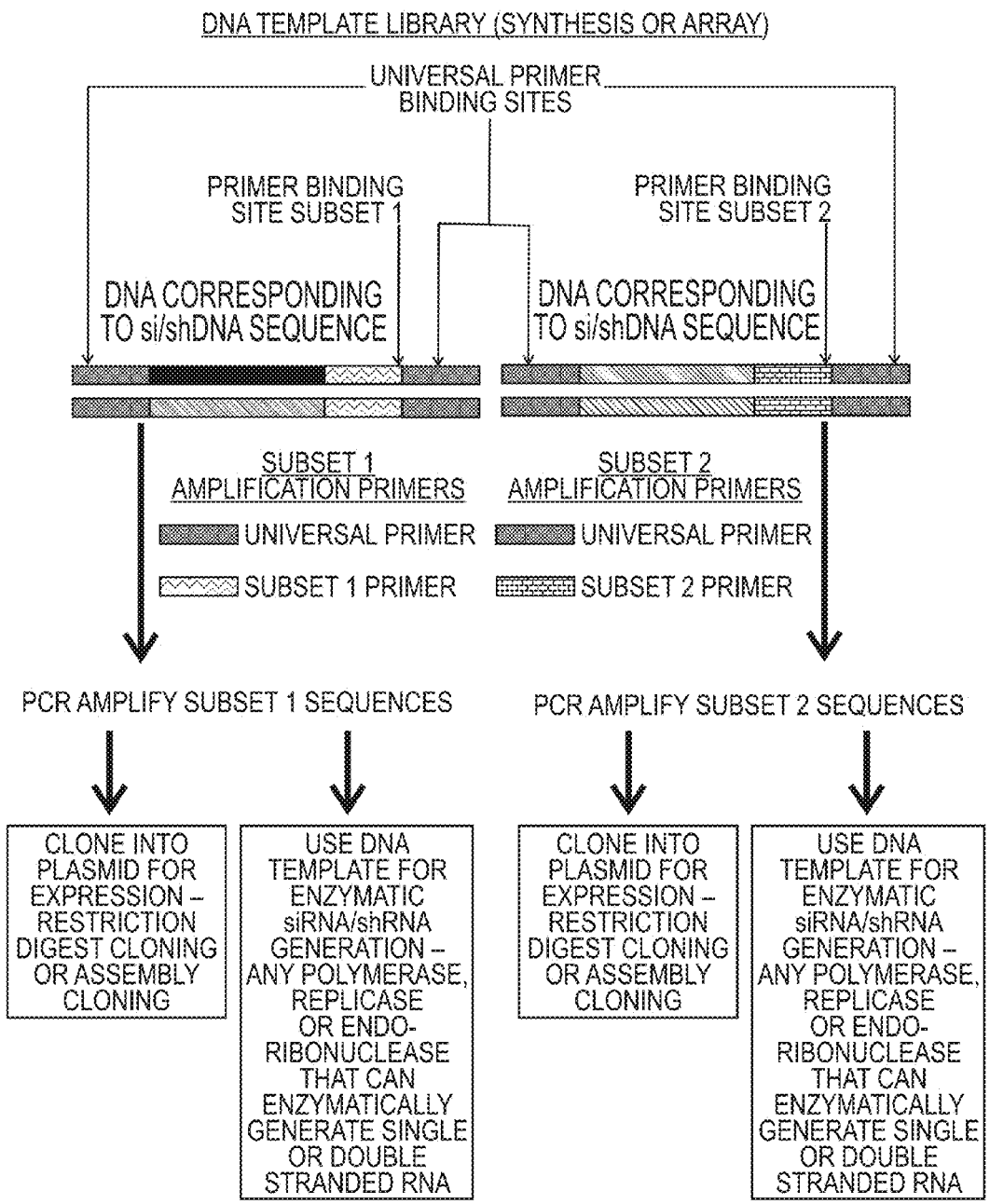
FIG. 3 is a representation of a strategy for obtaining amplified subsets of sequences from a DNA template library.

As FIG. 3 shows, in order to obtain desired si/shRNA from another type of library, one may start with a nucleic acid (DNA) template library that is constructed in a manner such that subsets of molecules within the library contain a common primer binding site. The library may, for example, be synthesized on an array. In the figure, the primer binding sites are denoted as primer binding site subset 1 and primer binding site subset 2. The molecules within a subset may be functionally related as in a common molecular/biological pathway, evolutionarily related as in members of a gene family (e.g., Polo like Kinases, Ago family members, etc.), from the same or different species or unrelated depending on one's needs.

As the figure further illustrates, in some embodiments, there may be only one subset primer binding site (i.e., subset identifier) per subset, but universal primer binding sites on both ends of each DNA molecule. Alternatively, the library may be designed to include two subset identifiers within each dsDNA oligonucleotide (not shown), which also would each have universal primer binding sites at both ends. In cases in which there is only one subset specific primer, a person of ordinary skill in the art could use the corresponding primer and a universal primer that corresponds to the universal primer binding region at the other end to amplify the product. By contrast, in cases in which there are two subset specific primer binding sites, one can use both subset specific primers to obtain a subset by PCR. These subsets can be used as a group template for enzymatic RNA synthesis using any polymerase, replicase or endoribonuclease that can enzymatically generate single or double stranded RNA, or they can be cloned into expression vectors such as a plasmid for expression-restriction digest cloning or assembly cloning as a pool.

Figure 2:
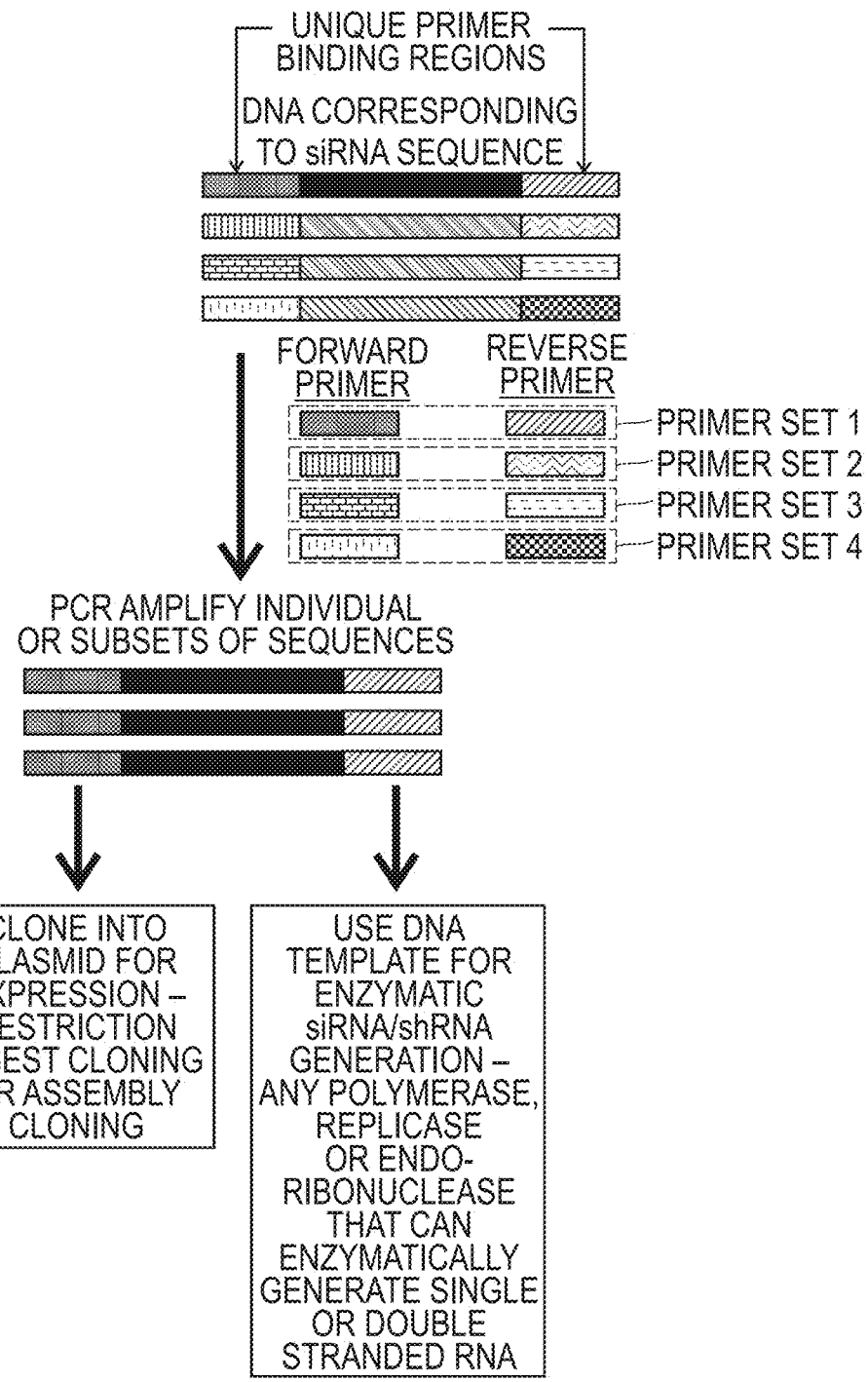
FIG. 2 is a representation of a strategy for obtaining a specific sequence or subset of sequences from an si/shDNA template library.

FIG. 2 shows a general method for obtaining individual or subsets of sequences from a library that has DNA corresponding to siRNA sequences and that have a pre-designed unique primer binding site on each end. Thus, whereas FIG. 3 shows means for obtaining subsets of oligonucleotides, FIG. 2 shows means for obtaining individual oligonucleotides of interest or subsets. The unique primer binding regions may by unique to pluralities of dsDNA or to individual dsDNAs. Assuming that they are unique to individual dsDNA, the method allows for discrimination between sequences through the use of specific pairs of PCR primers consisting of forward and reverse primers and denoted as primer set 1, primer set 2, primer set 3, and primer set 4 in the figure. By conducting PCR amplification in the presence of a primer pair that corresponds only to a desired sequence of interest, one can select individual sequences from the library and use them for the enzymatic generation of RNA in vitro or cloned into expression vector(s). If the same primer pair is associated with a plurality of sequences, then one would be able to amplify the plurality of sequences with the same primer pair.

Figure 6:
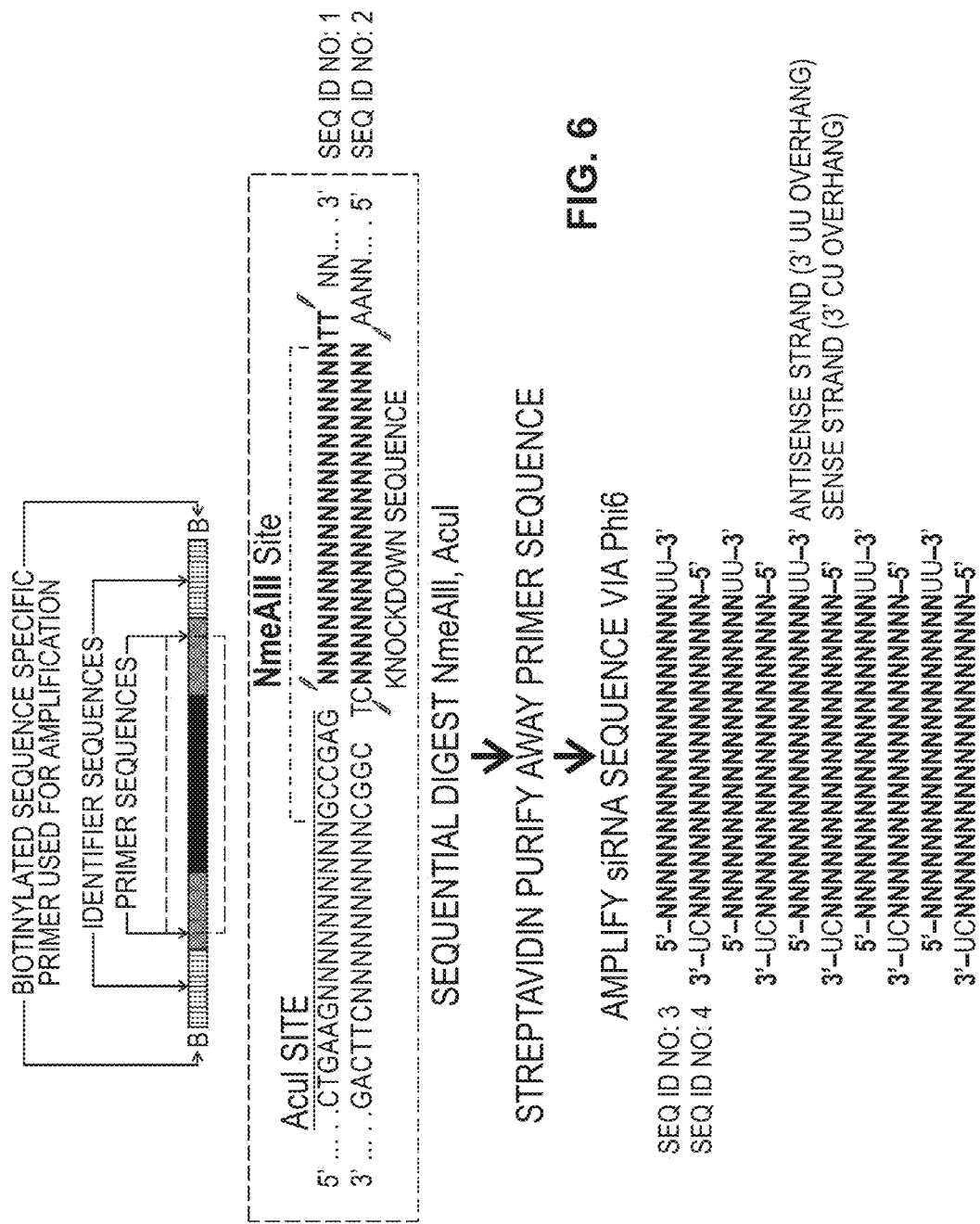
FIG. 6 corresponds to a schematic that shows a solution for generating siRNAs from cloned DNA sequences. The differently patterned bars correspond to elements present within cloned DNA sequences. The B at the ends of the cloned DNA sequence indicates the presence of a biotin tag that allows for separation of primer elements away from the DNA corresponding to the siRNA sequence of interest. The antisense sequence is the upper strand of the siRNA duplex.

As shown in FIG. 6, when obtaining RNAi molecules, one may generate RNA molecules from dsDNA oligonucleotides that have labeled, e.g., biotinylated, sequence specific primer regions. Thus, each dsDNA oligonucleotide contains a sequence of interest (black bar) between primer sequences. In this embodiment, the primer sequences and sequences of interest are located between identifier sequences, which at their termini are biotinylated. The dsDNA, which is formed in part by SEQ ID NO: 1 and SEQ ID NO: 2 may contain two different restriction enzyme sites, one on each side of the sequence of interest. These restriction sites may, for example, be defined by a sequence within the first region, the second region or both.

For example, the two restriction sites may be an AcuI site on one side of the sequence of interest and an NmeAIII site on the other side of the sequence of interest. The NmeAIII recognition sequence may be present within the first region, and this sequence may cause cleavage twenty-one nucleotides downstream of this recognition site (GCCGAG). One may then perform sequential digestion in the presence of enzymes that permit cutting at these restriction sites. Next one may purify away the primer sequences and undigested sequences of interest through, for example, streptavidin purification or other size or affinity based purification methods.

Amplification may then proceed in the presence of an enzyme that permits the creation of siRNA. In the figure, the strands of the siRNA are SEQ ID NO: 3 and SEQ ID NO: 4 are formed using Phi6. As the figure shows, in this example, each siRNA will contain a 3' UU antisense overhang and a 3' CU sense overhang that correspond to how the restriction enzymes cut the molecule.

Figure 9:
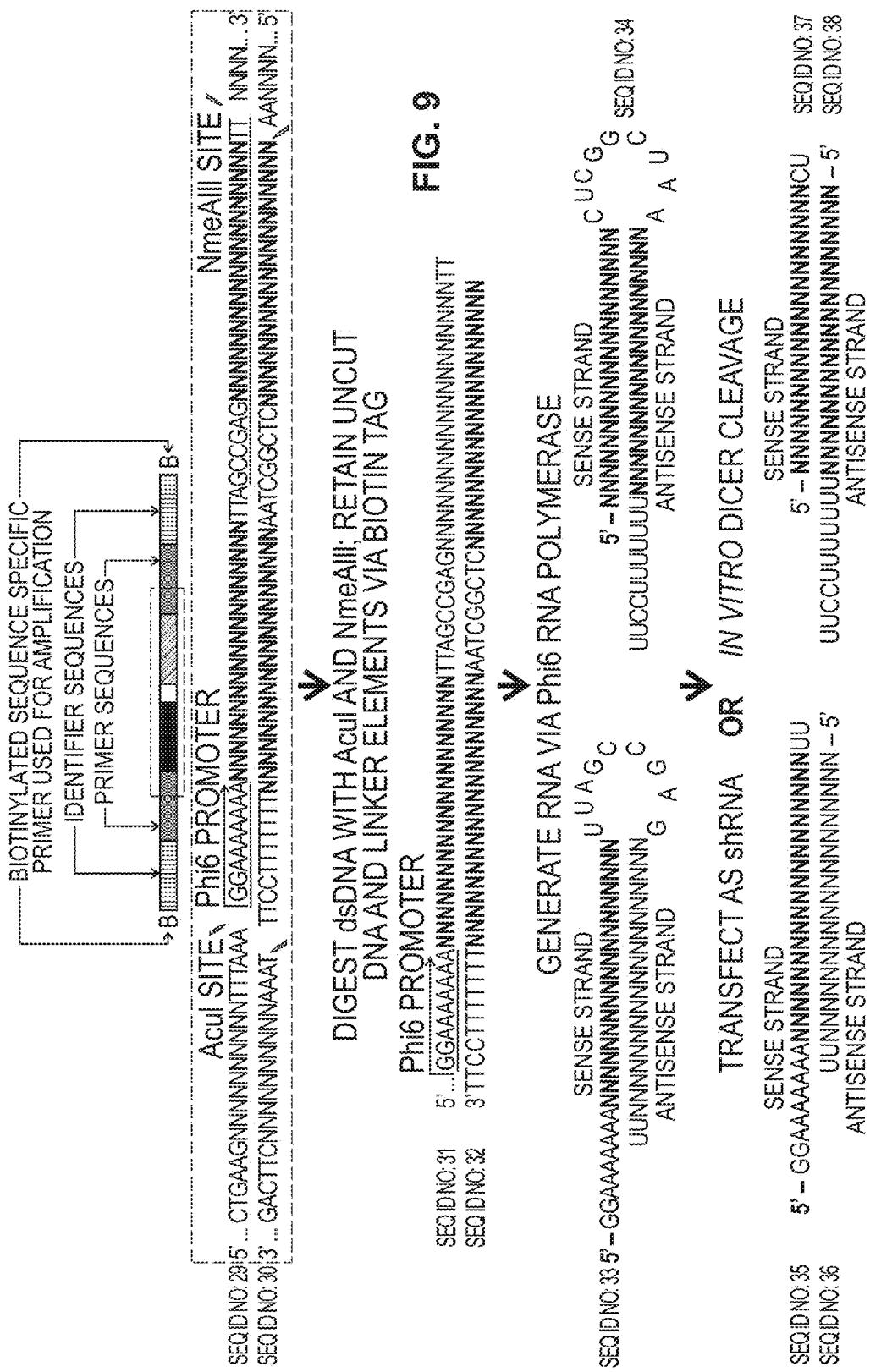
FIG. 9 is a representation of a strategy for generating siRNA that is promoter dependent.

An alternative embodiment for obtaining siRNA from a biotinylated dsDNA library is depicted in FIG. 9. In this embodiment, each strand contains both a sense region and an antisense region, represented by bold Ns, such that each strand can, when separated from the complementary strand, form an shRNA molecule. Examples of relevant portions of those strands are represented by SEQ ID NO: 29 and SEQ ID NO: 30. Each hairpin can be transfected as a hairpin, or prior to transfection the loop structure and can be cleaved away. Thus, as shown in the figure on each strand a sequence of interest and its complement are between primer sequences and identifier sequences.

Digestion takes place in the presence of AcuI and NmeAIII Through the biotin tags, one separates out uncut DNA and linker elements, thereby generating dsDNA corresponding to SEQ ID NO: 31 and SEQ ID NO: 32. From there, one can generate RNA via Phi6 (SEQ ID NO: 33 and SEQ ID NO: 34) and transfect this RNA as shRNA or one can conduct in vitro cleavage via for example, dicer to generate a first duplex formed by SEQ ID NO: 35 and SEQ ID NO: 36 and a second duplex formed by SEQ ID NO: 37 and SEQ ID NO: 38. Notably, in FIG. 9, the promoter element is cleaved away prior to digestion.

Figure 8A:
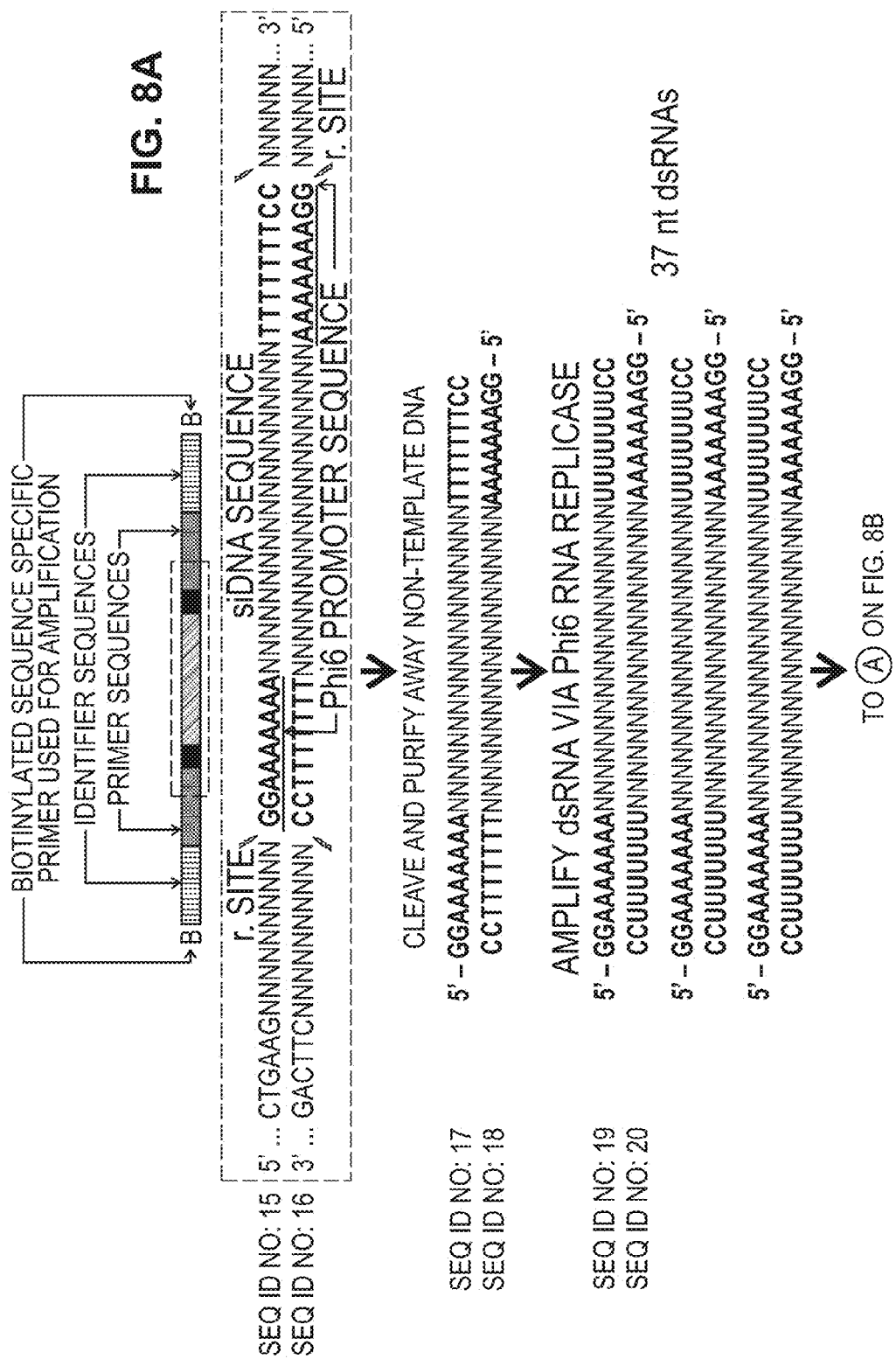

By contrast, there may be a promoter dependent generation of siRNA from a dsRNA template. As shown in FIGS. 8A and 8B, an example of this method relies on in vitro cleavage of dsRNA by, for example, Giardia dicer to produce dsRNA in which each strand is 25-27 nucleotides in length. In this process as shown, a dsDNA oligonucleotide with a biotinylated sequence specific primer region may be used. The dsDNA may contain a promoter sequence on each side of the sequence of interest, wherein each promoter sequence is between a restriction sites and the sequence of interest. Thus, in contrast to the embodiment of FIG. 9, in FIGS. 8A and 8B, the promoter region remains associated with the sequence of interest after restriction digestion.

As shown in FIG. 8A, one may cleave the dsDNA (formed in part by SEQ ID NO: 15 and SEQ ID NO: 16) at the restriction sites and purify away the non-template DNA to obtain a smaller duplex (formed by SEQ ID NO: 17 and SEQ ID NO: 18). Notably, this duplex contains a promoter site at each end. Following purification is an amplification step, in the presence of the replicase that corresponds to the promoter to generate dsRNA where each strand that is generated is 37 nucleotides long (see plurality of duplexes of SEQ ID NO: 19 and SEQ ID NO: 20). Following amplification, the duplex may be cleaved in vitro by dicer to generate different duplexes where each sequence is 25 to 27 nucleotides in length, see FIG. 8B and duplexes formed by: (i) SEQ ID NOs: 21 and 22; (ii) SEQ ID NOs: 23 and 24; (iii) SEQ ID NOs: 25 and 26; and (iv) SEQ ID NOs: 27 and 28.

Figure 7:
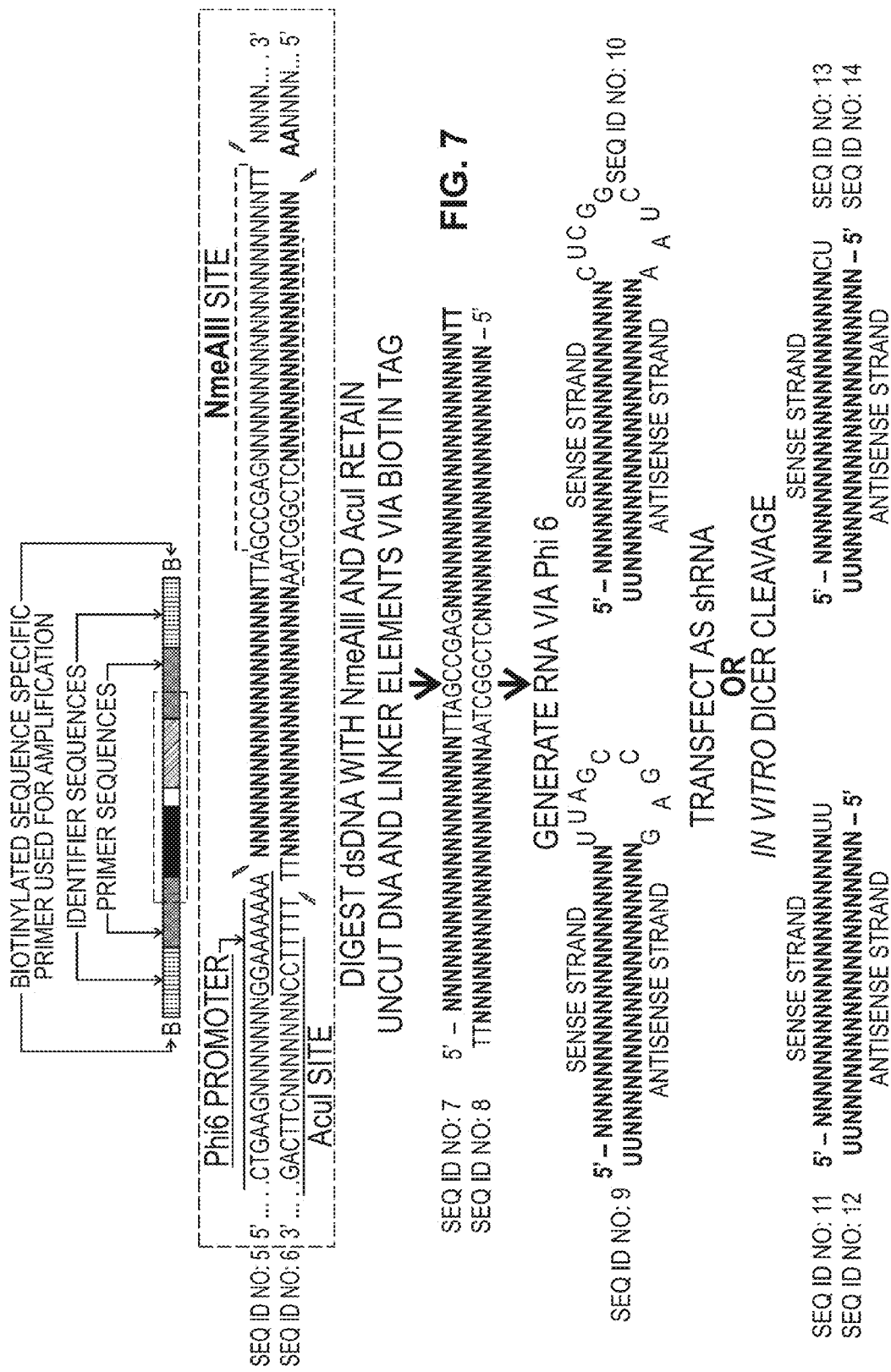
FIG. 7 is a representation of a strategy for generating shRNA or siRNA from dsDNA.

As with the promoter independent generation of siRNA from a dsRNA template, one can start with dsDNA sequences in which one strand has a sense sequence and the other strand has an antisense sequence as shown in FIG. 8A or each strand can possess both an antisense sequence and a sense sequence as shown in FIG. 7. For example, as shown in FIG. 7 one strand (in the 5' to 3' direction, SEQ ID NO: 5), may contain a restriction enzyme site followed by a promoter site, followed by a sense sequence followed by a loop region, followed by an antisense sequence, followed by a second restriction site. The other strand (in the 5' to 3' direction, SEQ ID NO: 6) may contain an absence of a promoter site, the second restriction site, a sense sequence, a loop forming sequencing, an antisense sequence, the complement of the promoter sequence and the first restriction site.

Thus, as FIG. 7 illustrates, the dsDNA molecule may be digested with first and second restriction enzymes (shown in the figure as NmeAIII and AcuI) that are capable of cutting at the first and second restriction sites to generate a duplex formed by SEQ ID NO: 7 and SEQ ID NO: 8. Through the use of biotin tags and appropriate avidin technology, one may separate out the uncut DNA and other elements that are not associated with the target. Next one may use the digested dsRNA to generate dsRNA in the presence of an enzyme that is capable of generating dsRNA from dsDNA and to which the promoter corresponds (shown in the figure as Phi6). This will result in two different shRNAs (SEQ ID NOs: 9 and 10), which may either be transfected into cells or cleaved in vitro via e.g., dicer (to form two duplexes that are represented by SEQ ID NOs: 11 and 12 and by SEQ ID NOs: 13 and 14).

Figure 10A:
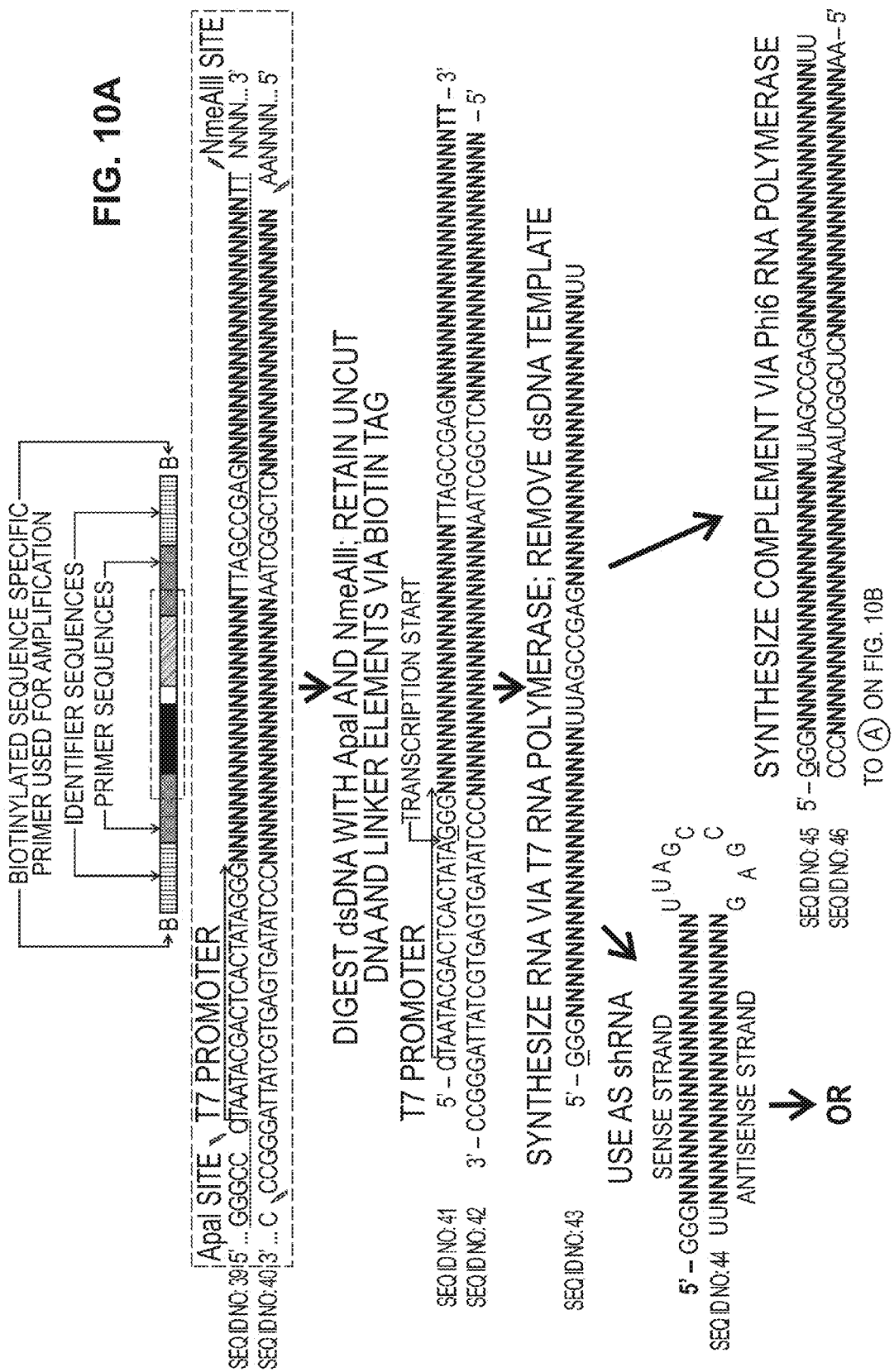

In an alternative embodiment, one can use a combined T7/Phi6 promoter method for generating dsRNA. This method is depicted in FIGS. 10A and 10B. As shown in FIG. 10A, the dsDNA may be constructed so that one strand includes (in the 5' to 3' direction) a first restriction site (shown as an ApaI site), a T7 promoter region, a sense region, a loop region, an antisense region and a second restriction site (shown as an NmeAIII site) (SEQ ID NO: 39). The other strand contains (in the 5' to 3' direction) a sequence that corresponds to the second restriction site, a sense region, a sequence that corresponds to a loop region, an antisense sequence, a sequence that corresponds to the complement of the T7 promoter region and a sequence that corresponds to the first restriction site (SEQ ID NO: 40).

According to this method, one digests the dsDNA with the two restriction enzymes and separates the digested sequences from undigested sequences and linker elements. As with other embodiments, this may, for example, be done through the use of biotin tags. At this point, each of the strands contains both an antisense region and a sense region (see SEQ ID NOs: 41 and 42). Only the first strand also contains a promoter region. Consequently, through the use of T7 RNA polymerase, one may generate ssRNA (SEQ ID NO: 43).

This single stranded RNA will be the complement of the second strand and be an RNA copy of the first strand that is capable of forming shRNA. At this point, one can either use the shRNA (see SEQ ID NO: 44) or process it in vitro with Dicer to convert the shRNA into an siRNA with two separate strands (SEQ ID NO: 47 and 48) as shown on FIG. 10B. Alternatively, one can take the ssRNA that was generated with T7 RNA polymerase and amplify and generate a second strand with Phi6 RNA replicase. This will result in the presence of two separate strands of RNA, each with a sense region, an antisense region and a spacer between the sense region and the antisense region on each strand that will correspond to a loop structure. As a person of ordinary skill in the art will recognize, the sequences of the loops in each strand are complementary to each other and each strand may be used as shRNA (SEQ ID NOs: 49 and 50) or optionally may be processed to duplexes (SEQ ID NOs: 51 and 52; SEQ ID NOs: 53 and 54).

Figure 11:
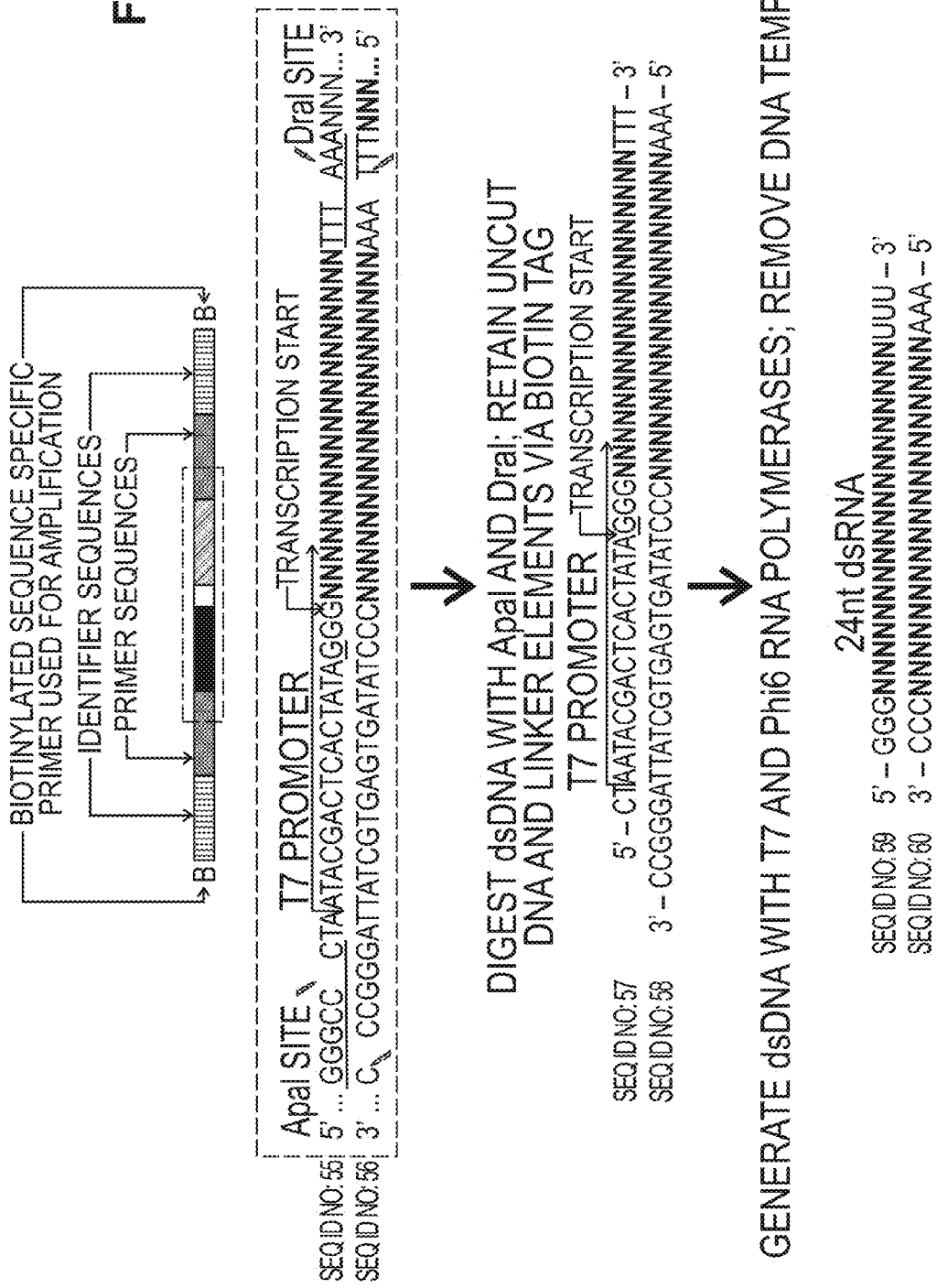
FIG. 11 is a representation of a strategy for generating siRNA using a combination of T7 RNA polymerase and Phi6 RNA replicase.

In still another embodiment in which a promoter is used, one may employ a T7 RNA polymerase and a Phi6 RNA replicase in order to generate a 24 nucleotide blunt ended dsRNA (SEQ ID NOs: 59 and 60). As FIG. 11 illustrates, one may begin with a dsDNA in which one strand contains a first restriction site (shown as an ApaI site), a T7 promoter site sequence, an antisense sequence, and a second restriction site (shown as a DraI site) (SEQ ID NO: 55). The second strand may contain a second restriction site, a sense sequence, a sequence complementary to the T7 promoter sequences and a first restriction site (SEQ ID NO: 56). As persons of ordinary skill in the art will recognize, although the antisense sequence is referenced as being on the same strand as the T7 promoter site sequence and the sense sequence is referenced as being on the other strand, the sense sequence could be on the strand with the T7 promoter sequence while the antisense sequence is on the other strand. Additionally, the dsDNA can be constructed such that each strand contains 0-6 nucleotides 5' and/or 3' of the antisense sequence and complementary sequences 5' and/or 3' of the sense sequence. For example, there may be a GGG sequence 5' of a sequence of interest and/or a UUU sequence 3' of a sequence of interest. The GGG sequence arises from the canonical T7 promoter. The UUU sequence arises from the DraI site. Any blunt cutter can be used at the second restriction site, provided that the recognition site is present in the dsDNA oligonucleotide.

As shown in the figure, the dsDNA may be digested and cut with the restriction enzymes to form a duplex (SEQ ID NOs: 57 and 58). By way of example, next, T7 and Phi6 RNA polymerase may be used to generate dsRNA. As shown in FIG. 11, this dsRNA will be an siRNA in which each strand is 24 nucleotides long (SEQ ID NOs: 59 and 60).

According to another embodiment, the present invention provides a kit for the generation of a desired set of molecules for RNAi. In some embodiments, the kit comprises: (a) a pool of dsDNA oligonucleotides; (b) a first set of primers; and (c) a second set of primers. Optionally, the kit comprises at least 3, at least 5, at least 10 or at least 100 primer pairs, wherein each primer pair is capable of selectively amplifying a sequence of interest or a group of sequences of interest.

The dsDNA oligonucleotides of the pool may form a library as described in connection with any of the embodiments of the present invention. Thus, for example, the pool may comprise a plurality of dsDNA oligonucleotides, wherein each dsDNA oligonucleotide comprises, consists essentially of or consists of a first region, a sequence of interest and a second region, wherein the sequence of interest is between the first region and the second region, and the sequence of interest comprises a DNA sequence that corresponds to a region of a target RNA, wherein the first region is defined by a first sequence and the second region is defined by a second sequence, wherein the first sequence and the second sequence are in whole or part dissimilar from each other and the first sequence and the second sequence are at least 50% dissimilar from a region adjacent to said region of said target RNA and at least one of the following conditions exists: (i) the first sequence is unique for each dsDNA that contains a unique sequence of interest; (ii) the second sequence is unique for each dsDNA that contains a unique sequence of interest; or (iii) the combination of the first sequence and the second sequence is unique for each dsDNA that contains a unique sequence of interest.

By way of further example, each of one or more of the dsDNA oligonucleotides may contain a first region and/or a second region that is defined by a universal primer binding region and a unique identifier region. Optionally, one or both of the first region and the second region may further be defined by one or a pair of subset, group and subgroup identifier regions. Within a dsDNA oligonucleotide, preferably unique identifier regions are distinct, but the first universal primer region may be the same as or distinct from second universal primer region; the first subset identifier region may be the same as or distinct from the second subset identifier region (if present); the first group identifier region may be the same as or distinct from the second group identifier region (if present); and the first subgroup identifier region may be the same as or distinct from the second subgroup identifier region (if present).

Thus, in some embodiments, the first region comprises, consists essentially of or consist of the following elements: (a) a first universal primer region; (b) a first subset identifier region; and (c) a first unique identifier region; and the second region comprises, consists essentially of or consist of the following elements: (i) a second unique identifier region; (ii) a second subset identifier region; and (iii) a second universal primer region. In some embodiments, within each dsDNA oligonucleotide, the first universal primer region is not the same as the second universal primer region, the first subset identifier region is not the same as the second subset identifier region and the first unique identifier region is at least 50% dissimilar from the second unique identifier region. Alternatively, the first universal primer region is the same as the second universal primer region and/or the first subset identifier region is the same as the second subset identifier region.

Additionally, each dsDNA oligonucleotide may further comprise a promoter region and/or a first restriction site on a first side of the sequence of interest and/or a second restriction site on a second side of the sequence of interest. Optionally, there may be a second promoter site on the second side of the sequence of interest.

The first set of primers may be within a second compartment, wherein the first set of primers comprises a first primer that corresponds to a subsequence within the first region of a first subset of dsDNA oligonucleotides and a second primer that corresponds to a subsequence within the second region of the first subset of dsDNA oligonucleotides.

The second set of primers may be within a third compartment, wherein the second set of primers comprises a first primer that corresponds to a subsequence within the first region of a second subset of dsDNA oligonucleotides and a second primer that corresponds to a subsequence within the second subset of dsDNA oligonucleotides, wherein each of the first primer and the second primer within the second compartment and the first primer and the second primer in the third compartment are different. The subsequences to which the primer corresponds may be selected to correspond to sequences with a dsDNA or a plurality of dsDNA molecules that permit selective PCR to be conducted.

The kit may further comprise a first restriction enzyme that is capable of cleaving at the first restriction site and a second restriction enzyme that is capable of cleaving at the second restriction site.

Additionally, the kit may further comprise a fourth compartment wherein the fourth compartment comprises a universal primer, wherein the universal primer corresponds to the first universal primer region. Optionally, in the fourth compartment or in a fifth compartment there is a universal primer, wherein the universal primer corresponds to the second universal primer region.

In embodiments in which the first region and/or the second region contain subset, group or subgroup regions, the kit may also contain compartments that contain primers that correspond to these regions. Each compartment may, for example, contain only one type of primer or if there is a plurality of primers, an inclusion of a type of primer that would permit obtaining desired isolated and molecular clones while excluding isolated and molecular clones that are not desired. Thus, each primer of a primer pair may be specific to a subset, group, subgroup, or sequence of interest, or one primer of a primer pair may be specific to a subset, group, subgroup, or sequence of interest or the combination of a primer pair may be specific to a subset, group, subgroup, or sequence of interest. Each kit may contain primer pairs for one or more if not all of these subsets, groups, subgroups, and/or sequences of interest. Furthermore, a kit may contain one primer pair for each type of subsequence in the dsDNA oligonucleotides or a plurality of primer pairs for one or more the primer pair types. For example, there may be one compartment of a primer pair that corresponds to the universal primers, more than one compartment of primer pairs for primers that correspond to subset primer pairs and more than one compartment of primer pairs for primers that correspond to identifier regions. In some embodiments, there may be an increasing number of compartments with different primer pairs that correspond to regions on the dsDNA oligonucleotides closer to the sequences of interest.

As noted above, the library (or pool) of dsDNA oligonucleotides contains a plurality of dsDNA molecules that contain different sequences of interest (that may be targeting sequences or sequences that are complementary to targeting sequences or both). The plurality of sequences of interest may be complementary to or the same as sub-sequences of the same gene or of different genes of the same pathway or of genes of different pathways. Furthermore, in some embodiments for one or more of the sequences of interest, the targeting region is a non-coding region, while in other embodiments, all of the targeting regions are non-coding regions and in still other embodiments none of the targeting regions are non-coding regions.

FIG. 1 further illustrates various embodiments of the present invention. As shown in that figure, one begins with a complex oligonucleotide library, which refers to an oligonucleotide library with a plurality of different sequences of interest between two primer binding regions, which correspond to the first region and the second region. Within the first region and/or the second region, there may be a plurality of subregions as described in connection with various embodiments above and thus multiple primer binding region. One or more subregions may be common amongst a group of sequences or unique to individual sequences within the pool. These subregions may be pre-designed into the library or added later. For any subregion that is present in only the first region or the second region, during PCR the primer for that subregion may be used with a universal primer that corresponds to a region that is located on the other side of the sequence of interest.

When there is a plurality of subregions, the subregions may be nested so that as one moves closer to the sequence of interest, the primers correspond to regions within a smaller number of dsDNA oligonucleotides. Additionally, when there is a plurality of primers, the primers may correspond to distinct subregions within the first region that overlap or that do not overlap. Similarly, when there is a plurality of primers, the primers may correspond to distinct subregions within the first region that overlap or that do not overlap.

As FIG. 1 at the rights side shows, one may isolate and amplify a single molecular clone from a complex library so that all dsDNA oligonucleotides that are amplified contain the same sequence of interest. Then one may either clone those sequences into a plasmid for expression and restriction digest cloning or assembly cloning. Alternatively, one may use the DNA template for enzymatic RNA generation in the presence of any polymerase, replicase or endoribonuclease that can enzymatically generate single or double stranded RNA.

In another embodiment shown in FIG. 1, rather than isolate and amplify a single molecular clone, one may isolate and amplify a subset of molecular clones from the complex library that have different sequences of interest. This may be accomplished by using a plurality of primer pairs that correspond to regions within the first region and the second region of different dsDNAs or one primer pair that corresponds to subregions within the first and second regions of dsDNAs of different sequences of interest. Then one may either clone those sequences into plasmids for expression and restriction digest cloning or assembly cloning. Alternatively, one may use the DNA template for enzymatic RNA generation in the presence of any polymerase, replicase or endoribonuclease that can enzymatically generate single or double stranded RNA.

Figure 5:
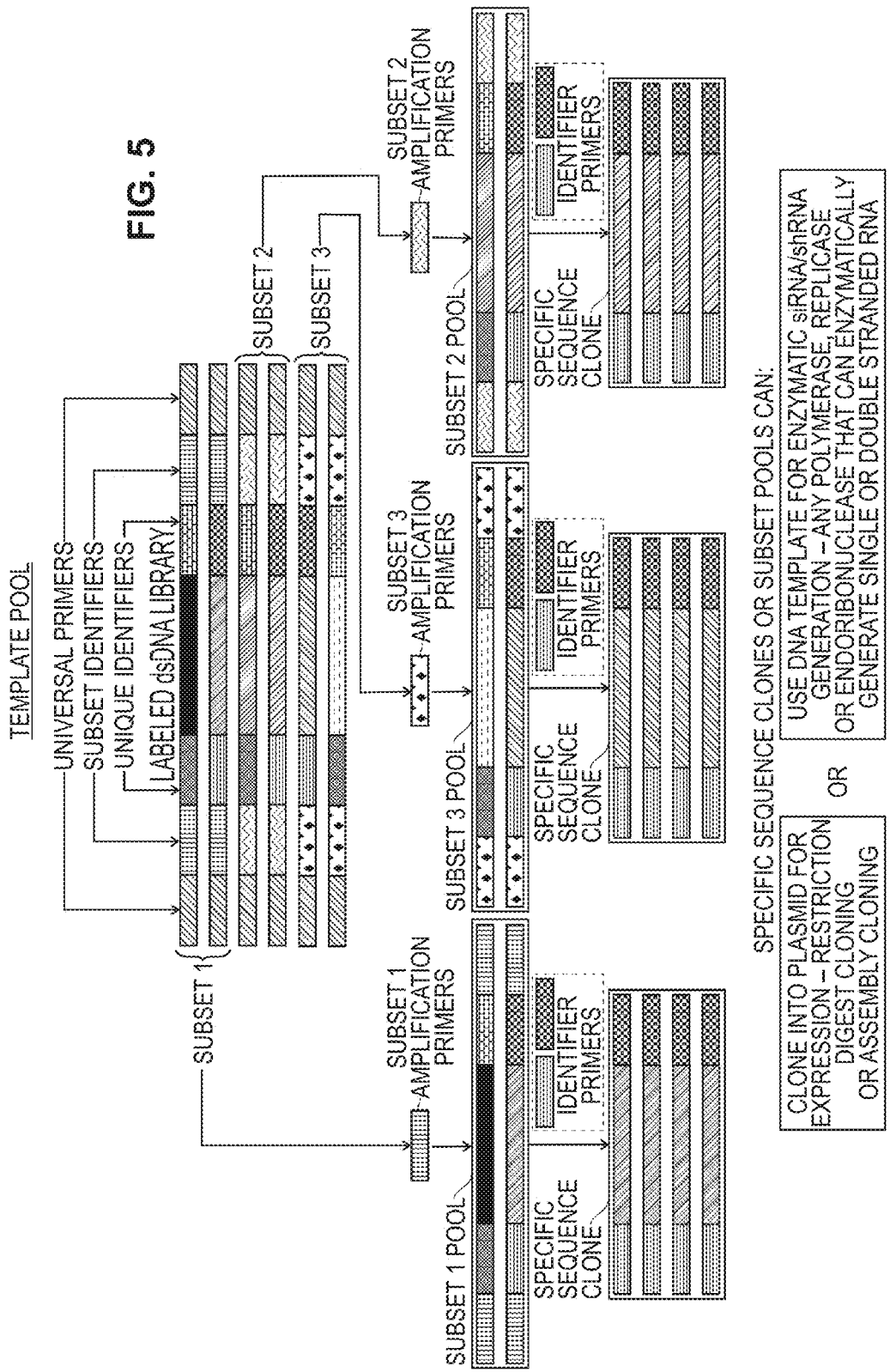
FIG. 5 is a representation of a strategy for using nested primers to generate RNAi molecules.

According to an embodiment shown in FIG. 5, within a template pool, there is a plurality of nucleic acid templates. Each dsDNA sequence may contain six different primer binding sites. The primer binding site elements and the sequence of interest may be arranged in the following order: (1) a first universal primer binding site that enables amplification of the entire library and thus is associated with every sequence of interest; (2) a first subset specific primer binding site (subset identifier) that allows selective amplification of a subset of molecules from the library; (3) a first unique primer binding site (unique identifier) that allows amplification of a particular sequence from a subset; (4) a sequence of interest; (5) a second unique primer binding site (unique identifier); (6) a second subset specific primer binding site (subset identifier); and (7) a second universal primer binding site.

According to this design, either: (1) all pairs of unique primer binding sites (identifiers) may be distinct; or (2) within each subset, the pair of unique primer binding sites are distinct, but the same unique primer binding site may appear in more than one subset. In the latter case, within the entire library, each unique primer binding site alone would not necessarily be unique and each unique primer identifier site pair (upstream and downstream of the sequence of interest) would not necessarily be unique, but either a single unique identifier or unique identifier pair in combination within a subset identifier would be unique. One of the advantages of this strategy is that it maximizes the utility of primer stocks because they can be applied to obtain multiple different sequences from the library. Additionally, one could use the same primers in different libraries, thereby reducing the amount of storage space reserved for PCR primers while maximizing the value of primers to be used.

One will also note that the first universal primer binding site may be the same as (or complementary to) or distinct from the second universal primer binding site. Similarly, the first subset identifier may be the same as (or complementary to) or distinct from the second identifier.

As FIG. 5 further illustrates, within the template pool, there is a plurality of sequences. All dsDNA oligonucleotides share the same universal primers. Within each of subset 1, subset 2 and subset 3, the subset identifiers are the same, but across the subsets, they are different. Finally, each unique identifier within a dsDNA molecule is different, and the pair of unique identifiers is distinct within the subset.

Additionally, as shown in the figure, for a given sequence of interest, the unique identifier on each side of the sequence of interest is different. Thus, in order to obtain specific sequences of interest, the figure shows initial steps of separating subsets by the subset amplification primers. As a person of ordinary skill in the art will appreciate, although all three subsets are shown as being amplified from the same template pool, in practice, only one subset would be amplified from a particular copy of the pool. Thus, the product is a separate pool for each subset. In order to obtain the specific sequence clones that one desires, one uses the corresponding identifier primers within a subset pool.

One may use the specific sequence clones or subset pools in one of two ways. First, they may be cloned into a plasmid of expression-restriction digest cloning or assembly cloning. Alternatively, one may use the DNA template for enzymatic siRNA/shRNA generation. This may be accomplished by any polymerase, replicase or endoribonuclease that can enzymatically generate single or double stranded RNA.

Figure 12A:
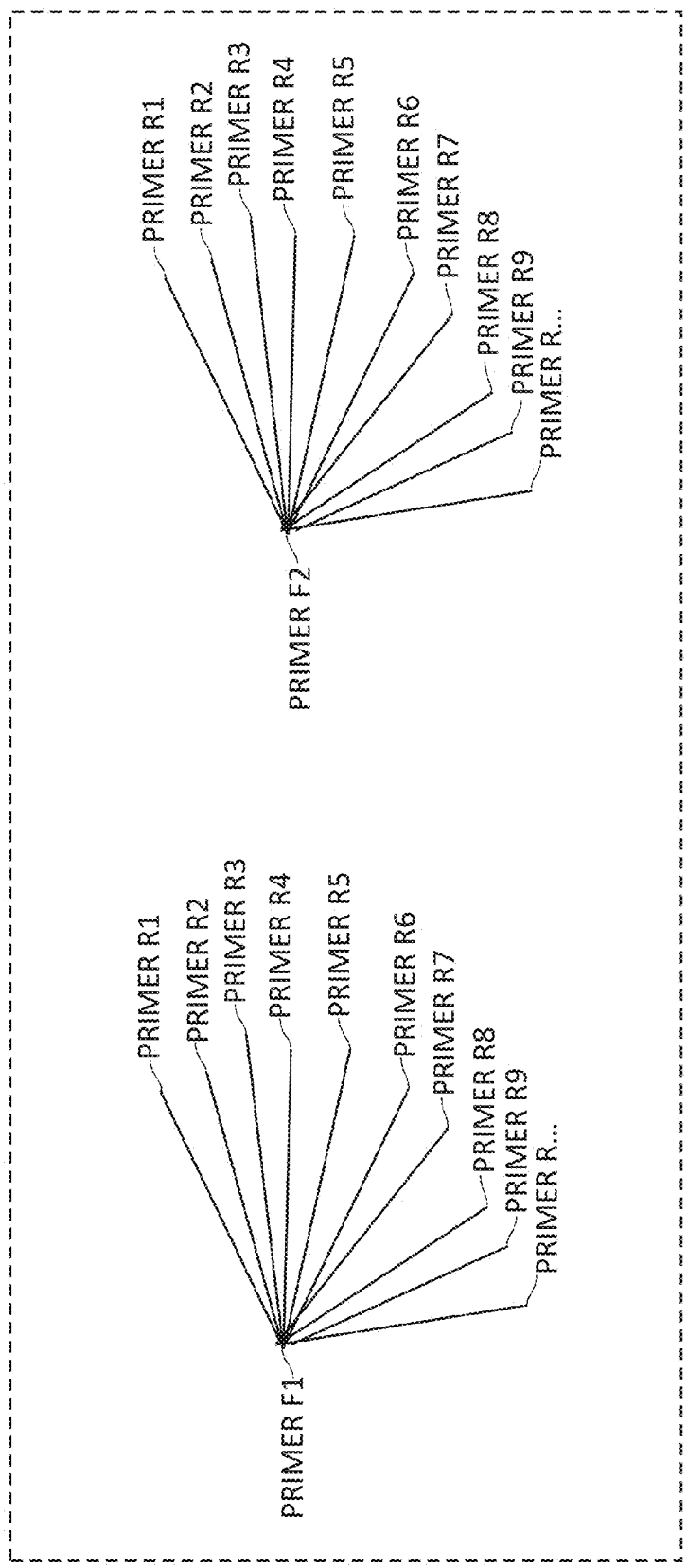
FIGS. 12A and 12B are representations of combinatorial PCR methods for isolating specific clones from a complex mixture using a minimal number of primers.
Figure 12B:
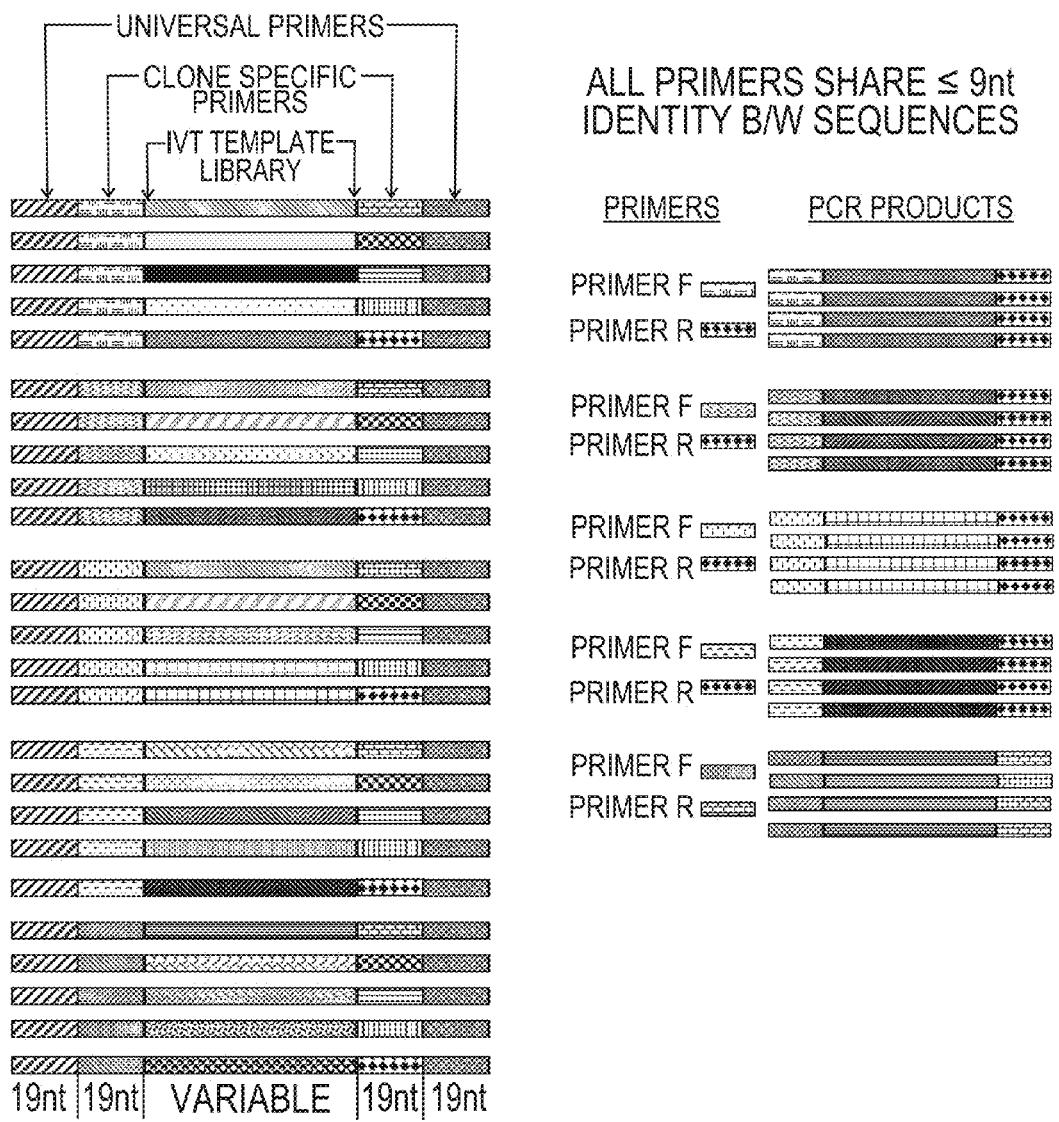

Various embodiments of the present invention may be further understood by reference to FIGS. 12A and 12B. These figures depict combinatorial PCR methods for isolating specific clones from a complex mixture using a minimal number of primers. FIG. 12A provides a diagram that illustrates the principle of combinatorial PCR. In this example, two different forward primers (Primer F1 and Primer F2) are paired with the same ten different reverse primers (Primer R1-R . . . , wherein " . . . " represents the last primer, e.g., if . . . =10, there are ten reverse primers).

If each forward and reverse primer combination is associated with a particular sequence, then when there are ten reverse primers, the total twelve primers (two forward primers and ten reverse primers) could be used to amplify twenty separate sequences. The example is meant to illustrate that the same primer binding sites can be used to amplify multiple different sequences individually by different combinations of forward primers and reverse primers. Although only two forward primers are shown, for each additional forward primer, without adding reverse primers, ten additional primer combinations can be generated.

FIG. 12B shows how primer binding sites may be arranged in combinatorial PCR, and how specific combinations of common forward and common reverse primers can be used to isolate and to amplify individual sequences from a complex pool. Either ssDNA or dsDNA molecules are synthesized such that every sequence is flanked at the 5' and 3' ends with sequences shared amongst all members of the library (universal primers). If primers capable of binding to these regions were used in a PCR reaction, then the entire library would be amplified because each sequence would be capable of being used as template. Internal to these universal primer binding sites are another set of primer binding sites (clone specific primers). These sequences flank the content of the library (IVT sequences).

In this example, each of the five different forward primer binding regions is present in connection with five different content sequences. Each different content sequence that is associated with the same forward primer has a binding site for a different reverse primer. Similarly, each reverse primer is present on five different content DNAs, but each of these content DNAs uses a different forward primer. Therefore, in this example, 10 different clone specific primers (five forward and five reverse) can be used to amplify each of the 25 different content DNAs by using every possible combination of these primers. The content sequences are denoted as IVT sequences, and these sequences may all be the same size or be of variable length. Each of the universal primer sequences and clone specific sequences are shown as being 19 nucleotides in length.

The right side of the figure illustrates how these primers could be combined to amplify different unique content from the library. As shown, each of five combinations of forward and reverse primers yields different but specific products.

Figure 13:
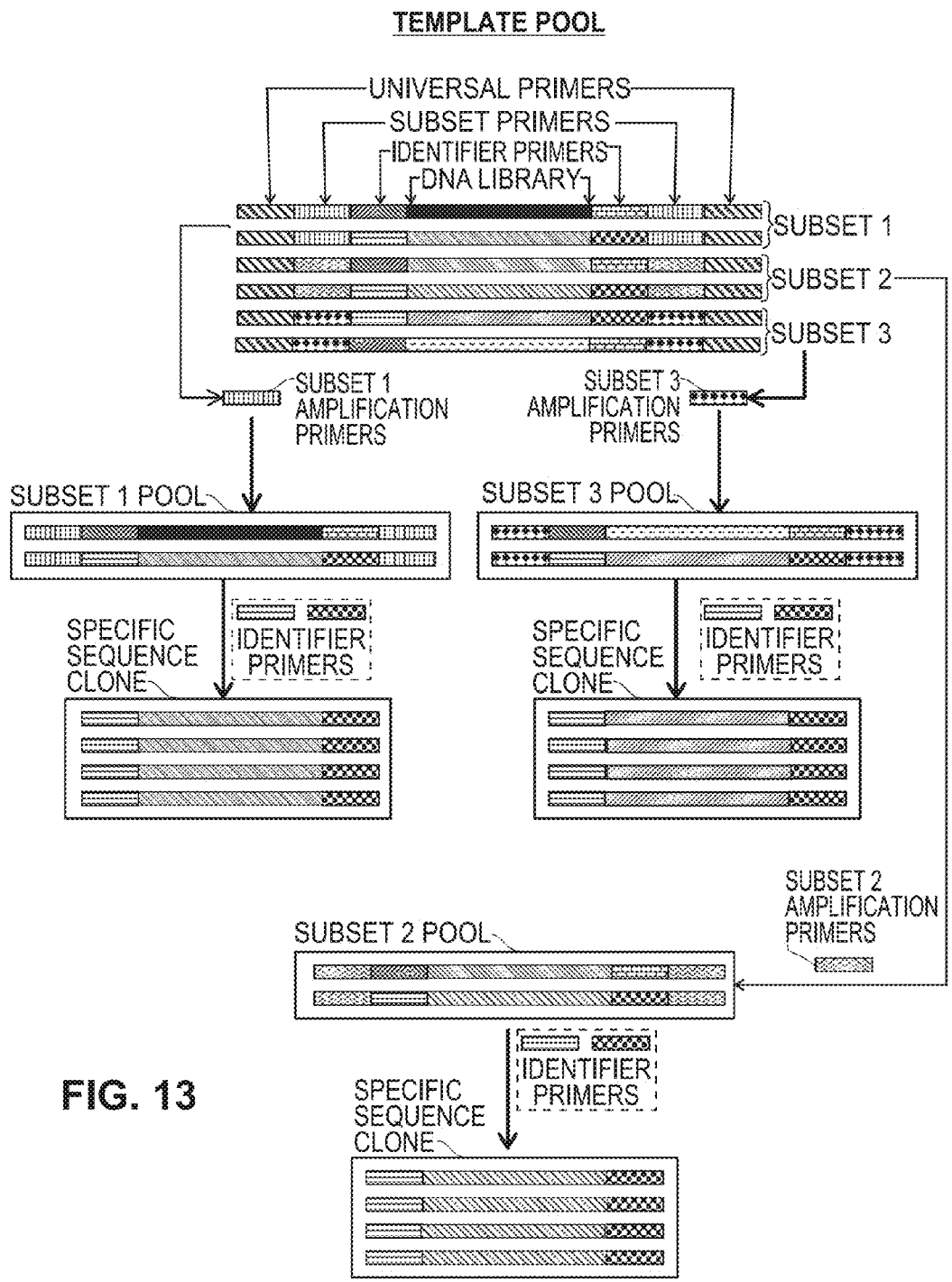
FIG. 13 is a representation of an iterative PCR strategy for isolation of specific DNA clones from a complex library.

FIG. 13 provides an example of an iterative PCR strategy for the isolation of specific DNA clones from a complex library. This figure illustrates a strategy that imparts three levels of organization among DNA content sequences. In this embodiment, within the template pool, each template sequence has a unique combination of subset and identifier primer binding sites. Thus, identifier primer pairs are shared between subsets but are unique within a subset.

Additionally, every sequence in a complex template pool possesses a common set of primer binding sites that flank all elements (universal primers). Internal to each universal primer binding site are two additional primer binding sites, subset primer binding sites for subset primers, and identifier primer binding sites for identifier primers. Multiple different content sequences may possess the same subset primer binding sites. In this example, three sets of two content sequences are associated with the same subset primers.

Within each subset, each sequence of interest (or possibly groups of sequences, depending on how the library is designed) will possess a unique pair of identifier primer binding sites. The advantage of this method comes from allowing multiple different content sequences to possess the same identifier primer binding sites as long as they do not share the same subset primer binding sites. Thus, this method allows one to amplify a group of sequences via their common subset primer binding sites or identifier primer binding sites. The method also allows one to amplify a specific sequence from the complex pool if iterative PCR reactions are done.

For example, if one wanted to recover the second sequence from the library, then one would conduct PCR in order to amplify subset 1 pool. This would be done under conditions known by persons of ordinary skill in the art to amplify sequences in the presence of subset 1 amplification primers. Next, the identifier primers associated with that sequence would be used to amplify the second sequence from the subset 1 pool. A similar standard may be used to isolate subset 2 pool and then one of the two sequences from that pool or to isolate the subset 3 pool and then a sequence from that pool.

In some embodiments, every primer is maximally dissimilar from every other primer, wherein maximal similarity is defined on lowest possible number of bases that align under an analysis of maximal sequence alignment. In some embodiments, the level of uniqueness for identifier primers is fewer than ten, fewer than nine, fewer than eight or fewer than seven nucleotides between sequences under conditions of maximal sequences alignment. A similar standard of uniqueness may apply to identifier primers. Although individual primer binding sites are present on multiple different sequences, each sequence of interest may be associated with a unique combination of subset and identifier primer binding sites. This feature gives this method tremendous flexibility, while minimizing the number of primers needed because a plurality of different DNA sequences of interest have the same identifier pairs, but different subset primers.

FIG. 14 provides an example of how to use specific combinations of subset and identifier primers to yield single PCR amplicons. The diagram provides the same organization as FIG. 13, but it shows how single products can be obtained from the library in either single or iterative PCR reactions.

The figure shows a template pool in which six different templates can be grouped into three subsets. All of the templates have the same universal primer binding regions, one at each end of each template. The first two templates have the same subset identifiers. The third and fourth templates also have the same subset identifiers, which are different from the subset identifiers that the first two templates share. Similarly, the fifth and sixth templates have the same subset identifiers, which are different from the subset identifiers that the first two templates share and are different from the subset identifiers that the third and fourth templates share.

With respect to the unique identifiers, within this figure, those identifiers are unique within a subset, but not across subsets. Thus, as shown by way of example, the pair of unique identifiers of the first template is the same as the pair of unique identifiers of the third and sixth templates and the pair of unique identifiers of the second template is the same as the pair of unique identifiers of the fourth and fifth templates. Thus, they are unique identifiers in combination with the subset identifiers, but not in their absence.

Because every content DNA has a unique combination of subset and identifier primer binding sites, two different possible combinations of subset and identifier primers for a particular sequence can be used to recover a single sequence from the library in one PCR reaction. In a single step reaction, the combination of the subset 2F (forward) and identifier 2R (reverse) may be used (see number (1)) or the identifier 2F primer and the subset 2R primer may be used (see number (2)).

Alternatively, one could use a two-step process in order to isolate sequences from a template pool. As shown in FIG. 14, (see number (3)), initially subset 1 amplification primers are used, thereby allowing a user to obtain a subset 1 pool. Next, the identifier primers are used in order to isolate a specific sequence clone.

Figure 16:
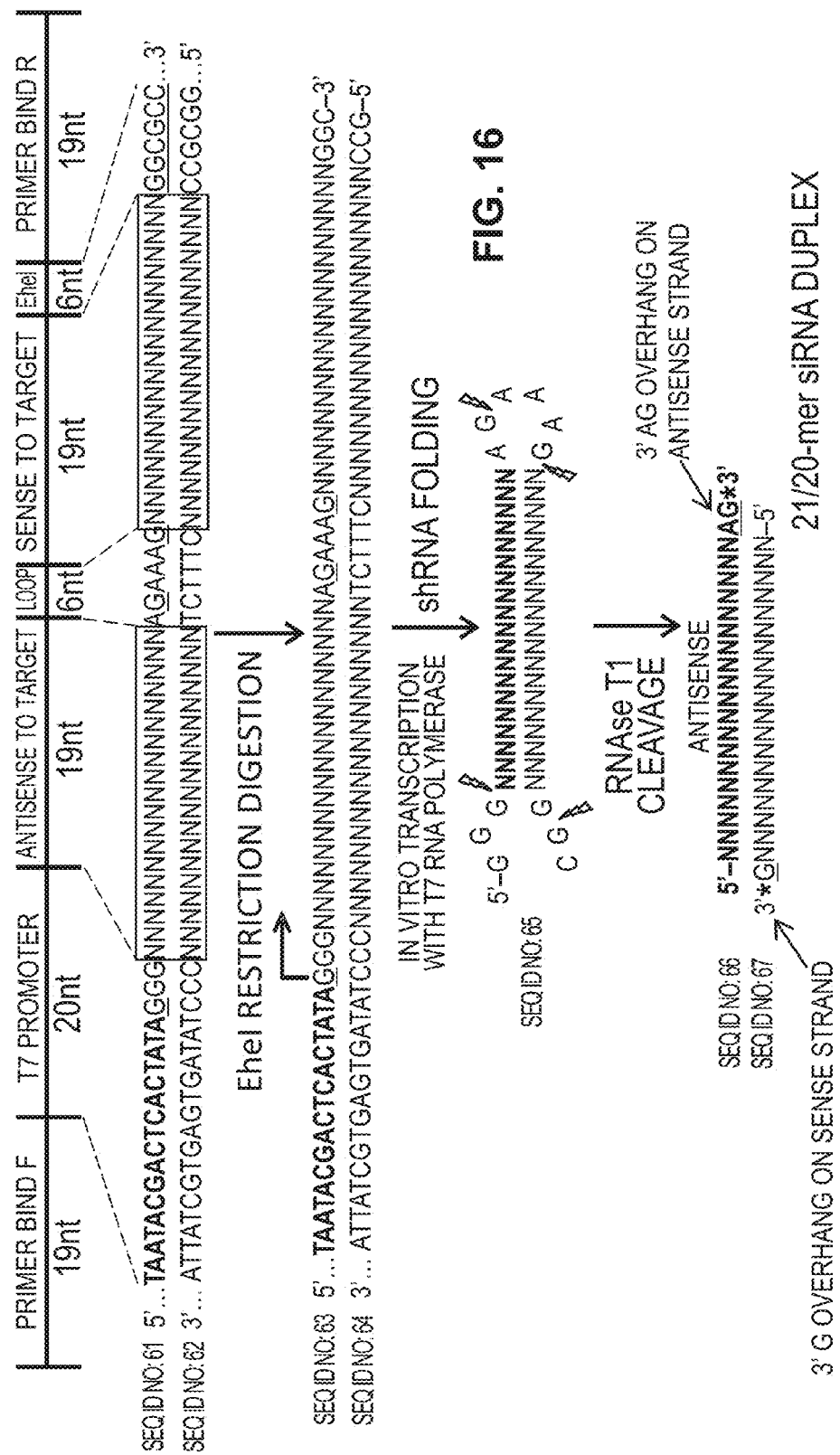
FIG. 16 is a representation of an example of a use of specific sequence elements as required for siRNA processing.

Another embodiment of the technology of the present invention provides for DNA directed synthesis of siRNAs or shRNAs. FIG. 16 demonstrates specific sequence elements required for siRNA processing, and shows the sequence organization of PCR products obtained using either combinatorial or iterative PCR methods of clone isolation. For siRNA synthesis, every sequence in a library would possess a T7 RNA polymerase promoter, which ends in GGG and is immediately upstream of 19 nucleotide of a sequence antisense to a chosen target. The target sequence may be selected using a proprietary algorithm, e.g., an algorithm such as ones disclosed in PCT/US01/14885, file May 12, 2004, published as WO 2006/006948 on Jan. 19, 2006.

Immediately downstream of the antisense sequence is a six nucleotide sequence that is a loop forming sequence and possesses a G at the second position and a G at the last position of the loop. Following the loop sequence is the 19 nucleotide reverse complement of the antisense sequence (sense to target), which is followed by an uncommon restriction enzyme site that produces a blunt end (EheI). A single PCR product or a pool of PCR products that may or may not target the same gene is first amplified from a pool of sequences with common organization. SEQ ID NO: 61 shows the region of the antisense strand downstream of the forward primer binding region (primer bind F), and contains the T7 promoter to the target (the antisense region), the loop, the sequence that is the same as the target (the sense region) and the EheI sequence. Within the library, the reverse primary binding region (primer bind R) is downstream of the EheI sequence. SEQ ID NO: 62 is complementary to SEQ ID NO: 61. In some embodiments, the regions as shown may be immediately downstream or upstream of each other.

This molecule is then cut with a restriction enzyme to produce a blunt end duplex. Thus, following digestion with EheI, the duplex of SEQ ID NO: 63 and SEQ ID NO: 64 is generated. The cut DNA is then used as a template in an in vitro transcription reaction with T7 RNA polymerase. T7 RNA polymerase begins transcription from the underlined G (bent arrow). The antisense loop sense organization of the DNA template results in a shRNA product (SEQ ID NO: 65) with the indicated nucleotides remaining as single stranded. RNAse T1 can be used to cleave the 3' single stranded portions of the shRNA at G residues, which yields a 21/20-mer siRNA duplex with a AG 3' overhang on the antisense strand, SEQ ID NO: 66, and a 3' G overhang on the sense strand, SEQ ID NO: 67. The mechanism of RNAse T1 leaves 3' phosphates at cleavage sites (asterisks).

Figure 18B:
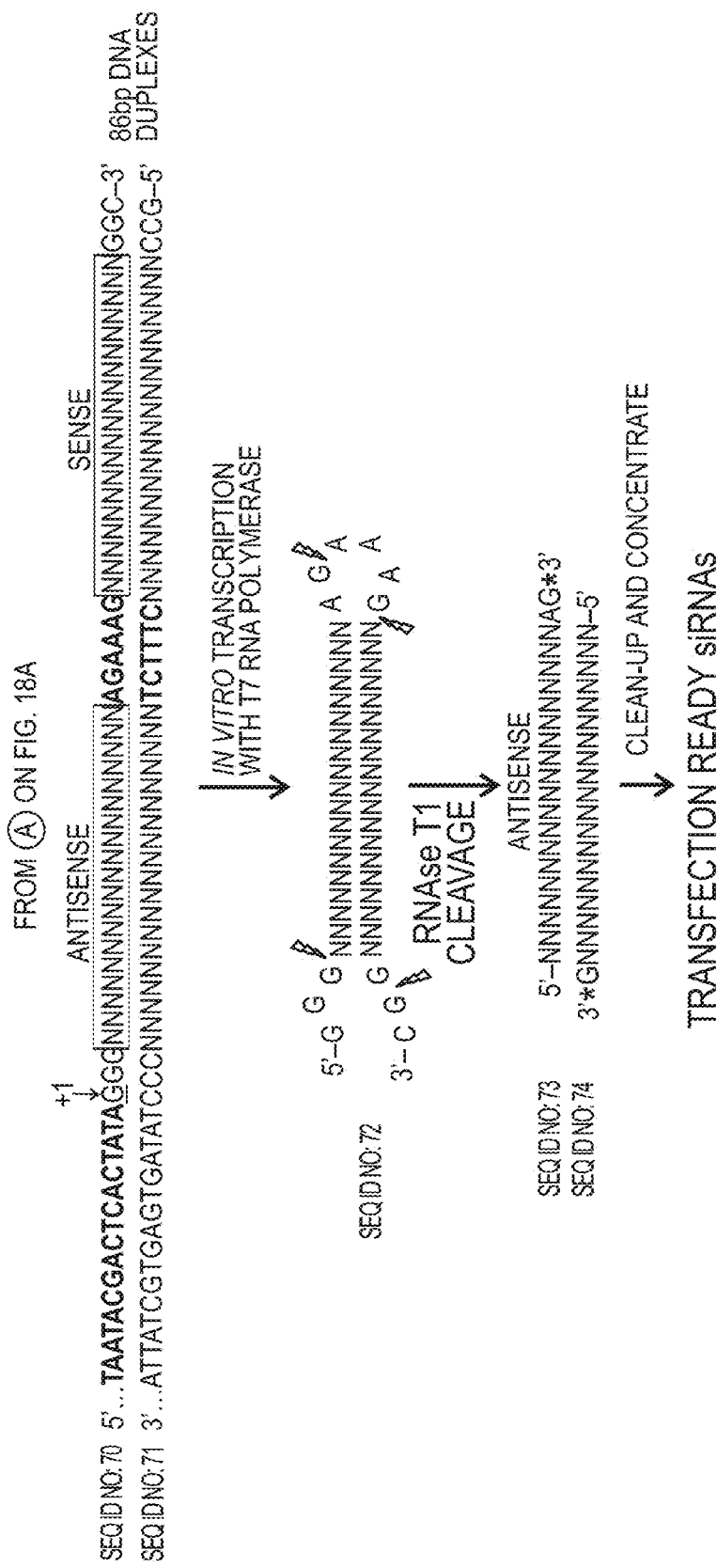

Various embodiments of the present invention that provide for the general workflow for producing siRNAs from DNA templates and are illustrated by FIGS. 18A and 18B. Single constructs are first amplified from a pool of thousands of DNA sequences using the combinatorial PCR strategy described in this specification. Thus, each construct possesses sequence elements that allow it to be transcribed into a shRNA and cleaved into a siRNA by RNAse T1. Accordingly, one begins with an IVT (in vitro transcription) template library, wherein each molecule contains a first universal primer binding region of 19 nucleotides in length, followed by a first clone specific primer binding region of 19 nucleotides in length followed by a sequence of interest of variable length, followed by a second clone specific primer binding region of 19 nucleotides in length, followed by a second universal primer binding region of 19 nucleotides in length.

Each construct corresponds to a specific cellular RNA that may, for example, be selected based on an algorithm as described above or based on predicted transcripts for a particular species. Possible multiple siRNA targeting sequences are generated for a particular RNA target, so that multiple siRNAs can be used to reduce expression of that single target in a singular or pooled fashion. Thus, single PCR products that target a common RNA or possibly multiple different RNAs can therefore be pooled and processed as a pool in steps following the initial PCR reaction.

In the figure, the PCR products are shown as being obtained by use of sequence specific primers and are 108 bps in length. Next, they are cut with a restriction enzyme (EheI), which targets a sequence that is infrequently present in siRNA designs and absent from the T7 RNA polymerase promoter. Thus, as shown in the figure, the process generates SEQ ID NOs: SEQ ID NO: 68 and SEQ ID NO: 69. EheI leaves a blunt ended product that terminates in GGC. The cleaved PCR product(s) are then purified to remove non-DNA components from the 3' cleavage to generate 86 base pair duplexes, a portion of which are shown in SEQ ID NOs: 70 and 71. Next, one concentrates PCR reaction products to be used in an in vitro transcription reaction with T7 RNA polymerase to generate SEQ ID NO: 72. The RNA products from the transcription reaction fold into a shRNA structure with 5' GGG overhang, a dsRNA region, a loop sequence composed of AGAAAG, and a 3' overhang of GGC. This shRNA structure can then be cleaved by RNAse T1 to produce siRNAs with a 3' AG overhang on the antisense (targeting strand) and 3' G overhang on the sense strand SEQ ID NO: 73 and SEQ ID NO: 74. The siRNAs are then purified away from the enzymes, free ribonucleotide triphosphates, and buffer components used in the transcription and RNAse T1 cleavage reactions. Optionally, these siRNAs may be dephosphorylated at their 3' ends (asterisks) to remove 3' phosphates left over from the RNAse T1 cleavage mechanism. These purified siRNAs are then ready for transfection into the cell line of choice via standard methods.

Various aspects of the present invention have been described for use in connection with one or more embodiments. However, unless explicitly stated or otherwise apparent from context, each feature described above in any one embodiment may be used in connection with any and all embodiments.

EXAMPLES

Example 1

Combinatorial PCR Strategy Preferentially Amplifies Specific Targets

FIGS. 15A1, 15A2 and 15B demonstrate the results of the use of a combinatorial PCR strategy to amplify specific targets preferentially. Twelve thousand different content sequences were synthesized in a pooled format and organized such that each sequence had a unique combination of one of 100 different forward primers and one of 120 different reverse primers as illustrated in FIG. 12B.

FIGS. 15A1 and 15A2 show agarose gel images of 48 PCR products that were amplified from the 12,000 sequence library using the combinatorial PCR strategy and two different thermal cycling conditions.

Figure 15B:
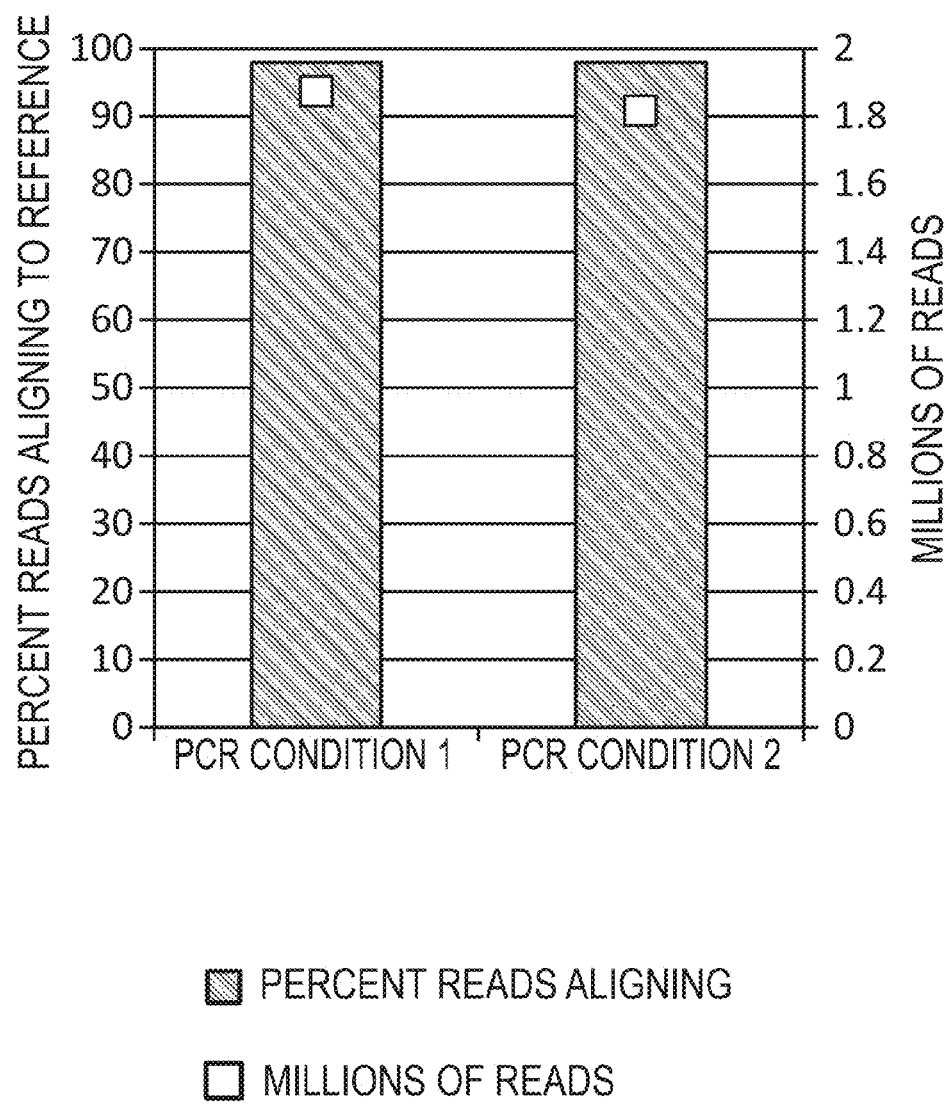

FIG. 15B shows data that corresponds to the pooling of the products from the 48 PCR reactions after having been subjected to deep DNA sequencing analysis. Using the 48 intended PCR products as a reference, more than 97.5% of the more than 1.8 million reads in each PCR condition matched this reference (shown as bar graph and point plot). This data illustrates that the combinatorial PCR strategy produces specific products and is a reliable method for isolating specific sequences from a complex pool using a minimal number of primers.

Example 2

Functional siRNAs as Generated from DNA Templates

Figure 17A:
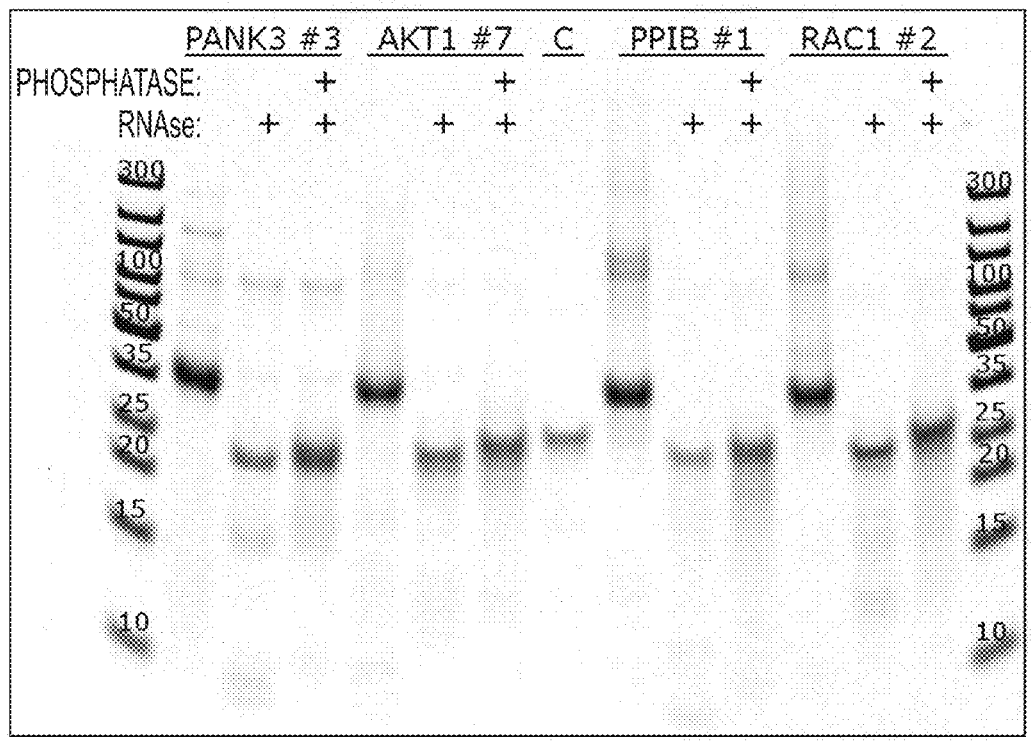
FIG. 17A provides a gel that measures the presence of four siRNAs under the following conditions: in the presence of neither phosphatase nor RNAse; in the presence of RNAse but not phosphatase; and in the presence of both RNAse and phosphatase.

Using the DNA template organization and reaction steps shown in FIG. 16, functional siRNAs were generated enzymatically. FIG. 17A shows an acrylamide gel in which the products from enzymatic shRNA and siRNA synthesis for four different targets were amplified from a 12,000 sequence library. A chemically synthesized control 21/20-mer duplex (C) is shown to illustrate size and purity of products. The mechanism of RNAse T1 cleavage leaves a 3' phosphate at cleaved residues, which causes the duplexes to migrate through gel faster than the control. Phosphatase treatment of the enzymatic siRNAs removes these 3' phosphates and slows the migration of the duplexes to more closely match the chemically synthesized control duplex, which lacks those phosphates.

Figure 17B:
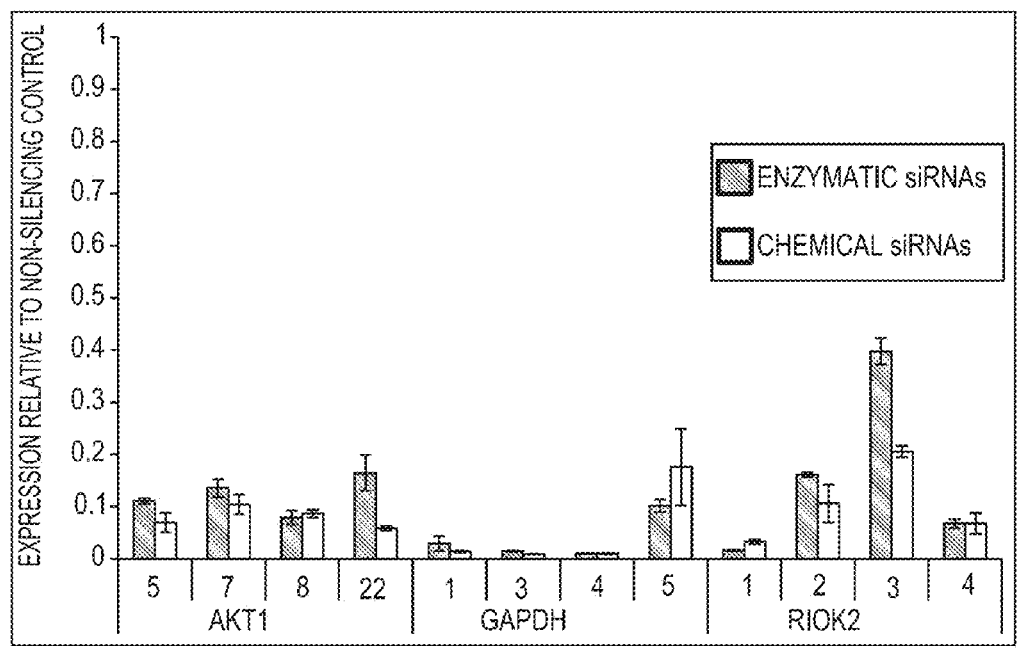
FIG. 17B provides a bar graph that measures expression levels relative to non-silencing controls for enzymatic siRNAs and chemical siRNAs that have been generated from a library of the present invention.

FIG. 17B shows RT-qPCR data showing the knockdown effect of enzymatically synthesized siRNAs compared to chemically synthesized controls with the same targeting sequence and more common symmetric 3' UU overhangs. The knockdown is relative to a chemically synthesized non-silencing control and was calculated using the ΔΔCt method. From this example, one can see that enzymatically synthesized siRNA demonstrate similar gene knockdown to the gene knockdown of chemically synthesized siRNA.

The invention claimed is:

1. A library of DNA molecules, wherein the library comprises a plurality of DNA molecules, wherein each DNA molecule comprises a sequence of interest located between a first primer binding region and a second primer binding region, wherein for each DNA molecule the combination of the first primer binding region and the second primer binding region is unique to the sequence of interest and within each DNA molecule the sequence of interest is located upstream of one of the first primer binding region and the second primer binding region, and downstream of the other of the first primer binding region and the second primer binding region, and within a first subset of DNA molecules, each of a plurality of DNA molecules has the same first primer binding region and a different second primer binding region and within a second subset of DNA molecules, each of a plurality of DNA molecules has the same first primer binding region and a different second primer binding region, wherein the first primer binding region of the first subset is distinct from the first primer binding region of the second subset and wherein if a sequence of interest codes for or is complementary to a molecule of an organism, less than 50% of the sequence of nucleotides immediately upstream and downstream of the sequence of interest is identical to or complementary to the sequence of nucleotides in the regions immediately upstream and downstream of the molecule of the organism.

2. The library of claim 1, wherein the library comprises at least 100 DNA molecules.

3. The library of claim 2, wherein there are at least 20 subsets, wherein each subset contains at least five DNA molecules, wherein in each subset each DNA molecule has the same first primer binding region and a different second primer binding region.

4. The library of claim 3, wherein, the first primer binding region is a reverse primer binding region and the second primer binding region is a forward primer binding region and each DNA molecule further comprises a first universal primer binding region and a second universal primer binding region, wherein for each DNA molecule, the forward primer binding region, the sequence of interest and the reverse primer binding region are located between the first universal primer binding region and the second universal primer binding region.

5. The library of claim 4, wherein each DNA molecule comprises a first restriction site and a second restriction site, wherein the first restriction site is located on one side of the sequence of interest and the second restriction site is located on the other side of the sequence of interest.

6. The library of claim 5, wherein the sequence of interest codes for a sequence selected from the group consisting of an siRNA, an shRNA, an miRNA mimic, an miRNA inhibitor, an lncRNA, an antisense RNA, an aptamer, a ribozyme and a small guide RNA, or codes for a complement of a sequence selected from the group consisting of an siRNA, an shRNA, an miRNA mimic, an miRNA inhibitor, an lncRNA, an antisense RNA, an aptamer, a ribozyme and a small guide RNA.

7. The library of claim 4, wherein each DNA molecule further comprises a T7 promoter sequence, wherein the T7 promoter sequence is located 5' of the sequence of interest.

8. The library of claim 1, wherein each DNA molecule further comprises a T7 promoter sequence, wherein the T7 promoter sequence is located 5' of the sequence of interest and the sequence of interest is an shRNA, wherein the shRNA comprises an antisense region, a loop region and a sense region.

9. The library of claim 1, wherein the first primer binding region is a forward primer binding region and the second primer binding region is a reverse primer binding region and the library further comprises a third subset, wherein each DNA molecule within the third subset has the same reverse primer binding region and a different forward primer binding region, and a fourth subset, wherein each DNA molecule within the fourth subset has the same reverse primer binding region and a different forward primer binding region and the reverse primer binding region of the fourth subset is distinct from the reverse primer binding region of the third subset.

10. A library of DNA molecules, wherein the library comprises a plurality of DNA molecules, wherein each DNA molecule comprises a sequence of interest located between a first primer binding region and a second primer binding region, wherein for a first group of sequences of interest, each sequence of interest is located between a first unique combination of the first primer binding region and the second primer binding region and for a second group of sequences of interest, each sequence of interest is located between a second unique combination of the first primer binding region and the second primer binding region, wherein within the library of DNA molecules the first group of sequences of interest comprises a plurality of sequences that code for a target of a first common pathway and the second group of sequences of interest comprises a plurality of sequences of interest that code for a target of a second common pathway, wherein within each DNA molecule the sequence of interest is located upstream of one of the first primer binding region and the second primer binding region, and downstream of the other of the first primer binding region and the second primer binding region, wherein the first combination is different from the second combination, and wherein if a sequence of interest codes for or is complementary to a molecule of an organism, less than 50% of the sequence of nucleotides immediately upstream and downstream of the sequence of interest is identical to or complementary to the nucleotides in the regions immediately upstream and downstream of the molecule of the organism.

11. The library of claim 10, wherein the first group of sequences of interest codes for a region of a first gene, and the second group of sequences of interest codes for a region of a second gene.

12. A method for isolating a group of nucleotide molecules of interest comprising:
   a. exposing the library of claim 4 to a first primer and a second primer, wherein either:
      (i) the first primer is capable of binding to the first universal primer binding region and the second primer is capable of binding to the reverse primer binding region of a group of DNA molecules, or
      (ii) the first primer is capable of binding to the second universal primer binding region and the second primer is capable of binding to the forward primer binding region of a group of DNA molecules;
   b. conducting PCR to generate a PCR product; and
   c. isolating a group of nucleotide molecules of interest from the PCR product.

13. A method of cloning a DNA sequence comprising:
   a. inserting a nucleotide of interest from the group of nucleotides of interest of claim 12 into an expression vector thereby generating an expression vector comprising the nucleotide molecule of interest;
   b. delivering the expression vector comprising the nucleotide molecule of interest to a cell; and
   c. exposing the cell to conditions that permit cloning to occur.

14. The method according to claim 13, wherein said delivering is via viral particles.

15. A method of cloning a group of DNA sequences comprising:
   a. inserting the group of nucleotide molecules of interest of claim 12 into expression vectors thereby generating expression vectors comprising the nucleotide molecules of interest;
   b. delivering the expression vectors comprising the nucleotide molecules of interest to cells; and
   c. exposing the cells to conditions that permit cloning to occur.

16. The method according to claim 15, wherein said delivering is via viral particles.

* * * * *